(12) United States Patent
Wang et al.

(10) Patent No.: US 12,312,391 B2
(45) Date of Patent: *May 27, 2025

(54) ANTI-MUTATED KRAS T CELL RECEPTORS

(71) Applicant: The United States of America, as represented by the Secretary, Department of Health and Human Services, Bethesda, MD (US)

(72) Inventors: Qiong J. Wang, Highland Park, NJ (US); Zhiya Yu, Potomac, MD (US); James C. Yang, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 526 days.

This patent is subject to a terminal disclaimer.

(21) Appl. No.: 17/535,318

(22) Filed: Nov. 24, 2021

(65) Prior Publication Data

US 2022/0088164 A1 Mar. 24, 2022

Related U.S. Application Data

(63) Continuation of application No. 15/528,813, filed as application No. PCT/US2015/062269 on Nov. 24, 2015, now Pat. No. 11,207,394.

(60) Provisional application No. 62/171,321, filed on Jun. 5, 2015, provisional application No. 62/084,654, filed on Nov. 26, 2014.

(51) Int. Cl.
| | |
|---|---|
| C07K 14/725 | (2006.01) |
| A61K 39/00 | (2006.01) |
| C07K 14/82 | (2006.01) |
| G01N 33/574 | (2006.01) |
| A61K 38/00 | (2006.01) |

(52) U.S. Cl.
CPC .. C07K 14/7051 (2013.01); A61K 39/001164 (2018.08); A61K 39/461 (2023.05); A61K 39/4632 (2023.05); A61K 39/464464 (2023.05); C07K 14/82 (2013.01); C12Y 306/00 (2013.01); G01N 33/5748 (2013.01); A61K 38/00 (2013.01); A61K 2239/38 (2023.05); A61K 2239/54 (2023.05); G01N 2333/914 (2013.01)

(58) Field of Classification Search
None
See application file for complete search history.

(56) References Cited

U.S. PATENT DOCUMENTS

| | | | |
|---|---|---|---|
| 7,709,002 | B1 | 5/2010 | Schlom et al. |
| 8,034,334 | B2 | 10/2011 | Dudley et al. |
| 8,383,099 | B2 | 2/2013 | Dudley et al. |
| 11,207,394 | B2 * | 12/2021 | Wang ............... A61K 39/001164 |
| 2009/0304657 | A1 * | 12/2009 | Morgan .............. G01N 33/6893 435/372 |
| 2012/0244133 | A1 | 9/2012 | Rosenberg et al. |
| 2023/0181639 | A1 | 6/2023 | Jia et al. |

FOREIGN PATENT DOCUMENTS

| | | | |
|---|---|---|---|
| CN | 1305495 A | 7/2001 | |
| CN | 102712953 A | 10/2012 | |
| CN | 104131034 A | 11/2014 | |
| CN | 105802909 A | 7/2016 | |
| CN | 108395479 A | 8/2018 | |
| CN | 113621071 A | 11/2021 | |
| GB | 2 328 689 A | 3/1999 | |
| JP | 2001-514190 A | 9/2001 | |
| WO | WO 99/10382 | 3/1999 | |
| WO | WO 99/58552 A2 | 11/1999 | |
| WO | WO-2007017201 A1 * | 2/2007 | ............ A61P 31/00 |
| WO | WO 2008/089053 A2 | 7/2008 | |
| WO | WO 2011/034906 A2 | 3/2011 | |
| WO | WO-2014083173 A1 * | 6/2014 | ......... A61K 39/0011 |

OTHER PUBLICATIONS

Woodsworth et al., Genome Medicine 2013, 5:98. (Year: 2013).*
Robins et al., Blood. 2009;114:4099-4107. (Year: 2009).*
Subbramanian et al. (Nat Biotechnol. Nov. 2004;22(11):1429-34). (Year: 2004).*
Liu et al., "T cell adoptive immunotherapy targeting tumor KRAS mutations," *The Journal of Evidence-Based Medicine*, 17(1): 37-41 (Feb. 2017).
Yi et al., "Analysis of KRAS gene mutations in non-small cell lung cancer," *Chinese J Clinicians*, 7(20): 9111-9115 (Oct. 15, 2013).
Anonymous: "Murine TRAV19," Oct. 29, 2014 Retrieved from https://rest.uniprot.org/unisave/Q5R1A8?format=txt&versions=47, 1 pp. (Jan. 17, 2024).
"Government-Owned Inventions; Availability for Licensing," Notice published on Apr. 10, 2015 on the web at https://www.federalregister.gov/articles/2015/04/10/2015-08290/government-owned-inventions-availability-for-licensing, 9 pp.

(Continued)

*Primary Examiner* — Zachary S Skelding
(74) *Attorney, Agent, or Firm* — Leydig, Voit & Mayer

(57) ABSTRACT

Disclosed is an isolated or purified T cell receptor (TCR) having antigenic specificity for an HLA-A11-restricted epitope of mutated Kirsten rat sarcoma viral oncogene homolog (KRAS) (KRAS$_{7-16}$), Neuroblastoma RAS Viral (V-Ras) Oncogene Homolog (NRAS), or Harvey Rat Sarcoma Viral Oncogene Homolog (HRAS). Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

18 Claims, No Drawings

Specification includes a Sequence Listing.

(56) References Cited

OTHER PUBLICATIONS

Abrams et al., "Generation of Stable CD4+ and CD8+ T Cell Lines from Patients Immunized with ras Oncogene-Derived Peptides Reflecting Codon 12 Mutations," *Cellular Immunology*, 182:137-151 (1997).
Abrams et al., "Identification of overlapping epitopes in mutant ras oncogene peptides that activate CD4+ and CD8+ T cell responses," *European Journal of Immunology*, 26(2):435-443 (Feb. 1, 1996).
Anonymous "Uniprot: A0A075B5I2," Retrieved from http://ibis.internal.epo.org/exam/dbfetch.jsp?id=UNIPROT:A0A075B5I2, 1 pp. (Oct. 1, 2014).
Anonymous "Uniprot: Q5R1F9", Retrieved from http://ibis.internal.epo.org/exam/dbfetch.jsp?id=UNIPROT:Q5R1F9, 1 pp. (Jan. 4, 2005).
Bergmann-Leitner et al., "Identification of a Human CD8+ T Lymphocyte Neo-epitope Created by a ras Codon 12 Mutation Which is Restricted by the HLA-A2 Allele," *Cellular Immunology*, 187:103-116 (1998).
Bristol et al., "Identification of a ras oncogene peptide that contains both CD4(+) and CD8(+) T cell epitopes in a nested configuration and elicits both T cell subset responses by peptide or DNA immunization," *Cellular Immunol.*, 205: 73-83 (2000).
Cohen et al., "T-Cell Receptor-Like Antibodies: Targeting the Intracellular Proteome Therapeutic Potential and Clinical Applications," *Antibodies*, 2:517-534 (Sep. 2013).
Dudley et al., "Generation of tumor-infiltrating lymphocyte cultures for use in adoptive transfer therapy for melanoma patients," *J. Immunother.*, 26(4):332-42 (2003).
Fujii et al., "Clinical significance of KRAS gene mutation and epidermal growth factor receptor expression in Japanese patients with squamous cell carcinoma of the larynx, oropharynx and hypopharynx," *Int J Clin Oncol.*, 18: 454-463 (Mar. 2013).
Gaudernack "T cell responses against mutant ras: a basis for novel cancer vaccines," *Immunotechnology*, 2(1): 3-9 (Feb. 1996).
Gjertsen et al., "HLA-A3 restricted mutant ras specific cytotoxic T-lymphocytes induced by vaccination with T-helper epitopes," *J. Mol. Med.*, 81(1):43-50 (2003).
Gjertsen, et al., "Cytotoxic CD4+ and CD8+ T Lymphocytes, Generated by Mutant p21-ras (12VAL) Peptide Vaccination of a Patient, Recognize 12Val-Dependent Nested Epitopes Present Within the Vaccine Peptide and Kill Autologous Tumour Cells Carrying this Mutation," *Int. J. Cancer: 72*: 784-790 (1997).
Graef et al., "KIR2DS4 is a product of gene conversion with KIR3DL2 that introduced specificity for HLA-A*11 while diminishing avidity for HLA-C," *J. Exp Med*, 206, 11: 2557-2572 (2009).
He et al., "RAS Gene Mutations in Chinese Lekaemia Patients and Members of Family with High Incidence of Leukaemia," *Leukemia Research*, 20(11/12): 901-903 (1996).
He et al., "The relationship between KRAS gene mutations and HLA class 1 antigen," *J of International Medical Research*, 41(5): 1473-1483 (Mar. 2013).
International Bureau, International Search Report in International Application No. PCT/US2015/062269, 5 pp., mailed Mar. 7, 2016.
International Searching Authority, Written Opinion in International Application No. PCT/US2015/062269, 8 pp., mailed Mar. 7, 2016.
Jiang Ming et al., "The relationship between T-cell receptor polymorphism and disease," *Current Immunology*, 33 (3): 247-251 (Jun. 2013).
Kompier et al., "FGFR3, HRAS, KRAS, NRAS and PIK3CA Mutations in Bladder Cancer and their Potential as Biomarkers for Surveillance and Therapy," *PLoSONE*, 5(11): e13821, pp. 1-13 (2010).
Kubuschok et al., "Naturally occurring T-cell response against mutated p21 ras oncoprotein in pancreatic cancer," *Clin. Cancer Res.*, 12(4): 1365-1372 (2006).
Lindinger et al., "Induction of Murine ras Ocogene Peptide-Specific T Cell Responses by Immunization with Plasmid DNA-based Minigene Vectors," *Vaccine*, 21 (27-30): 4285-4296, (2003).
McKinney, "Brain Tumours: Incidence, Survival, and Aetiology," *J Neurol Neurosurg Psych*, 75: ii12-ii17 (2004).
Prigge et al., "No Evidence of Oncongenic KRAS mutations in squamous cell carcinomas of the anogenital tract and head and neck region independent of human papillomavirus and p16$^{INK4a}$ status," *Human Pathology*, 45: 2347-2354 (Nov. 2014).
Qin et al., "CD4+ T-cell immunity to mutated ras protein in pancreatic and colon cancer patients," *Cancer Res.*, 55(14):2984-87 (1995).
Quan et al., "KRAS Gene Mutation in Tumor Tissue and Peripheral Blood of Pancreatic Cancer Patients," Medical Recapitulate, 20(1): 136-139 (Jan. 2014).
Riddell et al., "The use of anti-CD3 and anti-CD28 monoclonal antibodies to clone and expand human antigen-specific T cells," *J. Immunol. Methods*, 128(2):189-201 (Apr. 17, 1990).
Shono et al., "Specific T-cell immunity against Ki-ras peptides in patients with pancreatic and colorectal cancers," *Br. J. Cancer*, 88(4): 530-536 (2003).
USPTO Memorandum, "2014 Procedure for Subject Matter Eligibility Analysis of Claims Reciting or Involving Laws of Nature/Natural Principles, Natural Phenomena, and/or Natural Products," 19 pages (2014).
USPTO, Evaluating Subject Matter Eligibility Under 35 USC 101: Mar. 2014 Update, 93 pages (2014).
Wang et al., Identification of T-cell Receptors Targeting KRAS-Mutated Human Tumors, *Cancer Immunology Research*, 4(3): 204-14 (Dec. 23, 2015).
Warren et al., "A census of predicted mutational epitopes suitable for immunologic cancer control," *Human Immunol.*, 71: 245-254 (2010).
U.S. Appl. No. 15/528,813, filed May 23, 2017.
Unpublished data comparing TCR TRAV4-4*01(1)/TRBV12-2*01 with other anti-RAS G12D TCRs, National Cancer Institute (5 pages).
Gjertsen et al., "Intradermal RAS Peptide Vaccination with Granulocyte-Macrophage Colony-Stimulating Factor as Adjuvant: Clinical and Immunological Responses in Patients with Pancreatic Adenocarcinoma," *Int. J of Cancer*, 92:441-450 (May 2001).

* cited by examiner

ANTI-MUTATED KRAS T CELL RECEPTORS

CROSS-REFERENCE TO RELATED APPLICATIONS

This patent application is a continuation of co-pending U.S. patent application Ser. No. 15/528,813, which is a U.S. national stage of PCT/US2015/062269, filed Nov. 24, 2015, which claims the benefit of U.S. Provisional Patent Application No. 62/084,654, filed Nov. 26, 2014 and U.S. Provisional Patent Application No. 62/171,321, filed Jun. 5, 2015, each of which is incorporated by reference in its entirety herein.

STATEMENT REGARDING FEDERALLY SPONSORED RESEARCH AND DEVELOPMENT

This invention was made with Government support under project number Z01BC011337-04 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 231,254 Byte ASCII (Text) file named "758115_ST25.txt," dated Nov. 23, 2021.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T cell receptor (TCR) having antigenic specificity for a mutated epitope, the mutated epitope (a) comprising VVVGADGVGK (SEQ ID NO: 2) or (b) consisting of VVVGAVGVGK (SEQ ID NO: 33) or VVGAVGVGK (SEQ ID NO: 35).

The invention further provides related polypeptides and proteins, as well as related nucleic acids, recombinant expression vectors, host cells, populations of cells, and pharmaceutical compositions relating to the TCRs of the invention.

Methods of detecting the presence of cancer in a mammal and methods of treating or preventing cancer in a mammal are further provided by the invention.

DETAILED DESCRIPTION OF THE INVENTION

Kirsten rat sarcoma viral oncogene homolog (KRAS), also referred to as GTPase KRas, V-Ki-Ras2 Kirsten rat sarcoma viral oncogene, or KRAS2, is a member of the small GTPase superfamily. There are two transcript variants of KRAS: KRAS variant A and KRAS variant B. Hereinafter, references to "KRAS" (mutated or unmutated) refer to both variant A and variant B, unless specified otherwise. Without being bound to a particular theory or mechanism, it is believed that, when mutated, KRAS may be involved in signal transduction early in the oncogenesis of many human cancers. A single amino acid substitution may activate the mutation. When activated, mutated KRAS binds to guanosine-5'-triphosphate (GTP) and converts GTP to guanosine 5'-diphosphate (GDP). The mutated KRAS protein product may be constitutively activated. Mutated KRAS protein may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers.

An embodiment of the invention provides an isolated or purified TCR having antigenic specificity for mutated human KRAS (hereinafter, "mutated KRAS"). Hereinafter, references to a "TCR" also refer to functional portions and functional variants of the TCR, unless specified otherwise. The inventive TCR may have antigenic specificity for any mutated KRAS protein, polypeptide or peptide. In an embodiment of the invention, the TCR has antigenic specificity for a mutated KRAS protein comprising or consisting of the amino acid sequence of SEQ ID NO: 1, 32, 122, or 123. The mutated KRAS variant A protein amino acid sequences of each of SEQ ID NOs: 1 and 32 generally corresponds to positions 1-189 of the unmutated, wild-type (WT) KRAS protein variant A amino acid sequence of SEQ ID NO: 29 with the exception that in SEQ ID NOs: 1 and 32, the glycine at position 12 is substituted with aspartic acid or valine, respectively. The mutated KRAS variant B protein amino acid sequences of each of SEQ ID NOs: 122 and 123 generally corresponds to positions 1-188 of the unmutated, WT KRAS protein variant B amino acid sequence of SEQ ID NO: 121 with the exception that in SEQ ID NOs: 122 and 123, the glycine at position 12 is substituted with aspartic acid or valine, respectively. In a preferred embodiment of the invention, the TCR has antigenic specificity for a mutated $KRAS_{7-16}$ peptide comprising or consisting of the amino acid sequence of VVVGADGVGK (SEQ ID NO: 2), or VVVGAVGVGK (SEQ ID NO: 33). The mutated KRAS peptide amino acid sequences of SEQ ID NOs: 2 and 33 generally correspond to positions 1-10 of the unmutated, WT $KRAS_{7-16}$ peptide amino acid sequence of SEQ ID NO: 30 with the exception that in SEQ ID NOs: 2 and 33, the glycine at position 6 is substituted with aspartic acid or valine, respectively. In an embodiment of the invention, the TCR has antigenic specificity for a mutated $KRAS_{8-16}$ peptide comprising or consisting of the amino acid sequence of VVGADGVGK (SEQ ID NO: 34) or VVGAVGVGK (SEQ ID NO: 35). The mutated KRAS peptide amino acid sequences of SEQ ID NOs: 34 and 35 generally correspond to positions 1-9 of the unmutated, WT $KRAS_{8-16}$ peptide amino acid sequence of SEQ ID NO: 31 with the exception that in SEQ ID NOs: 34 and 35, the glycine at position 5 is substituted with aspartic acid or valine, respectively. In a preferred embodiment, the TCR has antigenic specificity for a mutated KRAS epitope, the mutated KRAS epitope (a) comprising VVVGADGVGK (SEQ ID NO: 2) or (b) consisting of VVVGAVGVGK (SEQ ID NO: 33) or VVGAVGVGK (SEQ ID NO: 35). In an especially preferred embodiment, the TCR has antigenic specificity for a mutated KRAS epitope comprising VVVGADGVGK (SEQ ID NO: 2). In another preferred embodiment, the TCR has antigenic specificity for a mutated KRAS epitope consisting of VVVGAVGVGK (SEQ ID NO: 33) or VVGAVGVGK (SEQ ID NO: 35). The mutated KRAS amino acid sequences VVVGAVGVGK (SEQ ID NO: 33) and VVGAVGVGK (SEQ ID NO: 35) are also referred to herein as "KRAS G12V." The mutated KRAS amino acid sequences VVVGADGVGK (SEQ ID NO: 2) and VVGADGVGK (SEQ ID NO: 34) are also referred to herein as "KRAS G12D."

The mutated KRAS epitope amino acid sequences described herein are also found in two other mutated oncogenes in human cancer, Neuroblastoma RAS Viral (V-Ras) Oncogene Homolog (NRAS) and Harvey Rat Sarcoma Viral Oncogene Homolog (HRAS). The amino acid sequences of mutated human NRAS and mutated human HRAS contain the mutated human KRAS epitope sequences described herein. Accordingly, in an embodiment of the invention, the inventive TCRs also have antigenic specificity for mutated human NRAS and HRAS. Mutated human KRAS, mutated human NRAS, and mutated human HRAS are collectively referred to herein as "mutated target(s)."

In an embodiment of the invention, the inventive TCRs are able to recognize mutated target, e.g., mutated KRAS, in a major histocompatibility complex (MHC) class I-dependent manner. "MHC class I-dependent manner," as used herein, means that the TCR elicits an immune response upon binding to mutated target, e.g., mutated KRAS, within the context of an MHC class I molecule. The MHC class I molecule can be any MHC class I molecule known in the art, e.g., HLA-A molecules. In a preferred embodiment of the invention, the TCR has antigenic specificity for the mutated epitope, presented in the context of an HLA-A11 molecule.

The TCRs of the invention provide many advantages, including when expressed by cells used for adoptive cell transfer. Mutated KRAS, mutated NRAS, and mutated HRAS are expressed by cancer cells and are not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent one or more of mutated KRAS-positive cancers, mutated NRAS-positive cancers, and mutated HRAS-positive cancers that do not respond to other types of treatment such as, for example, chemotherapy, surgery, or radiation. Additionally, the inventive TCRs may provide highly avid recognition of one or more of mutated KRAS, mutated NRAS, and mutated HRAS, which may provide the ability to recognize unmanipulated tumor cells (e.g., tumor cells that have not been treated with interferon (IFN)-γ, transfected with a vector encoding one or both of mutated KRAS and HLA-A11, pulsed with the mutated $KRAS_{7-16}$ or $KRAS_{8-16}$ peptide, or a combination thereof).

The phrase "antigenic specificity," as used herein, means that the TCR can specifically bind to and immunologically recognize mutated target, e.g., mutated KRAS, with high avidity. For example, a TCR may be considered to have "antigenic specificity" for mutated target if T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative HLA-A11$^+$ target cells pulsed with a low concentration of mutated target peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) antigen-negative HLA-A11$^+$ target cells into which a nucleotide sequence encoding the mutated target has been introduced such that the target cell expresses the mutated target. Cells expressing the inventive TCRs may also secrete IFN-γ upon co-culture with antigen-negative HLA-A11$^+$ target cells pulsed with higher concentrations of mutated target peptide.

Alternatively or additionally, a TCR may be considered to have "antigenic specificity" for a mutated target if T cells expressing the TCR secrete at least twice as much IFN-γ upon co-culture with (a) antigen-negative HLA-A11$^+$ target cells pulsed with a low concentration of mutated target peptide or (b) antigen-negative HLA-A11$^+$ target cells into which a nucleotide sequence encoding the mutated target has been introduced such that the target cell expresses the mutated target as compared to the amount of IFN-γ expressed by a negative control. The negative control may be, for example, (i) T cells expressing the TCR, co-cultured with (a) antigen-negative HLA-A11$^+$ target cells pulsed with the same concentration of an irrelevant peptide (e.g., some other peptide with a different sequence from the mutated target peptide) or (b) antigen-negative HLA-A11$^+$ target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative HLA-A11$^+$ target cells pulsed with the same concentration of mutated target peptide or (b) antigen-negative HLA-A11$^+$ target cells into which a nucleotide sequence encoding the mutated target has been introduced such that the target cell expresses the mutated target. IFN-γ secretion may be measured by methods known in the art such as, for example, enzyme-linked immunosorbent assay (ELISA).

Alternatively or additionally, a TCR may be considered to have "antigenic specificity" for a mutated target if at least twice as many of the numbers of T cells expressing the TCR secrete IFN-γ upon co-culture with (a) antigen-negative HLA-A11$^+$ target cells pulsed with a low concentration of mutated target peptide or (b) antigen-negative HLA-A11+ target cells into which a nucleotide sequence encoding the mutated target has been introduced such that the target cell expresses the mutated target as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for the mutated target, e.g., mutated KRAS.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises: (a) a first polypeptide chain comprising a CDR1 comprising the amino acid sequence of SEQ ID NO: 3 (CDR1 of α chain of anti-KRAS G12D TCR), a CDR2 comprising the amino acid sequence of SEQ ID NO: 4 (CDR2 of α chain of anti-KRAS G12D TCR), and a CDR3 comprising the amino acid sequence of SEQ ID NO: 5 (CDR3 of α chain of anti-KRAS G12D TCR), and a second polypeptide chain comprising a CDR1 comprising the amino acid sequence of SEQ ID NO: 6 (CDR1 of β chain of anti-KRAS G12D TCR), a CDR2 comprising the amino acid sequence of SEQ ID NO: 7 (CDR2 of β chain of anti-KRAS G12D TCR), and a CDR3 comprising the amino acid sequence of SEQ ID NO: 8 (CDR3 of β chain of anti-KRAS G12D TCR); (b) a first polypeptide chain comprising an anti-KRAS G12V TCR α chain CDR1 comprising the amino acid sequence of SEQ ID NO: 125, an anti-KRAS G12V TCR α chain CDR2 comprising the amino acid sequence of SEQ ID NO: 126, an anti-KRAS G12V TCR α chain CDR3 comprising the amino acid sequence of SEQ ID NO: 127, and a second polypeptide chain comprising an anti-KRAS G12V TCR β chain CDR1 comprising the amino acid sequence of SEQ ID NO: 128, an anti-KRAS G12V TCR β chain CDR2 comprising the amino acid sequence of SEQ ID NO: 129, and an anti-KRAS G12V TCR β chain CDR3 comprising the amino acid sequence of SEQ ID NO: 130; (c) a first polypeptide chain comprising an anti-KRAS G12V TCR α chain CDR1 comprising the amino acid sequence of SEQ ID NO: 137, an anti-KRAS G12V TCR α chain CDR2 comprising the amino acid sequence of SEQ ID NO: 138, an anti-KRAS G12V TCR α chain CDR3 comprising the amino acid sequence of SEQ ID NO: 139, and a second polypeptide chain comprising an anti-KRAS G12V TCR β chain CDR1 comprising the amino acid sequence of SEQ ID NO: 140, an anti-KRAS G12V TCR β chain CDR2 comprising the amino acid sequence of SEQ ID NO: 141, and an anti-KRAS G12V TCR β chain CDR3 comprising the amino acid sequence of SEQ ID NO: 142; or (d) first polypeptide chain comprising an anti-KRAS G12D TCR α chain CDR1 comprising the amino acid sequence of SEQ ID NO: 149, an anti-KRAS G12D TCR α chain CDR2 comprising the amino acid sequence of SEQ ID NO: 150, an anti-KRAS G12D TCR α chain CDR3 comprising the amino acid sequence of SEQ ID NO: 151, and a second polypeptide chain comprising an anti-KRAS G12D TCR β chain CDR1 comprising the amino acid sequence of SEQ ID NO: 152, an anti-KRAS G12D TCR β chain CDR2 comprising the amino acid sequence of SEQ ID NO: 153, and an anti-KRAS G12D TCR β chain CDR3 comprising the amino acid sequence of SEQ ID NO: 154. In this regard, the inventive TCR can comprise any one or more of the amino acid sequences selected from the group consisting of SEQ ID NOs: 3-8; 125-130; 137-142; and 149-154. Preferably, the TCR comprises the amino acid sequences of SEQ ID NOs: 3-5; SEQ ID NOs: 6-8; SEQ ID NOs: 125-127; SEQ ID NOs: 128-130; SEQ ID NOs: 137-139; SEQ ID NOs: 140-142; SEQ ID NOs: 149-151; or SEQ ID NOs: 152-154. In an especially preferred embodiment, the TCR comprises the amino acid sequences of (a) all of SEQ ID NOs: 3-8; (b) all of SEQ ID NOs: 125-130; (c) all of SEQ ID NOs: 137-142; (d) all of SEQ ID NOs: 149-154.

In an embodiment of the invention, the TCR comprises an amino acid sequence of a variable region of a TCR comprising the CDRs set forth above. In this regard, the TCR can comprise the amino acid sequence of SEQ ID NO: 9 (variable region of anti-KRAS G12D TCR α chain); SEQ ID NO: 10 (variable region of anti-KRAS G12D TCR β chain); both SEQ ID NOs: 9 and 10; SEQ ID NO: 131 (variable region of anti-KRAS G12V TCR α chain); SEQ ID NO: 132 (variable region of anti-KRAS G12V TCR β chain); both SEQ ID NOs: 131 and 132; SEQ ID NO: 143 (variable region of anti-KRAS G12V TCR α chain); SEQ ID NO: 144 (variable region of anti-KRAS G12V TCR β chain); both SEQ ID NOs: 143 and 144; SEQ ID NO: 155 (variable region of anti-KRAS G12D TCR α chain); SEQ ID NO: 156 (variable region of anti-KRAS G12D TCR β chain); or both SEQ ID NOs: 155 and 156. Preferably, the inventive TCR comprises the amino acid sequences of both SEQ ID NOs: 9 and 10; both SEQ ID NOs: 131 and 132; both SEQ ID NOs: 143 and 144; or both SEQ ID NOs: 155 and 156.

In an embodiment of the invention, the TCR further comprises an amino acid sequence of a constant region of a TCR. In this regard, the TCR can comprise the amino acid sequence of SEQ ID NO: 13 (constant region of anti-KRAS G12D TCR α chain), SEQ ID NO: 14 (constant region of anti-KRAS G12D TCR β chain), both SEQ ID NOs: 13 and 14; SEQ ID NO: 135 (constant region of anti-KRAS G12V TCR α chain), SEQ ID NO: 136 (constant region of anti-KRAS G12V TCR β chain), both SEQ ID NOs: 135 and 136; SEQ ID NO: 147 (constant region of anti-KRAS G12V TCR α chain), SEQ ID NO: 148 (constant region of anti-KRAS G12V TCR β chain), both SEQ ID NOs: 147 and 148; SEQ ID NO: 159 (constant region of anti-KRAS G12D TCR α chain), SEQ ID NO: 160 (constant region of anti-KRAS G12D TCR β chain), or both SEQ ID NOs: 159 and 160. Preferably, the inventive TCR comprises the amino acid sequences of both SEQ ID NOs: 13 and 14; both SEQ ID NOs: 135 and 136; both SEQ ID NOs: 147 and 148; both SEQ ID NOs: 159 and 160.

In an embodiment of the invention, the inventive TCR may comprise a combination of a variable region and a constant region. In this regard, the TCR can comprise: (a) an α chain comprising the amino acid sequences of both SEQ ID NO: 9 (variable region of α chain) and SEQ ID NO: 13 (constant region of α chain); a β chain comprising the amino acid sequences of both SEQ ID NO: 10 (variable region of β chain) and SEQ ID NO: 14 (constant region of β chain); or the amino acid sequences of all of SEQ ID NOs: 9, 10, 13, and 14; (b) an α chain comprising the amino acid sequences of both SEQ ID NO: 131 (variable region of α chain) and SEQ ID NO: 135 (constant region of α chain); a β chain comprising the amino acid sequences of both SEQ ID NO: 132 (variable region of β chain) and SEQ ID NO: 136 (constant region of β chain); or the amino acid sequences of all of SEQ ID NOs: 131, 132, 135, and 136; (c) an α chain comprising the amino acid sequences of both SEQ ID NO: 143 (variable region of α chain) and SEQ ID NO: 147 (constant region of α chain); a β chain comprising the amino acid sequences of both SEQ ID NO: 144 (variable region of β chain) and SEQ ID NO: 148 (constant region of β chain); or the amino acid sequences of all of SEQ ID NOs: 143, 144, 147, and 148; or (d) an α chain comprising the amino acid sequences of both SEQ ID NO: 155 (variable region of α chain) and SEQ ID NO: 159 (constant region of α chain); a β chain comprising the amino acid sequences of both SEQ ID NO: 156 (variable region of β chain) and SEQ ID NO: 160 (constant region of β chain); or the amino acid sequences of all of SEQ ID NOs: 155, 156, 159, and 160. Preferably, the inventive TCR comprises the amino acid sequences of (a) all of SEQ ID NOs: 9, 10, 13, and 14; (b) all of SEQ ID NOs: 131, 132, 135, and 136; (c) all of SEQ ID NOs: 143, 144, 147, and 148; or (d) all of SEQ ID NOs: 155, 156, 159, and 160.

In an embodiment of the invention, the inventive TCR may comprise a combination of any of the CDR regions described herein and a constant region. In this regard, the TCR can comprise an α chain comprising: (a) the amino acid sequences of all of SEQ ID NOs: 3-5 and 13; a β chain comprising the amino acid sequences of all of SEQ ID NOs: 6-8 and 14; or the amino acid sequences of all of SEQ ID NOs: 3-8 and 13-14; (b) the amino acid sequences of all of SEQ ID NOs: 125-127 and 135; a β chain comprising the amino acid sequences of all of SEQ ID NOs: 128-130 and 136; or the amino acid sequences of all of SEQ ID NOs: 125-130 and 135-136; (c) the amino acid sequences of all of SEQ ID NOs: 137-139 and 147; a β chain comprising the amino acid sequences of all of SEQ ID NOs: 140-142 and 148; or the amino acid sequences of all of SEQ ID NOs: 137-142 and 147-148; or (d) the amino acid sequences of all of SEQ ID NOs: 149-151 and 159; a β chain comprising the amino acid sequences of all of SEQ ID NOs: 152-154 and 160; or the amino acid sequences of all of SEQ ID NOs: 149-154 and 159-160.

In an embodiment of the invention, the inventive TCR can comprise an α chain of a TCR and a β chain of a TCR. Each of the α chain and β chain of the inventive TCR can independently comprise any amino acid sequence. In this regard, the α chain of the inventive TCR can comprise the amino acid sequence of SEQ ID NO: 11 (anti-KRAS G12D TCR α chain), SEQ ID NO: 133 (anti-KRAS G12V TCR α chain), SEQ ID NO: 145 (anti-KRAS G12V TCR α chain), or SEQ ID NO: 157 (anti-KRAS G12D TCR α chain). An α chain of this type can be paired with any β chain of a TCR. In this regard, the β chain of the inventive TCR can comprise the amino acid sequence of SEQ ID NO: 12 (anti-KRAS G12D TCR β chain), SEQ ID NO: 134 (anti-KRAS G12V TCR β chain), SEQ ID NO: 146 (anti-KRAS G12V TCR β chain), or SEQ ID NO: 158 (anti-KRAS G12D TCR β chain). The inventive TCR, therefore, can comprise the amino acid sequence of SEQ ID NO: 11, SEQ ID NO: 12, SEQ ID NO: 133, SEQ ID NO: 134, SEQ ID NO: 145, SEQ ID NO: 146, SEQ ID NO: 157, SEQ ID NO: 158, both SEQ ID NOs: 11 and 12, both SEQ ID NOs: 133 and 134, both SEQ ID NOs: 145 and 146, or both SEQ ID NOs: 157 and 158. Preferably, the inventive TCR comprises the amino acid sequences of both SEQ ID NOs: 11 and 12, both SEQ ID NOs: 133 and 134, both SEQ ID NOs: 145 and 146, or both SEQ ID NOs: 157 and 158.

In an embodiment of the invention, the inventive TCRs recognize mutated target, e.g., mutated KRAS, either (i) in the presence of CD4 and the absence of CD8 or (ii) in the presence of CD8 and the absence of CD4. In a preferred embodiment, a TCR comprising the amino acid sequences of (i) SEQ ID NOs: 125-130; (ii) SEQ ID NOs: 131-132; or (iii) SEQ ID NOs: 133 and 134 recognizes mutated target, e.g., mutated KRAS, either (i) in the presence of CD4 and the absence of CD8 or (ii) in the presence of CD8 and the absence of CD4. Accordingly, these inventive TCRs may advantageously recognize mutated target, e.g., mutated KRAS, when expressed by either CD4+ or CD8+ cells.

In an embodiment of the invention, the TCR is a murine TCR. As used herein, the term "murine," when referring to a TCR or any component of a TCR described herein (e.g., complementarity determining region (CDR), variable region, constant region, α chain, and/or β chain), means a TCR (or component thereof) which is derived from a mouse, i.e., a TCR (or component thereof) that originated from or was, at one time, expressed by a mouse T cell. In an embodiment of the invention, a TCR comprising (i) all of SEQ ID NOs: 3-8; (ii) SEQ ID NOs: 9 and 10; (iii) SEQ ID NOs: 11 and 12; (iv) all of SEQ ID NOs: 3-8 and 13-14; (v) all of SEQ ID NOs: 9, 10, 13, and 14; (vi) all of SEQ ID NOs: 125-130; (vii) SEQ ID NOs: 131 and 132; (viii) SEQ ID NOs: 133 and 134; (ix) all of SEQ ID NOs: 125-130 and 135-136; (x) all of SEQ ID NOs: 131, 132, 135, and 136; (xi) all of SEQ ID NOs: 137-142; (xii) SEQ ID NOs: 143 and 144; (xiii) SEQ ID NOs: 145 and 146; (xiv) all of SEQ ID NOs: 137-142 and 147-148; (xv) all of SEQ ID NOs: 143, 144, 147, and 148; (xvi) all of SEQ ID NOs: 149-154; (xvii) SEQ ID NOs: 155 and 156; (xviii) SEQ ID NOs: 157 and 158; (xix) all of SEQ ID NOs: 149-154 and 159-160; or (xx) all of SEQ ID NOs: 155, 156, 159, and 160 is a murine TCR.

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated target, e.g., mutated KRAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein. In an embodiment of the invention, the functional variant is a substituted TCR, polypeptide, or protein comprising (i) the substituted CDR3α, variable region of the α chain, or full-length α chain amino acid sequence of any one of SEQ ID NOs: 46-56 and 207, 70-80 and 208, and 94-104 and 209, respectively; (ii) the substituted CDR3β, variable region of the β chain, or full-length β chain amino acid sequence of any one of SEQ ID NOs: 57-69, 81-93, and 105-117, respectively; or (iii) a pair of any one of the amino acid sequences of (i) in combination with any one of the amino acid sequences of (ii).

For example, in an embodiment of the invention, a substituted TCR, polypeptide, or protein may comprise one or both of (a) a substituted CDR3α amino acid sequence of any one of SEQ ID NOs: 46-56 and 207 (Table I) and (b) a substituted CDR3β amino acid sequence of any one of SEQ ID NOs: 57-69 (Table II). An embodiment of the invention provides a TCR, polypeptide, or protein having any one or more of the native, unsubstituted CDR1α, CDR2α, CDR1β, CDR2β, and CDR3β amino acid sequences described herein with respect to other aspects of the invention in combination with any one of the substituted CDR3α amino acid sequences of SEQ ID NOs: 46-56 and 207. In this regard, an embodiment of the invention provides a substituted TCR comprising the amino acid sequences of all of SEQ ID NOs: 149-150, 207, and 152-154. Another embodiment of the invention provides a TCR, polypeptide, or protein having any one or more of the native, unsubstituted CDR1α, CDR2α, CDR3α, CDR1β, and CDR2β amino acid sequences described herein with respect to other aspects of the invention in combination with any one of the substituted CDR3β amino acid sequences of SEQ ID NOs: 57-69.

TABLE I

| | |
|---|---|
| Substituted CDR3 α-version 1 | CXLRGNAGAKLTF<br>Wherein X is arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 46) |
| Substituted CDR3 α-version 2 | CAXRGNAGAKLTF<br>Wherein X is alanine, arginine, asparagine, aspartic acid, cysteine, glutamic acid, glutamine, glycine, histidine, isoleucine, lysine, methionine, phenylalanine, proline, serine, threonine, tryptophan, tyrosine, or valine (SEQ ID NO: 47) |
| Substituted CDR3 α-version 3 | CALXGNAGAKLTF<br>Wherein X is alanine, asparagine, aspartic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 48) |
| Substituted CDR3 α-version 4 | CALRXNAGAKLTF<br>Wherein X is alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine (SEQ ID NO: 49) |
| Substituted CDR3 α-version 5 | CALRGXAGAKLTF<br>Wherein X is alanine, arginine, aspartic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 50) |
| Substituted CDR3 α-version 6 | CALRGNXGAKLTF<br>Wherein X is arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 51) |
| Substituted CDR3 α-version 7 | CALRGNAXAKLTF<br>Wherein X is alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine (SEQ ID NO: 52) |
| Substituted CDR3 α-version 8 | CALRGNAGXKLTF<br>Wherein X is arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 53) |
| Substituted CDR3 α-version 9 | CALRGNAGAXLTF<br>Wherein X is alanine, arginine, asparagine, aspartic acid, cysteine, glutamic acid, glutamine, glycine, histidine, isoleucine, leucine, methionine, phenylalanine, proline, serine, threonine, tryptophan, tyrosine, or valine (SEQ ID NO: 54) |
| Substituted CDR3 α-version 10 | CALRGNAGAKXTF<br>Wherein X is alanine, arginine, asparagine, aspartic acid, cysteine, glutamic acid, glutamine, histidine, isoleucine, lysine, methionine, phenylalanine, proline, serine, threonine, tryptophan, tyrosine, or valine (SEQ ID NO: 55) |
| Substituted CDR3 α-version 11 | CALRGNAGAKLXF<br>Wherein X is alanine, arginine, asparagine, aspartic acid, cysteine, glutamic acid, glutamine, glycine, histidine, isoleucine, leucine, lysine, methionine, phenylalanine, proline, serine, tryptophan, tyrosine, or valine (SEQ ID NO: 56) |
| Substituted CDR3 α-version 12 | CAADSSNTXYQNFYF<br>Wherein X is alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine (SEQ ID NO: 207).<br>In a preferred embodiment, X ia alanine in SEQ ID NO: 207. |

TABLE II

| | | |
|---|---|---|
| Substituted CDR3 β-version 1 | CXSSSRDWSAETLYF<br>Wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 57) | |
| Substituted CDR3 β-version 2 | CAXSSRDWSAETLYF<br>Wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine (SEQ ID NO: 58) | |
| Substituted CDR3 β-version 3 | CASXSRDWSAETLYF<br>Wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine (SEQ ID NO: 59) | |
| Substituted CDR3 β-version 4 | CASSXRDWSAETLYF<br>Wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine (SEQ ID NO: 60) | |
| Substituted CDR3 β-version 5 | CASSSXDWSAETLYF<br>Wherein X is alanine, asparagine, asparatic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 61) | |
| Substituted CDR3 β-version 6 | CASSSRXWSAETLYF<br>Wherein X is alanine, arginine, asparagine, cysteine, glutamic acid, glutamine, glycine, histidine, isoleucine, leucine, lysine, methionine, phenylalanine, proline, serine, threonine, tryptophan, tyrosine, or valine (SEQ ID NO: 62) | |
| Substituted CDR3 β-version 7 | CASSSRDXSAETLYF<br>Wherein X is alanine, arginine, asparagine, asparatic acid, cysteine, glutamic acid, glutamine, glycine, histidine, isoleucine, leucine, lysine, methionine, phenylalanine, proline, serine, threonine, tyrosine, or valine (SEQ ID NO: 63) | |
| Substituted CDR3 β-version 8 | CASSSRDWXAETLYF<br>Wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine (SEQ ID NO: 64) | |
| Substituted CDR3 β-version 9 | CASSSRDWSXETLYF<br>Wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine (SEQ ID NO: 65) | |
| Substituted CDR3 β-version 10 | CASSSRDWSAXTLYF<br>Wherein X is alanine, arginine, asparagine, asparatic acid, cysteine, glutamine, glycine, histidine, isoleucine, leucine, lysine, methionine, phenylalanine, proline, serine, threonine, tryptophan, tyrosine, or valine (SEQ ID NO: 66) | |
| Substituted CDR3 β-version 11 | CASSSRDWSAEXLYF<br>Wherein X is alanine, arginine, asparagine, asparatic acid, cysteine, glutamic acid, glutamine, glycine, histidine, isoleucine, leucine, lysine, methionine, phenylalanine, proline, serine, tryptophan, tyrosine, or valine (SEQ ID NO: 67) | |
| Substituted CDR3 β-version 12 | CASSSRDWSAETXYF<br>Wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine (SEQ ID NO: 68) | |
| Substituted CDR β-version 13 | CASSSRDWSAETLXF<br>Wherein X is alanine, arginine, asparagine, asparatic acid, cysteine, glutamic acid, glutamine, glycine, histidine, isoleucine, leucine, lysine, methionine, phenylalanine, proline, serine, threonine, tryptophan, or valine (SEQ ID NO: 69) | |

In an embodiment of the invention, each of the substituted CDR3α amino acid sequences of SEQ ID NOs: 46-56 does not comprise the native, unsubstituted CDR3α amino acid sequence of SEQ ID NO: 5. In an embodiment of the invention, the substituted CDR3α amino acid sequence of SEQ ID NO: 207 does not comprise the native, unsubstituted CDR3α amino acid sequence of SEQ ID NO: 151. Similarly, in an embodiment of the invention, each of the substituted CDR3β amino acid sequences of SEQ ID NOs: 57-69 does not comprise the native, unsubstituted CDR3β amino acid sequence of SEQ ID NO: 8.

An embodiment of the invention provides a substituted TCR, polypeptide, or protein comprising one or both of (i) a substituted variable region of an α chain comprising the amino acid sequence of any one of SEQ ID NOs: 70-80 and 208 (Table III) and (ii) a substituted variable region of a β chain comprising the amino acid sequence of any one of SEQ ID NOs: 81-93 (Table IV). An embodiment of the invention provides a TCR, polypeptide, or protein having any of the native, unsubstituted variable regions of the β chain described herein with respect to other aspects of the invention in combination with any one of the substituted variable region α chain amino acid sequences of SEQ ID NOs: 70-80 and 208. Another embodiment of the invention provides a TCR, polypeptide, or protein having any of the native, unsubstituted variable regions of the α chain described herein with respect to other aspects of the invention in combination with any one of the substituted variable region β chain amino acid sequences of SEQ ID NOs: 81-93.

TABLE III

| | |
|---|---|
| Substituted variable region α-version 1 | SEQ ID NO: 70, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region α-version 2 | SEQ ID NO: 71, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |
| Substituted variable region α-version 3 | SEQ ID NO: 72, wherein X is alanine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region α-version 4 | SEQ ID NO: 73, wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine |
| Substituted variable region α-version 5 | SEQ ID NO: 74, wherein X is alanine, arginine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region α-version 6 | SEQ ID NO: 75, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region α-version 7 | SEQ ID NO: 76, wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine |
| Substituted variable region α-version 8 | SEQ ID NO: 77, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region α-version 9 | SEQ ID NO: 78, wherein X is alanine, arginine, asparagine, asparatic acid, cysteine, glutamic acid, glutamine, glycine, histidine, isoleucine, leucine, methionine, phenylalanine, proline, serine, threonine, tryptophan, tyrosine, or valine |
| Substituted variable region α-version 10 | SEQ ID NO: 79, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |
| Substituted variable region α-version 11 | SEQ ID NO: 80, wherein X is alanine, arginine, asparagine, asparatic acid, cysteine, glutamic acid, glutamine, glycine, histidine, isoleucine, leucine, lysine, methionine, phenylalanine, proline, serine, tryptophan, tyrosine, or valine |
| Substituted variable region α-version 12 | SEQ ID NO: 208, Wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine. In a preferred embodiment, X is alanine in SEQ ID NO: 208. |

TABLE IV

| | |
|---|---|
| Substituted variable region β-version 1 | SEQ ID NO: 81, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region β-version 2 | SEQ ID NO: 82, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted variable region β-version 3 | SEQ ID NO: 83, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted variable region β-version 4 | SEQ ID NO: 84, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted variable region β-version 5 | SEQ ID NO: 85, wherein X is alanine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region β-version 6 | SEQ ID NO: 86, wherein X is alanine, arginine, asparagine, cysteine, glutamic acid, glutamine, glycine, histidine, isoleucine, leucine, lysine, methionine, phenylalanine, proline, serine, threonine, tryptophan, tyrosine, or valine |
| Substituted variable region β-version 7 | SEQ ID NO: 87, wherein X is alanine, arginine, asparagine, asparatic acid, cysteine, glutamic acid, glutamine, glycine, histidine, isoleucine, leucine, lysine, methionine, phenylalanine, proline, serine, threonine, tyrosine, or valine |
| Substituted variable region β-version 8 | SEQ ID NO: 88, wherein X is alanine, arginine, asparagine, asparatic acid, cysteine, glutamic acid, glutamne, glycine, histidine, isoleucine, leucine, lysine, methionine, phenylalanine, proline, threonine, tryptophan, tyrosine, or valine |
| Substituted variable region β-version 9 | SEQ ID NO: 89, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted variable region β-version 10 | SEQ ID NO: 90, wherein X is alanine, arginine, asparagine, asparatic acid, cysteine, glutamine, glycine, histidine, isoleucine, leucine, lysine, methionine, phenylalanine, proline, serine, threonine, tryptophan, tyrosine, or valine |
| Substituted variable region β-version 11 | SEQ ID NO: 91, wherein X is alanine, arginine, asparagine, asparatic acid, cysteine, glutamic acid, glutamine, glycine, histidine, isoleucine, leucine, lysine, methionine, phenylalanine, proline, serine, tryptophan, tyrosine, or valine |
| Substituted variable region β-version 12 | SEQ ID NO: 92, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |
| Substituted variable region β-version 13 | SEQ ID NO: 93, wherein X is alanine, arginine, asparagine, asparatic acid, cysteine, glutamic acid, glutamine, glycine, histidine, isoleucine, leucine, lysine, methionine, phenylalanine, proline, serine, threonine, tryptophan, or valine |

In an embodiment of the invention, each of the substituted variable region α chain amino acid sequences of SEQ ID NOs: 70-80 does not comprise the native, unsubstituted variable region α chain amino acid sequence of SEQ ID NO: 9. In an embodiment of the invention, the substituted variable region α chain amino acid sequence of SEQ ID NO: 208 does not comprise the native, unsubstituted variable region α chain amino acid sequence of SEQ ID NO: 155. Similarly, in an embodiment of the invention, each of the substituted variable region β chain amino acid sequences of SEQ ID NOs: 81-93 does not comprise the native, unsubstituted variable region β chain amino acid sequence of SEQ ID NO: 10.

An embodiment of the invention provides a substituted TCR, polypeptide, or protein comprising one or both of (i) a substituted full length α chain comprising the amino acid sequence of any one of SEQ ID NOs: 94-104 and 209 (Table V) and (ii) a substituted full length β chain comprising the amino acid sequence of any one of SEQ ID NOs: 105-117 (Table VI). An embodiment of the invention provides a TCR, polypeptide, or protein having any of the native, unsubstituted full-length β chain sequences described herein with respect to other aspects of the invention in combination with any one of the substituted full length α chain amino acid sequences of SEQ ID NOs: 94-104 and 209. Another embodiment of the invention provides a TCR, polypeptide, or protein having any of the native, unsubstituted full-length α chains described herein with respect to other aspects of the invention in combination with any one of the substituted full-length β chain sequences of SEQ ID NOs: 105-117.

TABLE V

| | |
|---|---|
| Substituted full length α chain-version 1 | SEQ ID NO: 94, wherein X is arginine, glutamic asparagine, asparatic acid, cysteine, acid, glutamine, glycine, histidine, isoleucine, leucine, lysine, methionine, phenylalanine, proline, serine, threonine, tryptophan, tyrosine, or valine |
| Substituted full length α chain-version 2 | SEQ ID NO: 95, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |
| Substituted full length α chain-version 3 | SEQ ID NO: 96, wherein X is alanine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length α chain-version 4 | SEQ ID NO: 97, wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine |
| Substituted full length α chain-version 5 | SEQ ID NO: 98, wherein X is alanine, arginine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length α chain-version 6 | SEQ ID NO: 99, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length α chain-version 7 | SEQ ID NO: 100, wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine |
| Substituted full length α chain-version 8 | SEQ ID NO: 101, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length α chain-version 9 | SEQ ID NO: 102, wherein X is alanine, arginine, asparagine, asparatic acid, cysteine, glutamic acid, glutamine, glycine, histidine, isoleucine, leucine, methionine, phenylalanine, proline, serine, threonine, tryptophan, tyrosine, or valine |
| Substituted full length α chain-version 10 | SEQ ID NO: 103, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |

TABLE V-continued

| | |
|---|---|
| Substituted full length α chain-version 11 | SEQ ID NO: 104, wherein X is alanine, arginine, asparagine, asparatic acid, cysteine, glutamic acid, glutamine, glycine, histidine, isoleucine, leucine, lysine, methionine, phenylalanine, proline, serine, tryptophan, tyrosine, or valine |
| Substituted full length α chain-version 12 | SEQ ID NO: 209, Wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine. In a preferred embodiment, X is alanine in SEQ ID NO: 209. |

TABLE VI

| | |
|---|---|
| Substituted full length β chain-version 1 | SEQ ID NO: 105, wherein X is arginine, asparagine, asparatic acid, cysteine,glutamic acid, glutamine, glycine, histidine, isoleucine, leucine, lysine, methionine, phenylalanine, proline, serine, threonine, tryptophan, tyrosine, or valine |
| Substituted full length β chain-version 2 | SEQ ID NO: 106, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted full length β chain-version 3 | SEQ ID NO: 107, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted full length β chain-version 4 | SEQ ID NO: 108, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted full length β chain-version 5 | SEQ ID NO: 109, wherein X is alanine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length β chain-version 6 | SEQ ID NO: 110, wherein X is alanine, arginine, asparagine, cysteine, glutamic acid, glutamine, glycine, histidine, isoleucine, leucine, lysine, methionine, phenylalanine, proline, serine, threonine, tryptophan, tyrosine, or valine |
| Substituted full length β chain-version 7 | SEQ ID NO: 111, wherein X is alanine, arginine, asparagine, asparatic acid, cysteine, glutamic acid, glutamine, glycine, histidine, isoleucine, leucine, lysine, methionine, phenylalanine, proline, serine, threonine, tyrosine, or valine |
| Substituted full length β chain-version 8 | SEQ ID NO: 112, wherein X is alanine, arginine, asparagine, asparatic acid, cysteine, glutamic acid, glutamine, glycine, histidine, isoleucine, leucine, lysine, methionine, phenylalanine, proline, threonine, tryptophan, tyrosine, or valine |
| Substituted full length β chain-version 9 | SEQ ID NO: 113, wherein X is arginine, asparagine, asparatic acid, cysteine, glutamic acid, glutamine, glycine, histidine, isoleucine, leucine, lysine, methionine, phenylalanine, proline, serine, threonine, tryptophan, tyrosine, or valine |
| Substituted full length β chain-version 10 | SEQ ID NO: 114, wherein X is alanine, arginine, asparagine, asparatic acid, cysteine, glutamine, glycine, histidine, isoleucine, leucine, lysine, methionine, phenylalanine, proline, serine, threonine, tryptophan, tyrosine, or valine |
| Substituted full length β chain-version 11 | SEQ ID NO: 115, wherein X is alanine, arginine, asparagine, asparatic acid, cysteine, glutamic acid, glutamine, glycine, histidine, isoleucine, leucine, lysine, methionine, phenylalanine, proline, serine, tryptophan, tyrosine, or valine |
| Substituted full length β chain-version 12 | SEQ ID NO: 116, wherein X is alanine, arginine, asparagine, asparatic acid, cysteine, glutamic acid, glutamine, glycine, histidine, isoleucine, lysine, methionine, phenylalanine, proline, serine, threonine, tryptophan, tyrosine, or valine |

TABLE VI-continued

| | |
|---|---|
| Substituted full length β chain-version 13 | SEQ ID NO: 117, wherein X is alanine, arginine, asparagine, aspartic acid, cysteine, glutamic acid, glutamine, glycine, histidine, isoleucine, leucine, lysine, methionine, phenylalanine, proline, serine, threonine, tryptophan, or valine |

In an embodiment of the invention, each of the substituted full length α chain amino acid sequences of SEQ ID NOs: 94-104 does not comprise the native, unsubstituted full length α chain amino acid sequence of SEQ ID NO: 11. In an embodiment of the invention, the substituted full length α chain amino acid sequence of SEQ ID NO: 209 does not comprise the native, unsubstituted full length α chain amino acid sequence of SEQ ID NO: 157. Similarly, in an embodiment of the invention, each of the substituted full length β chain amino acid sequences of SEQ ID NOs: 105-117 does not comprise the native, unsubstituted full length β chain amino acid sequence of SEQ ID NO: 12.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 11, SEQ ID NO: 12, SEQ ID NO: 133, SEQ ID NO: 134, SEQ ID NO: 145, SEQ ID NO: 146, SEQ ID NO: 157, SEQ ID NO: 158, SEQ ID NO: 209, both SEQ ID NOs: 11 and 12, both SEQ ID NOs: 133 and 134, both SEQ ID NOs: 145 and 146, both SEQ ID NO: 157 and 158, or both SEQ ID NOs: 158 and 209. Also, for instance, the inventive TCRs, polypeptides, or proteins can consist essentially of the amino acid sequence(s) of SEQ ID NO: 9, SEQ ID NO: 10, SEQ ID NO: 131, SEQ ID NO: 132, SEQ ID NO: 143, SEQ ID NO: 144, SEQ ID NO: 155, SEQ ID NO: 156, SEQ ID NO: 208, both SEQ ID NOs: 9 and 10, both SEQ ID NOs: 131 and 132, both SEQ ID NO: 143 and 144, both SEQ ID NOs: 155 and 156, or both SEQ ID NOs: 156 and 208. Furthermore, the inventive TCRs, polypeptides, or proteins can consist essentially of the amino acid sequence of (a) SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or any combination thereof, e.g., SEQ ID NOs: 3-5; 6-8; or 3-8; (b) SEQ ID NO: 125 (CDR1 of α chain), SEQ ID NO: 126 (CDR2 of α chain), SEQ ID NO: 127 (CDR3 of α chain), SEQ ID NO: 128 (CDR1 of β chain), SEQ ID NO: 129 (CDR2 of β chain), SEQ ID NO: 130 (CDR3 of β chain), or any combination thereof, e.g., SEQ ID NOs: 125-127; 128-130; or 125-130; (c) SEQ ID NO: 137 (CDR1 of α chain), SEQ ID NO: 138 (CDR2 of α chain), SEQ ID NO: 139 (CDR3 of α chain), SEQ ID NO: 140 (CDR1 of β chain), SEQ ID NO: 141 (CDR2 of β chain), SEQ ID NO: 142 (CDR3 of β chain), or any combination thereof, e.g., SEQ ID NOs: 137-139; 140-142; or 137-142; (d) SEQ ID NO: 149 (CDR1 of α chain), SEQ ID NO: 150 (CDR2 of α chain), SEQ ID NO: 151 (CDR3 of α chain), SEQ ID NO: 152 (CDR1 of β chain), SEQ ID NO: 153 (CDR2 of β chain), SEQ ID NO: 154 (CDR3 of β chain), or any combination thereof, e.g., SEQ ID NOs: 149-151; 152-154; or 149-154; or (e) SEQ ID NO: 149 (CDR1 of α chain), SEQ ID NO: 150 (CDR2 of α chain), SEQ ID NO: 207 (substituted CDR3 of α chain), SEQ ID NO: 152 (CDR1 of β chain), SEQ ID NO: 153 (CDR2 of β chain), SEQ ID NO: 154 (CDR3 of β chain), or any combination thereof, e.g., SEQ ID NOs: 149-150 and 207; 152-154; or 149-150, 207, and 152-154.

Also provided by the invention is a polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated target, e.g., mutated KRAS. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to mutated target, e.g., mutated KRAS (e.g., in an HLA-A11-dependent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated target, e.g., mutated KRAS; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In an embodiment of the invention, the polypeptide can comprise a functional portion comprising the amino acid sequence of (a) SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof; (b) SEQ ID NO: 125 (CDR1 of α chain), 126 (CDR2 of α chain), 127 (CDR3 of α chain), 128 (CDR1 of β chain), 129 (CDR2 of β chain), 130 (CDR3 of β chain), or a combination thereof; (c) SEQ ID NO: 137 (CDR1 of α chain), 138 (CDR2 of α chain), 139 (CDR3 of α chain), 140 (CDR1 of β chain), 141 (CDR2 of β chain), 142 (CDR3 of β chain), or a combination thereof; (d) SEQ ID NO: 149 (CDR1 of α chain), 150 (CDR2 of α chain), 151 (CDR3 of α chain), 152 (CDR1 of β chain), 153 (CDR2 of β chain), 154 (CDR3 of β chain), or a combination thereof; or (e) SEQ ID NO: 149 (CDR1 of α chain), 150 (CDR2 of α chain), 207 (substituted CDR3 of α chain), 152 (CDR1 of β chain), 153 (CDR2 of β chain), 154 (CDR3 of β chain), or a combination thereof. Preferably, the inventive polypeptide comprises a functional portion comprising the amino acid sequences of SEQ ID NOs: 3-5; 6-8; 125-127; 128-130; 137-139; 140-142; 149-151; 152-154; all of SEQ ID NOs: 3-8; all of SEQ ID NOs: 125-130; all of SEQ ID NOs: 137-142; all of SEQ ID NOs: 149-154; or all of SEQ ID NOs: 149-150, 207, and 152-154. More preferably, the polypeptide comprises a functional portion comprising the amino acid sequences of all of SEQ ID NOs: 3-8; all of SEQ ID NOs: 125-130; all of SEQ ID NOs: 137-142; all of SEQ ID NOs: 149-154; or all of SEQ ID NOs: 149-150, 207, and 152-154.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 (variable region of α chain), SEQ ID NO: 10 (variable region of β chain), SEQ ID NO: 131 (variable region of α chain), SEQ ID NO: 132 (variable region of β chain), SEQ ID NO: 143 (variable region of α chain), SEQ ID NO: 144 (variable region of β chain), SEQ ID NO: 155 (variable region of α chain), SEQ ID NO: 156 (variable region of β chain), SEQ ID NO: 208 (substituted variable region of α chain), both SEQ ID NOs: 9 and 10, both SEQ ID NOs: 131 and 132, both SEQ ID NOs: 143 and 144, both SEQ ID NO: 155 and 156, or both SEQ ID NOs: 208 and 156. Preferably, the polypeptide comprises the amino acid sequences of both SEQ ID NOs: 9 and 10, both SEQ ID NOs: 131 and 132, both SEQ ID NOs: 143 and 144, both SEQ ID NO: 155 and 156, or both SEQ ID NOs: 208 and 156.

In an embodiment of the invention, the inventive polypeptide can further comprise the constant region of the inventive TCR or functional variant thereof set forth above. In this regard, the polypeptide can comprise the amino acid sequence of SEQ ID NO: 13 (constant region of α chain), SEQ ID NO: 14 (constant region of β chain), SEQ ID NO: 135 (constant region of α chain), SEQ ID NO: 136 (constant region of β chain), SEQ ID NO: 147 (constant region of α chain), SEQ ID NO: 148 (constant region of β chain), SEQ ID NO: 159 (constant region of α chain), SEQ ID NO: 160 (constant region of β chain), both SEQ ID NOs: 13 and 14, both SEQ ID NOs: 135 and 136, both SEQ ID NOs: 147 and 148, or both SEQ ID NOs: 159 and 160. Preferably, the polypeptide comprises the amino acid sequences of both SEQ ID NOs: 13 and 14, both SEQ ID NOs: 135 and 136, both SEQ ID NOs: 147 and 148, or both SEQ ID NOs: 159 and 160.

In an embodiment of the invention, the inventive polypeptide may comprise a combination of a variable region and a constant region of the inventive TCR or functional variant thereof. In this regard, the polypeptide can comprise: (a) the amino acid sequences of both SEQ ID NO: 9 (variable region of α chain) and SEQ ID NO: 13 (constant region of α chain), both SEQ ID NO: 10 (variable region of β chain) and SEQ ID NO: 14 (constant region of β chain), or all of SEQ ID NOs: 9, 10, 13, and 14; (b) the amino acid sequences of both SEQ ID NO: 131 (variable region of α chain) and SEQ ID NO: 135 (constant region of α chain), both SEQ ID NO: 132 (variable region of β chain) and SEQ ID NO: 136 (constant region of β chain), or all of SEQ ID NOs: 131, 132, 135, and 136; (c) the amino acid sequences of both SEQ ID NO: 143 (variable region of α chain) and SEQ ID NO: 147 (constant region of α chain), both SEQ ID NO: 144 (variable region of β chain) and SEQ ID NO: 148 (constant region of β chain), or all of SEQ ID NOs: 143, 144, 147, and 148; (d) the amino acid sequences of both SEQ ID NO: 155 (variable region of α chain) and SEQ ID NO: 159 (constant region of α chain), both SEQ ID NO: 156 (variable region of β chain) and SEQ ID NO: 160 (constant region of β chain), or all of SEQ ID NOs: 155, 156, 159, and 160; or (e) the amino acid sequences of both SEQ ID NO: 208 (substituted variable region of α chain) and SEQ ID NO: 159 (constant region of α chain), both SEQ ID NO: 156 (variable region of β chain) and SEQ ID NO: 160 (constant region of β chain), or all of SEQ ID NOs: 208, 156, 159, and 160. Preferably, the polypeptide comprises the amino acid sequences of all of SEQ ID NOs: 9, 10, 13, and 14; all of SEQ ID NOs: 131, 132, 135, and 136; all of SEQ ID NOs: 143, 144, 147, and 148; all of SEQ ID NOs: 155, 156, 159, and 160; or all of SEQ ID NOs: 208, 156, 159, and 160.

In an embodiment of the invention, the inventive polypeptide may comprise a combination of any of the CDR regions described herein and a constant region of the inventive TCR. In this regard, the polypeptide can comprise the amino acid sequences of all of SEQ ID NOs: 3-5 and 13, all of SEQ ID NOs: 6-8 and 14, all of SEQ ID NOs: 3-8 and 13-14; all of SEQ ID NOs: 125-127 and 135, all of SEQ ID NOs: 128-130 and 136, all of SEQ ID NOs: 125-130 and 135-136, all of SEQ ID NOs: 137-139 and 147, all of SEQ ID NOs: 140-142 and 148, all of SEQ ID NOs: 137-142 and 147-148, all of SEQ ID NOs: 149-151 and 159, all of SEQ ID NOs: 149-150, 207, and 159, all of SEQ ID NOs: 152-154 and 160, all of SEQ ID NOs: 149-154 and 159-160, or all of SEQ ID NOs: 149-150, 207, 152-154, and 159-160. Preferably, the polypeptide comprises the amino acid sequences of all of SEQ ID NOs: 3-8 and 13-14, all of SEQ ID NOs: 125-130 and 135-136, all of SEQ ID NOs: 137-142 and 147-148, all of SEQ ID NOs: 149-154 and 159-160, or all of SEQ ID NOs: 149-150, 207, 152-154, and 159-160.

In an embodiment of the invention, the inventive polypeptide can comprise the entire length of an α or β chain of the TCR described herein. In this regard, the inventive polypeptide can comprise the amino acid sequence of SEQ ID NO: 11, SEQ ID NO: 12, SEQ ID NO: 133, SEQ ID NO: 134, SEQ ID NO: 145, SEQ ID NO: 146, SEQ ID NO: 157, SEQ ID NO: 209, SEQ ID NO: 158, both SEQ ID NOs: 11 and 12, both SEQ ID NOs: 133 and 134, both SEQ ID NOs: 145 and 146, both SEQ ID NOs: 157 and 158, or both SEQ ID NOs: 209 and 158. Preferably, the polypeptide comprises the amino acid sequences of both SEQ ID NOs: 11 and 12, both SEQ ID NOs: 133 and 134, both SEQ ID NOs: 145 and 146, both SEQ ID NOs: 157 and 158, or both SEQ ID NOs: 209 and 158.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8; a first polypeptide chain comprising the amino acid sequences of SEQ ID NOs: 125-127 and a second polypeptide chain comprising the amino acid sequence of SEQ ID NOs: 128-130; a first polypeptide chain comprising the amino acid sequences of SEQ ID NOs: 137-139 and a second polypeptide chain comprising the amino acid sequence of SEQ ID NOs: 140-142; a first polypeptide chain comprising the amino acid sequences of SEQ ID NOs: 149-151 and a second polypeptide chain comprising the amino acid sequence of SEQ ID NOs: 152-154; or a first polypeptide chain comprising the amino acid sequences of SEQ ID NOs: 149-150 and 207 and a second polypeptide chain comprising the amino acid sequence of SEQ ID NOs: 152-154. Alternatively or additionally, the protein of the invention can comprise a first polypeptide chain comprising the amino acid sequence of SEQ ID NO: 9 and a second polypeptide chain comprising the amino acid sequence of SEQ ID NO: 10; a first polypeptide chain comprising the amino acid sequence of SEQ ID NO: 131 and a second polypeptide chain comprising the amino acid sequence of SEQ ID NO: 132; a first polypeptide chain comprising the amino acid sequence of SEQ ID NO: 143 and a second polypeptide chain comprising the amino acid sequence of SEQ ID NO: 144; a first polypeptide chain comprising the amino acid sequence of SEQ ID NO: 155 and a second polypeptide chain comprising the amino acid sequence of SEQ ID NO: 156; or a first polypeptide chain comprising the amino acid sequence of SEQ ID NO: 208 and a second polypeptide chain comprising the amino acid sequence of SEQ ID NO: 156. The protein can, for example, comprise (a) a first polypeptide chain comprising the amino acid sequences of both SEQ ID NOs: 9 and 13 or all of SEQ ID NOs: 3-5 and 13 and a second polypeptide chain comprising the amino acid sequences of both SEQ ID NOs: 10 and 14 or all of SEQ ID NOs: 6-8 and 14; (b) a first polypeptide chain comprising the amino acid sequences of both SEQ ID NOs: 131 and 135 or all of SEQ ID NOs: 125-127 and 135 and a second polypeptide chain comprising the amino acid sequences of both SEQ ID NOs: 132 and 136 or all of SEQ ID NOs: 128-130 and 136; (c) a first polypeptide chain comprising the amino acid sequences of both SEQ ID NOs: 143 and 147 or all of SEQ ID NOs: 137-139 and 147 and a second polypeptide chain comprising the amino acid sequences of both SEQ ID NOs: 144 and 148 or all of SEQ ID NOs: 140-142 and 148; (d) a first polypeptide chain comprising the amino acid sequences of both SEQ ID NOs: 155 and 159 or all of SEQ ID NOs: 149-151 and 159 and a second polypeptide chain comprising the amino acid sequences of both SEQ ID NOs: 156 and 160 or all of SEQ ID NOs: 152-154 and 160; or (e) a first polypeptide chain comprising the amino acid sequences of both SEQ ID NOs: 208 and 159 or all of SEQ ID NOs: 149-150, 207 and 159 and a second polypeptide chain comprising the amino acid sequences of both SEQ ID NOs: 156 and 160 or all of SEQ ID NOs: 152-154 and 160. Alternatively or additionally, the protein of the invention can comprise (a) a first polypeptide chain comprising the amino acid sequence of SEQ ID NO: 11 and a second polypeptide chain comprising the amino acid sequence of SEQ ID NO: 12; (b) a first polypeptide chain comprising the amino acid sequence of SEQ ID NO: 133 and a second polypeptide chain comprising the amino acid sequence of SEQ ID NO: 134; (c) a first polypeptide chain comprising the amino acid sequence of SEQ ID NO: 145 and a second polypeptide chain comprising the amino acid sequence of SEQ ID NO: 146; (d) a first polypeptide chain comprising the amino acid sequence of SEQ ID NO: 157 and a second polypeptide chain comprising the amino acid sequence of SEQ ID NO: 158; or (e) a first polypeptide chain comprising the amino acid sequence of SEQ ID NO: 209 and a second polypeptide chain comprising the amino acid sequence of SEQ ID NO: 158. In this instance, the protein of the invention can be a TCR. Alternatively, if, for example, the protein comprises a single polypeptide chain comprising the amino acid sequences of both SEQ ID NOs: 11 and 12, both SEQ ID NOs: 133 and 134, both SEQ ID NOs: 145 and 146, both SEQ ID NOs: 157 and 158, or both SEQ ID NOs: 209 and 158, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention comprising both SEQ ID NOs: 11 and 12, both SEQ ID NOs: 133 and 134, both SEQ ID NOs: 145 and 146, both SEQ ID NOs: 157 and 158, both SEQ ID NOs: 209 and 158, both SEQ ID NO: 9 and 10, both SEQ ID NOs: 131 and 132, both SEQ ID NOs: 143 and 144, both SEQ ID NOs: 155 and 156, both SEQ ID NOs: 208 and 156, all of SEQ ID NOs: 3-8, all of SEQ ID NOs: 125-130, all of SEQ ID NOs: 137-142, all of SEQ ID NOs: 149-154, all of SEQ ID NOs: 9, 10, 13, and 14, all of SEQ ID NOs: 131, 132, 135, and 136, all of SEQ ID NOs: 143, 144, 147, and 148, all of SEQ ID NOs: 155, 156, 159, and 160, all of SEQ ID NOs: 208, 156, 159, and 160, all of SEQ ID NOs: 3-8 and 13-14, all of SEQ ID NOs: 125-130 and 135-136, all of SEQ ID NOs: 137-142 and 147-148, all of SEQ ID NOs: 149-154 and 159-160, or all of SEQ ID NOs: 149-150, 207, 152-154, and 159-160 may further comprise a linker peptide. The linker peptide may advantageously facilitate the expression of a recombinant TCR, polypeptide, and/or protein in a host cell. The linker peptide may comprise any suitable amino acid sequence. In an embodiment of the invention, the TCR, polypeptide, or protein comprises a self-cleaving, viral linker peptide. For example, the linker peptide may comprise SEQ ID NO: 28. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains (for example, the amino acid sequence of SEQ ID NO: 45 (anti-KRAS G12D TCR), SEQ ID NO: 162 (anti-KRAS G12D TCR), SEQ ID NO: 201 (anti-KRAS G12V TCR), or SEQ ID NO: 203 (anti-KRAS G12V TCR)).

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of α heavy or light chain, a single chain variable fragment (scFv), or an Fc, Fab, or F(ab)₂' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to mutated target, e.g., mutated KRAS; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, NY (2012). Alternatively, the TCRs, polypeptides, and/or proteins described herein (including functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins, nucleic acids, recombinant expression vectors, host cells, populations of host cells, and antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any nucleotide sequence which encodes any of the TCRs, polypeptides, or proteins described herein. In an embodiment of the invention, the nucleic acid may comprise the nucleotide sequence of (a) SEQ ID NO: 22 (CDR1 of anti-KRAS G12D TCR α chain); the nucleotide sequence of SEQ ID NO: 23 (CDR2 of anti-KRAS G12D TCR α chain); the nucleotide sequence of SEQ ID NO: 24 (CDR3 of anti-KRAS G12D TCR α chain); the nucleotide sequence of SEQ ID NO: 25 (CDR1 of anti-KRAS G12D TCR β chain); the nucleotide sequence of SEQ ID NO: 26 (CDR2 of anti-KRAS G12D TCR β chain); or the nucleotide sequence of SEQ ID NO: 27 (CDR3 of anti-KRAS G12D TCR β chain); (b) SEQ ID NO: 164 (CDR1 of anti-KRAS G12D TCR α chain); the nucleotide sequence of SEQ ID NO: 165 (CDR2 of anti-KRAS G12D TCR α chain); the nucleotide sequence of SEQ ID NO: 166 (CDR3 of anti-KRAS G12D TCR α chain); the nucleotide sequence of SEQ ID NO: 167 (CDR1 of anti-KRAS G12D TCR β chain); the nucleotide sequence of SEQ ID NO: 168 (CDR2 of anti-KRAS G12D TCR β chain); or the nucleotide sequence of SEQ ID NO: 169 (CDR3 of anti-KRAS G12D TCR β chain); (c) SEQ ID NO: 177 (CDR1 of anti-KRAS G12V TCR α chain); the nucleotide sequence of SEQ ID NO: 178 (CDR2 of anti-KRAS G12V TCR α chain); the nucleotide sequence of SEQ ID NO: 179 (CDR3 of anti-KRAS G12V TCR α chain); the nucleotide sequence of SEQ ID NO: 180 (CDR1 of anti-KRAS G12V TCR β chain); the nucleotide sequence of SEQ ID NO: 181 (CDR2 of anti-KRAS G12V TCR β chain); or the nucleotide sequence of SEQ ID NO: 182 (CDR3 of anti-KRAS G12V TCR β chain); or (d) SEQ ID NO: 189 (CDR1 of anti-KRAS G12V TCR α chain); the nucleotide sequence of SEQ ID NO: 190 (CDR2 of anti-KRAS G12V TCR α chain); the nucleotide sequence of SEQ ID NO: 191 (CDR3 of anti-KRAS G12V TCR α chain); the nucleotide sequence of SEQ ID NO: 192 (CDR1 of anti-KRAS G12V TCR β chain); the nucleotide sequence of SEQ ID NO: 193 (CDR2 of anti-KRAS G12V TCR β chain); or the nucleotide sequence of SEQ ID NO: 194 (CDR3 of anti-KRAS G12V TCR β chain). Preferably, the nucleic acid comprises the nucleotide sequences of all of SEQ ID NOs: 22-24; all of SEQ ID NOs: 25-27; all of SEQ ID NOs: 22-27; all of SEQ ID NOs: 164-166; all of SEQ ID NOs: 167-169; all of SEQ ID NOs: 164-169; all of SEQ ID NOs: 177-179; all of SEQ ID NOs: 180-182; all of SEQ ID NOs: 177-182; all of SEQ ID NOs: 189-191; all of SEQ ID NOs: 192-194; SEQ ID NOs: 189-194. In an especially preferred embodiment, the nucleic acid comprises the nucleotide sequences of all of SEQ ID NOs: 22-27; all of SEQ ID NOs: 164-169; all of SEQ ID NOs: 177-182; or all of SEQ ID NOs: 189-194. In an embodiment of the invention, the nucleic acid may comprise the nucleotide sequence of (a) SEQ ID NO: 15 (variable region of anti-KRAS G12D TCR α chain); SEQ ID NO: 16 (variable region of anti-KRAS G12D TCR β chain); or both SEQ ID NOs: 15 and 16; (b) SEQ ID NO: 170 (variable region of anti-KRAS G12D TCR α chain); SEQ ID NO: 171 (variable region of anti-KRAS G12D TCR β chain); or both SEQ ID NOs: 170 and 171; (c) SEQ ID NO: 183 (variable region of anti-KRAS G12V TCR α chain); SEQ ID NO: 184 (variable region of anti-KRAS G12V TCR β chain); or both SEQ ID NOs: 183 and 184; (d) SEQ ID NO: 195 (variable region of anti-KRAS G12V TCR α chain); SEQ ID NO: 196 (variable region of anti-KRAS G12V TCR β chain); or both SEQ ID NOs: 195 and 196. Preferably, the nucleic acid comprises the nucleotide sequences of both SEQ ID NOs: 15 and 16; both SEQ ID NOs: 170 and 171; both SEQ ID NOs: 183 and 184; or both SEQ ID NOs: 195 and 196. In another embodiment of the invention, the nucleic acid may comprise the nucleotide sequence of (a) SEQ ID NO: 17 (full-length anti-KRAS G12D TCR α chain); SEQ ID NO: 18 (full length anti-KRAS G12D TCR β chain); or both of SEQ ID NOs: 17 and 18; (b) SEQ ID NO: 172 (full-length anti-KRAS G12D TCR α chain); SEQ ID NO: 173 (full length anti-KRAS G12D TCR β chain); or both of SEQ ID NOs: 172 and 173; (c) SEQ ID NO: 185 (full-length anti-KRAS G12V TCR α chain); SEQ ID NO: 186 (full length anti-KRAS G12V TCR β chain); or both of SEQ ID NOs: 185 and 186; or (d) SEQ ID NO: 197 (full-length anti-KRAS G12V TCR α chain); SEQ ID NO: 198 (full length anti-KRAS G12V TCR β chain); or both of SEQ ID NOs: 197 and 198. Preferably, the nucleic acid comprises the nucleotide sequences of both of SEQ ID NOs: 17 and 18; both SEQ ID NOs: 172 and 173; both SEQ ID NOs: 185 and 186; or both SEQ ID NOs: 197 and 198.

In an embodiment of the invention, the nucleic acid further comprises a nucleotide sequence that encodes the constant region of a TCR α or β chain. In this regard, any of the nucleic acids described herein may further comprise the nucleotide sequence of (a) SEQ ID NO: 19 (constant region of anti-KRAS G12D TCR α chain); SEQ ID NO: 20 (constant region of anti-KRAS G12D TCR β chain); or both SEQ ID NOs: 19 and 20; (b) SEQ ID NO: 174 (constant region of anti-KRAS G12D TCR α chain); SEQ ID NO: 175 (constant region of anti-KRAS G12D TCR β chain); or both SEQ ID NOs: 174 and 175; (c) SEQ ID NO: 187 (constant region of anti-KRAS G12V TCR α chain); SEQ ID NO: 188 (constant region of anti-KRAS G12V TCR β chain); or both SEQ ID NOs: 187 and 188; or (d) SEQ ID NO: 199 (constant region of anti-KRAS G12V TCR α chain); SEQ ID NO: 200 (constant region of anti-KRAS G12V TCR β chain); or both SEQ ID NOs: 199 and 200. Preferably, the nucleic acid comprises the nucleotide sequence of both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; all of SEQ ID NOs: 22-27 and 19-20; both SEQ ID NO: 170 and 174; both SEQ ID NOs: 171 and 175; all of SEQ ID NOs: 170-171 and 174-175; all of SEQ ID NOs: 164-166 and 174; all of SEQ ID NOs: 167-169 and 175; all of SEQ ID NOs: 164-169 and 174-175; both of SEQ ID NOs: 183 and 187; both of SEQ ID NOs: 184 and 188; all of SEQ ID NOs: 183-184 and 187-188; SEQ ID NO: 177-179 and 187; all of SEQ ID NOs: 180-182 and 188; all of SEQ ID NOs: 177-182 and 187-188; both of SEQ ID NOs: 195 and 199; both of SEQ ID NOs: 196 and 200; all of SEQ ID NOs: 195-196 and 199-200; all of SEQ ID NOs: 189-191 and 199; all of SEQ ID NOs: 192-194 and 200; or all of SEQ ID NOs: 189-194 and 199-200. In an especially preferred embodiment, the nucleic acid comprises the nucleotide sequences of all of SEQ ID NOs: 15-16 and 19-20; all of SEQ ID NOs: 22-27 and 19-20; all of SEQ ID NOs: 170-171 and 174-175; all of SEQ ID NOs: 164-169 and 174-175; all of SEQ ID NOs: 183-184 and 187-188; all of SEQ ID NOs: 177-182 and 187-188; all of SEQ ID NOs: 195-196 and 199-200; or all of SEQ ID NOs: 189-194 and 199-200.

Any of the nucleic acids described herein may further comprise a nucleotide sequence encoding a linker peptide. The nucleotide sequence encoding the linker peptide may comprise any suitable nucleotide sequence. For example, the nucleotide sequence encoding a linker peptide may comprise the nucleotide sequence of SEQ ID NO: 44.

In an embodiment of the invention, a nucleic acid comprising the nucleotide sequence of all of SEQ ID NOs: 22-24; all of SEQ ID NOs: 25-27; all of SEQ ID NOs: 22-27; both SEQ ID NOs: 15 and 16; both SEQ ID NOs: 17 and 18; both SEQ ID NOs: 15 and 19; both SEQ ID NOs: 16 and 20; all of SEQ ID NOs: 15-16 and 19-20; all of SEQ ID NOs: 22-24 and 19; all of SEQ ID NOs: 25-27 and 20; all of SEQ ID NOs: 22-27 and 19-20; all of SEQ ID NOs: 164-169; both SEQ ID NOs: 170 and 171; both SEQ ID NOs: 172 and 173; all of SEQ ID NOs: 164-169 and 174-175; all of SEQ ID NOs: 170-171 and 174-175; all of SEQ ID NOs: 177-182; both of SEQ ID NO: 183-184; both of SEQ ID NOs: 185-186; all of SEQ ID NOs: 177-182 and 187-188; all of SEQ ID NOs: 183-184 and 187-188; all of SEQ ID NOs: 189-194; both of SEQ ID NOs: 195-196; both of SEQ ID NOs: 197-198; all of SEQ ID NOs: 189-194 and 199-200; or all of SEQ ID NOs: 195-196 and 199-200 encodes a murine TCR.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises the nucleotide sequence of SEQ ID NO: 21 (encoding α and β chains SEQ ID NOs: 11 and 12 with a linker positioned between them); SEQ ID NO: 163 (encoding α and β chains SEQ ID NOs: 157 and 158 with a linker positioned between them); SEQ ID NO: 202 (encoding α and β chains SEQ ID NOs: 145 and 146 with a linker positioned between them); or SEQ ID NO: 176 (encoding α and β chains SEQ ID NOs: 133 and 134 with a linker positioned between them).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.$ $coli$ cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., $J.$ $Immunother.$, 26:332-42 (2003); and Riddell et al., $J.$ $Immunol.$ $Methods$, 128:189-201 (1990). In an embodiment, expansion of the numbers of T cells is carried out by culturing the T cells with OKT3 antibody, IL-2, and feeder PBMC (e.g., irradiated allogeneic PBMC).

The invention further provides an antibody, or antigen binding portion thereof, which specifically binds to a functional portion of any of the TCRs described herein. Preferably, the functional portion specifically binds to the cancer antigen, e.g., the functional portion comprising the amino acid sequence SEQ ID NO: 3, 125, 137, or 149 (CDR1 of a chain), SEQ ID NO: 4, 126, 138, or 150 (CDR2 of α chain), SEQ ID NO: 5, 127, 139, 151, or 207 (CDR3 of α chain), SEQ ID NO: 6, 128, 140, or 152 (CDR1 of β chain), SEQ ID NO: 7, 129, 141, or 153 (CDR2 of β chain), SEQ ID NO: 8, 130, 142, or 154 (CDR3 of β chain), SEQ ID NO: 9, 131, 143, 155, or 208 (variable region of α chain), SEQ ID NO: 10, 132, 144, or 156 (variable region of β chain), or a combination thereof, e.g., SEQ ID NOs: 3-5; SEQ ID NOs: 6-8; SEQ ID NOs: 3-8; SEQ ID NO: 9; SEQ ID NO: 10; SEQ ID NOs: 9-10; SEQ ID NOs: 125-127, SEQ ID NOs: 128-130, SEQ ID NOs: 125-130, SEQ ID NOs: 137-139, SEQ ID NOs: 140-142, SEQ ID NOs: 137-142, SEQ ID NOs: 149-151, SEQ ID NOs: 149-150 and 207, SEQ ID NOs: 152-154, SEQ ID NOs: 149-154; SEQ ID NOs: 149-150, 207, and 152-154; SEQ ID NOs: 131-132, SEQ ID NOs: 143-144, SEQ ID NOs: 155-156; SEQ ID NO: 208; or SEQ ID NOs: 208 and 156. More preferably, the functional portion comprises the amino acid sequences of SEQ ID NOs: 3-8, SEQ ID NOs: 9 and 10, SEQ ID NOs: 125-130, SEQ ID NOs: 137-142, SEQ ID NOs: 149-154, SEQ ID NOs: 149-150, 207, and 152-154, SEQ ID NOs: 131-132, SEQ ID NOs: 143-144, SEQ ID NOs: 155-156, or SEQ ID NOs: 208 and 156. In a preferred embodiment, the antibody, or antigen binding portion thereof, binds to an epitope which is formed by all 6 CDRs (CDR1-3 of the α chain and CDR1-3 of the β chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays.

Suitable methods of making antibodies are known in the art. For instance, standard hybridoma methods are described in, e.g., C. A. Janeway et al. (eds.), *Immunobiology*, $8^{th}$ Ed., Garland Publishing, New York, NY (2011)). Alternatively, other methods, such as EBV-hybridoma methods, methods of producing antibodies in non-human animals, and bacteriophage vector expression systems are known in the art.

Phage display can also be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual*, $4^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra).

Methods for generating humanized antibodies are well known in the art. Antibodies can also be produced by transgenic mice that are transgenic for specific heavy and light chain immunoglobulin genes. Such methods are known in the art and described in, for example, Janeway et al., supra.

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology. Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins, nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated KRAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to mutated target, e.g., mutated KRAS or to detect, treat, or prevent cancer.

It is contemplated that the inventive pharmaceutical compositions, TCRs, polypeptides, proteins, nucleic acids, recombinant expression vectors, host cells, or populations of cells can be used in methods of treating or preventing cancer.

Without being bound to a particular theory, the inventive TCRs are believed to bind specifically to mutated target, e.g., mutated KRAS, such that the TCR (or related inventive polypeptide or protein), when expressed by a cell, is able to mediate an immune response against a target cell expressing mutated target, e.g., mutated KRAS. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic carcinoma. In another preferred embodiment, the cancer is a cancer that expresses the mutated amino acid sequence of VVVGADGVGK (SEQ ID NO: 2), VVGADGVGK (SEQ ID NO: 34), VVVGAVGVGK (SEQ ID NO: 33), or VVGAVGVGK (SEQ ID NO: 35), which are present in mutated human KRAS, mutated human NRAS, and mutated human HRAS.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of murine anti-KRAS$_{7-16}$ G12D 10-mer TCRs.

A computer algorithm was used to generate candidate HLA-A11*01 KRAS peptides. For the algorithm, the strong binder threshold was 50 nM, and the weak binder threshold was 500 nM. The candidate peptides are shown in Table 1.

TABLE 1

| Description | SEQ ID NO: | Sequence | HLA-A11*01 (nM) |
|---|---|---|---|
| G12D 9-mer | 34 | VVGADGVGK | 194 |
| G12D 10-mer | 2 | VVVGADGVGK | 220 |
| G12V 9-mer | 35 | VVGAVGVGK | 50 |
| G12V 10-mer | 33 | VVVGAVGVGK | 71 |
| G12C 9-mer | 36 | VVGACGVGK | 69 |
| G12C 10-mer | 37 | VVVGACGVGK | 120 |
| G12R 9-mer | 38 | VVGARGVGK | 86 |
| G12R 10-mer | 39 | VVVGARGVGK | 119 |

HLA-A11 transgenic mice were immunized with the G12D 10-mer peptide (SEQ ID NO: 2) three times. After the third immunization, the spleen and lymph nodes were removed and cultured in vitro with the G12D 10-mer peptide at various concentrations (1 μM, 0.1 μM, and 0.01 μM) for seven days. T cells isolated from the lymph node (LN) and spleen cultures were tested for reactivity against (i) COS7 cells transduced to express HLA-A11 (COST/A11) which had been pulsed with (a) no peptide (COS/A11), (b) WT KRAS$_{7-16}$ peptide (SEQ ID NO: 30) (COS/A11+WT peptide), (c) G12D 10-mer peptide (SEQ ID NO: 2) (COS/A11+G12D peptide), or (d) G12V 10-mer peptide (SEQ ID NO: 33) (COS/A11+G12V peptide); and (ii) COS7/A11 cells transfected with a vector encoding a (a) WT KRAS minigene (encoding 23-mer SEQ ID NO: 118) (COS/A11/WT) or (b) G12D minigene (encoding 23-mer SEQ ID NO: 119) (COS/A11/G12D). Interferon (IFN)-γ was measured. The results are shown in Table 2A (pulsed target cells) and Table 2B (transfected target cells). As shown in Tables 2A and 2B, HLA-A11 restricted murine T cells were reactive against KRAS G12D peptide SEQ ID NO: 2.

TABLE 2A

| | | mIFN-γ (pg/ml) | | | |
|---|---|---|---|---|---|
| Stimulated with G12D peptide | | COS/ A11 | COS/ A11 + WT peptide | COS/ A11 + G12D peptide | COS/ A11 + G12V peptide |
| 0.01 uM | LN-well (W) 1 | 50 | 34 | >20000 | 52 |
| | LN-W2 | 52 | 57 | >20000 | 95 |
| | LN-W3 | 169 | 92 | 12849 | 61 |
| | Spleen-W1 | 32 | 32 | 45 | 33 |
| | Spleen-W2 | 35 | 50 | 57 | 44 |
| | Spleen-W3 | 68 | 72 | 94 | 40 |
| 0.1 uM | LN-W1 | 38 | 38 | 16729 | 36 |
| | LN-W2 | 62 | 81 | >20000 | 81 |
| | LN-W3 | 73 | 116 | >20000 | 129 |
| | Spleen-W1 | 36 | 43 | 14423 | 35 |
| | Spleen-W2 | 33 | 34 | >20000 | 33 |
| | Spleen-W3 | 44 | 40 | 18107 | 38 |
| 1 uM | LN-W1 | 101 | 210 | >20000 | 407 |
| | LN-W2 | 92 | 248 | >20000 | 577 |
| | LN-W3 | 57 | 226 | >20000 | 403 |
| | Spleen-W1 | 32 | 44 | >20000 | 55 |

TABLE 2A-continued

| Stimulated with G12D peptide | COS/A11 | COS/A11 + WT peptide | COS/A11 + G12D peptide | COS/A11 + G12V peptide |
|---|---|---|---|---|
| Spleen-W2 | 34 | 70 | >20000 | 108 |
| Spleen-W3 | 42 | 78 | >20000 | 261 |

TABLE 2B

| | mIFN-γ (pg/ml) | | |
|---|---|---|---|
| | COS/A11 | COS/A11/WT | COS/A11/G12D |
| Spleen-W1 | 32 | 32 | 19184 |
| Spleen-W2 | 34 | 36 | 19545 |
| Spleen-W3 | 42 | 45 | >20000 |
| LN-W1 | 101 | 74 | 6001 |
| LN-W2 | 92 | 147 | 13589 |
| LN-W3 | 57 | 64 | 11644 |
| Spleen-W1 | 36 | 53 | 12865 |
| Spleen-W2 | 33 | 49 | 12728 |
| Spleen-W3 | 44 | 45 | 12125 |
| LN-W1 | 38 | 44 | 7025 |
| LN-W2 | 62 | 54 | 19384 |
| LN-W3 | 73 | 66 | 17431 |
| Spleen-W1 | 32 | 32 | 52 |
| Spleen-W2 | 35 | 35 | 63 |
| Spleen-W3 | 68 | 36 | 94 |
| LN-W1 | 50 | 38 | 12096 |
| LN-W2 | 52 | 56 | 14098 |
| LN-W3 | 169 | 46 | 6877 |

The TCR was isolated from the cells in each positive well using 5' Rapid Amplification of cDNA Ends (RACE). Two dominant alpha chains and four dominant beta chains were identified (Table 3).

TABLE 3

| | V Region | D/J Region | CDR3 | SEQ ID NO: |
|---|---|---|---|---|
| Alpha chains | TRAV12N-3*01 | 39*01 | CALRGNAGAKLTF | 5 |
| | TRAV16D/DV11*03 | 52*01 | CAMREDTGANTGKLTF | 40 |
| Beta chains | TRBV4*01 (CB2) | 2*01/2-3*01 | CASSSRDWSAETLYF | 8 |
| | TRBV5*01 (CB2) | 2*01/2-1*01 | CASSQDSLGRAEQFF | 41 |
| | TRBV16*01 (CB2) (LN 0.01) | 2*01/2-3*01 | CASSSDWGGAETLYF | 42 |
| | TRBV16*01 (CB2) (Spl) | 2*01/2-3*01 | CASSSGLGSSAETLYF | 43 |

Example 2

This example demonstrates that PBL transduced to express a TCR α chain comprising SEQ ID NO: 11 and a TCR β chain comprising SEQ ID NO: 12 are reactive against HLA-A11+/G12D 10-mer+ targets.

The two dominant α chains and four dominant β chains of Table 3 were individually cloned into MSGV1 retroviral vectors. PBL were individually co-transduced to express one of various pairs of an α and β chain, as shown in Table 4. Transduced PBL were screened for reactivity against (i) HLA-A11-expressing T2/A11+(Table 4A) or COS7/A11+ (Table 4B) cells pulsed with (a) G12D 10-mer peptide (SEQ ID NO: 2), (b) G12V 10-mer peptide (SEQ ID NO: 33), (c) WT KRAS 10-mer peptide (SEQ ID NO: 30), or (d) no peptide (none); or (ii) COS7/A11 cells transduced with a (a) G12D minigene (encoding 23-mer SEQ ID NO: 119) (COS/A11/G12D), (b) G12V minigene (encoding 23-mer SEQ ID NO: 120) (COS/A11/G12V), (c) WT KRAS minigene (encoding 23-mer SEQ ID NO: 118) (COS/A11/WT), or (d) no cells (medium only) (Table 4C). IFN-γ secretion was measured. The results are shown in Tables 4A-C. In Tables 4A-C, bold IFN-γ secretion values indicate those pairs of TCR α and β chains that demonstrated reactivity, and IFN-γ secretion values in bold with underlining indicate the pair of TCR α and β chains that demonstrated the best reactivity. As shown in Tables 4A-C, PBL co-transduced to express murine TCR α chain TRAV12N-3*01 (SEQ ID NO: 11) and murine TCR β chain TRBV4*01 (SEQ ID NO: 12) demonstrated reactivity against HLA-A11-expressing COS7 cells pulsed with G12D 10-mer or G12D transfectant target cells.

TABLE 4A

| | | IFN-γ (pg/ml) upon co-culture with T2/A11 + target cells | | | |
|---|---|---|---|---|---|
| | | None | WT 10-mer | G12D 10-mer | G12V 10-mer |
| TRAV12N-3*01 | TRBV4*01 | 108 | 136 | >10000 | 108 |
| | TRBV5*01 | 348 | 138 | 319 | 263 |
| | TRBV16*01 (LN) | 107 | 100 | 93 | 120 |
| | TRBV16*01 (SP) | 234 | 132 | 246 | 132 |
| TRAV16D/DV11*03 | TRBV4*01 | 56 | 39 | 595 | 39 |
| | TRBV5*01 | 140 | 146 | 848 | 155 |
| | TRBV16*01 (LN) | 71 | 100 | 135 | 51 |
| | TRBV16*01 (SP) | 228 | 297 | 133 | 144 |

TABLE 4B

| | | IFN-γ (pg/ml) upon co-culture with COS/A11 + targets | | | |
|---|---|---|---|---|---|
| | | None | WT r10-mer | G12D 10-mer | G12V 10-mer |
| TRAV12N-3*01 | TRBV4*01 | 123 | 107 | >10000 | 129 |
| | TRBV5*01 | 57 | 71 | 86 | 58 |
| | TRBV16*01 (LN) | 55 | 69 | 70 | 81 |
| | TRBV16*01 (Sp) | 98 | 64 | 71 | 78 |
| TRAV16D/DV11*03 | TRBV4*01 | 71 | 57 | 246 | 71 |
| | TRBV5*01 | 74 | 66 | 1228 | 70 |
| | TRBV16*01 (LN) | 74 | 77 | 68 | 85 |
| | TRBV16*01 (Sp) | 108 | 121 | 104 | 100 |

TABLE 4C

| | | IFN-γ (pg/ml) upon co-culture with target cells | | | |
|---|---|---|---|---|---|
| | | COS/ A11/WT | COS/ A11/G12D | COS/ A11/G12V | Medium |
| TRAV12N-3*01 | TRBV4*01 | 130 | >10000 | 126 | 18 |
| | TRBV5*01 | 95 | 106 | 83 | 22 |
| | TRBV16*01 (LN) | 97 | 91 | 98 | 18 |
| | TRBV16*01 (SP) | 129 | 114 | 84 | 23 |
| TRAV16D/ DV11*03 | TRBV4*01 | 95 | 302 | 89 | 18 |
| | TRBV5*01 | 94 | 92 | 98 | 18 |
| | TRBV16*01 (LN) | 99 | 106 | 114 | 24 |
| | TRBV16*01 (SP) | 176 | 143 | 138 | 26 |

Example 3

This example demonstrates that PBL co-transduced with a TCR α chain comprising SEQ ID NO: 11 and a TCR β chain comprising SEQ ID NO: 12 are reactive against HLA-A11+/G12D+ pancreatic tumor cell line FA6-2/A11.

Human PBL were co-transduced with a TCR α chain comprising SEQ ID NO: 11 and a TCR β chain comprising SEQ ID NO: 12. Co-transduced cells were co-cultured with (i) COS7 cells transfected with (a) HLA-A11 alone (COS7/A11) or HLA-A11 transduced with a (b) WT KRAS minigene (encoding 23-mer SEQ ID NO: 118) (COS7/A11/KRAS WT), (c) KRAS G12D minigene (encoding 23-mer SEQ ID NO: 119) (COS7/A11/KRAS G12D), (d) KRAS G12V minigene (encoding 23-mer SEQ ID NO: 120) (COS7/A11/KRAS G12V); (ii) pancreatic tumor cell lines Mia-Paca2/A11, T3m4/A11, AsPC-1, FA6-2/A11, MDA-Panc-48/A11, PANC-1, PK-45p/A11, SK.PC.3/A11, x135m1/A11, or (iii) medium alone. IFN-γ secretion was measured. The results are shown in Table 5. The KRAS mutations of the tumor cell lines are indicated in parentheses. As shown in Table 5, PBL co-transduced with a TCR α chain TRAV12N-3*01 (SEQ ID NO: 11) and TCR β chain TRBV4*01 (SEQ ID NO: 12) demonstrated reactivity against HLA-A11+/G12D+ pancreatic tumor cell line FA6-2/A11.

TABLE 5

| Target Cell | IFN-γ (pg/mL) |
|---|---|
| COS7/A11 | 146 |
| COS7/A11/KRAS WT | 116 |
| COS7/A11/KRAS (G12D) | 18231 |
| COS7/A11/KRAS (G12V) | 111 |
| Mia-Paca2/A11 (G12C)* | 53 |
| T3m4/A11 (Q61H)* | 178 |
| SK.PC.3/A11 (G12V)** | 53 |
| x135m1/A11 (G12V)** | 105 |
| AsPC-1 (G12D)** | 18 |
| FA6-2/A11 (G12D)** | 3982 |
| MDA-Panc-48/A11 (G12D)** | 56 |
| PANC-1 (A11+, G12D)** | 28 |
| PK.45p/A11 (G12D)** | 231 |
| Medium (no cells) | 26 |

*Mutation determined by genotyping.
**Mutation determined by enotypin and mRNA expression (see Tables 13 and 20).

Example 4

This example demonstrates that PBL that were transduced with a retroviral vector encoding a TCR α chain TRAV12N-3*01 (SEQ ID NO: 11) and TCR β chain TRBV4*01 (SEQ ID NO: 12) demonstrated reactivity against COS7/A11 cells pulsed with KRAS G12D 10-mer peptide (SEQ ID NO: 2).

Human PBL were transduced with a retroviral vector encoding the TCR α chain TRAV12N-3*01 (SEQ ID NO: 11) and TCR β chain TRBV4*01 (SEQ ID NO: 12). Transduced PBL were co-cultured with COS7/A11 cells that were pulsed with KRAS G12D 10-mer peptide (SEQ ID NO: 2), KRAS G12D 9-mer peptide (SEQ ID NO: 34), KRAS G12D 9-mer peptide SEQ ID NO: 124, KRAS G12V 10-mer peptide (SEQ ID NO: 33), or WT KRAS 10-mer peptide (SEQ ID NO: 30) at various concentrations shown in Table 6. IFN-γ secretion was measured. The results are shown in Table 6. As shown in Table 6, human PBL transduced to express a TCR α chain TRAV12N-3*01 (SEQ ID NO: 11) and TCR β chain TRBV4*01 (SEQ ID NO: 12) demonstrated reactivity against COS7/A11 cells pulsed with KRAS G12D 10-mer peptide (SEQ ID NO: 2).

TABLE 6

| | IFN-γ (pg/mL) | | | | |
|---|---|---|---|---|---|
| Peptide concentration (M) | G12D 10-mer | G12D KRAS$_{7-15}$ 9-mer (VVGADGVG) SEQ ID NO: 124 | G12V 10-mer | G12D KRAS$_{8-16}$ 9-mer (VVGADGVGK) SEQ ID NO: 34 | WT 10-mer |
| $1 \times 10^{-6}$ | 16918 | 87 | 97 | 136 | 78 |
| $1 \times 10^{-7}$ | 8677 | 91 | 83 | 95 | 88 |
| $1 \times 10^{-8}$ | 4220 | 72 | 86 | 99 | 102 |
| $1 \times 10^{-9}$ | 775 | 90 | 88 | 90 | 99 |
| $1 \times 10^{-10}$ | 115 | 90 | 88 | 85 | 95 |
| $1 \times 10^{-11}$ | 98 | 95 | 86 | 85 | 86 |
| $1 \times 10^{-12}$ | 111 | 83 | 96 | 94 | 102 |
| $1 \times 10^{-13}$ | 80 | 112 | 97 | 115 | 98 |

Example 5

This example demonstrates that PBL that were transduced with a retroviral vector encoding a TCR α chain TRAV12N-3*01 (SEQ ID NO: 11) and TCR β chain TRBV4*01 (SEQ ID NO: 12) demonstrated reactivity against HLA-A11-expressing pancreatic tumor line FA6-2/A11.

Human PBL were transduced with a retroviral vector encoding the TCR α chain TRAV12N-3*01 (SEQ ID NO: 11) and TCR β chain TRBV4*01 (SEQ ID NO: 12). Untransduced control PBL or transduced PBL were co-cultured with the target cells set forth in Table 7. IFN-γ secretion was measured. The results are shown in Table 7. The KRAS mutations of the tumor cell lines are indicated in parentheses. As shown in Table 7, human PBL transduced to express a TCR α chain TRAV12N-3*01 (SEQ ID NO: 11) and TCR β chain TRBV4*01 (SEQ ID NO: 12) demonstrated reactivity against FA6-2/A11 tumor cell line. Untransduced PBL secreted less than 100 pg/mL IFN-γ upon co-culture with each target cell set forth in Table 7.

TABLE 7

| Target Cell | IFN-γ (pg/mL) |
|---|---|
| COS7/A11 | 90 |
| COS7/A11/KRAS WT | 71 |
| COS7/A11/KRAS (G12D) | 15496 |
| COS7/A11/KRAS (G12V) | 58 |
| Barr (A11+, G12R)* | 21 |
| BxPC3/A11 (WT)* | 18 |
| Mia-Paca2/A11 (G12C)* | 57 |
| Paca44/A11 (G12V)** | 30 |

TABLE 7-continued

| Target Cell | IFN-γ (pg/mL) |
|---|---|
| T3m4/A11 (Q61H)* | 28 |
| AsPC-1/A11 (G12D)** | 60 |
| FA6-2/A11 (G12D)** | 753 |
| MDA-Panc-48/A11 (G12D)** | 23 |
| PANC-1 (A11+, G12D)** | 23 |
| PK.45p/A11 (G12D)** | 28 |
| Medium (no cells) | 38 |

*Mutation (or lack thereof (i.e., "WT") determined by genotyping.
**Mutation determined by genotyping and mRNA expression (see Tables 13 and 20).

Example 6

This example demonstrates the isolation of murine anti-KRAS$_{7-16}$ G12V 10-mer TCRs.

HLA-A11 transgenic mice were immunized with the G12V 10-mer peptide (SEQ ID NO: 33) twice. After the second immunization, the spleen and lymph nodes were removed and cultured in vitro with the G12V 10-mer peptide at various concentrations (1 μM, 0.1 μM, and 0.01 μM) for seven days. T cells isolated from the lymph node and spleen cultures were tested for reactivity against (i) COS7/A11 cells transfected with a vector encoding (a) G12V minigene (encoding 23-mer SEQ ID NO: 120) (COSA11/G12V); (b) WT KRAS minigene (encoding 23-mer SEQ ID NO: 118) (COSA11/WT); (c) G12D minigene (encoding 23-mer SEQ ID NO: 119) (COSA11/G12D); (ii) HLA-A11-expressing KRAS G12V+ pancreatic tumor cell lines Paca44/A11, SKPC3/A11, or x135m1/A11; or (iii) no target cells (medium) (Table 8). The results are shown in Table 8. In Table 8, underlined IFN-γ secretion values indicate those cells that demonstrated reactivity against transfectants and tumors.

TABLE 8

| | mIFN-γ (pg/ml) | | | | | |
|---|---|---|---|---|---|---|
| | Spleen (1 μM) | Spleen (0.1 μM) | Spleen (0.01 μM) | LN (1 μM) | LN (0.1 μM) | LN (0.01 μM) |
| Cos7/A11/WT | 34 | 32 | 32 | 38 | 46 | 37 |
| Cos7/A11/G12D | 61 | 32 | 32 | 41 | 41 | 38 |
| Cos7/A11/G12V | >20000 | 12113 | 58 | 1685 | 3126 | 4765 |
| Paca44/A11 | 32 | 32 | 36 | 39 | 44 | 39 |
| SKPC3/A11 | 8235 | 385 | 41 | 106 | 169 | 164 |
| x135 ml/A11 | 32 | 36 | 49 | 42 | 40 | 41 |
| Medium | 32 | 32 | 50 | 46 | 35 | 42 |

Oligoclonal TCRs were isolated from the cells that demonstrated highly specific G12V peptide and transfectant reactivity using 5' RACE. Two dominant alpha chains and three dominant beta chains were identified (Table 9).

TABLE 9

| | V Region | D/J Region | CDR3 | SEQ ID NO: | Frequency |
|---|---|---|---|---|---|
| Alpha chains | TRAV19*01 | 53*01 | CAAGDSGGSNYKLTF | 139 | 31% |
| | TRAV3-3*01 | 17*01 | CAVSGGTNSAGNKLTF | 204 | 14% |
| Beta chains | TRBV13-1*02 (CB2) | 2*01/2-1*01 | CASASWGGYAEQFF | 205 | 23% |
| | TRBV4*01 (CB2) | 2*01/2-1*01 | CASSRDWGPAEQFF | 130 | 15% |
| | TRBV1*01 (CB2) | 1*01/2-3*01 | CTCSADRGAETLYF | 206 | 12% |

Example 7

This example demonstrates that PBL transduced to express (i) a TCR α chain comprising SEQ ID NO: 133 and a TCR β chain comprising SEQ ID NO: 134 or (ii) a TCR α chain comprising SEQ ID NO: 145 and a TCR β chain comprising SEQ ID NO: 146 are reactive against HLA-A11+/G12V 10-mer+ targets.

The two dominant α chains and three dominant β chains of Table 9 were individually cloned into MSGV1 retroviral vectors. Anti-CD3 stimulated PBL were individually co-transduced to express one of various pairs of an α and β chain, as shown in Tables 10A-10B. Transduced PBL were screened for reactivity against (i) COS7/A11+ cells pulsed with (a) G12D 10-mer peptide (SEQ ID NO: 2), (b) G12V 10-mer peptide (SEQ ID NO: 33), or (c) WT KRAS 10-mer peptide (SEQ ID NO: 30) (Table 10A) or (ii) COS7/A11 cells transduced with a (a) G12D minigene (encoding 23-mer SEQ ID NO: 119) (COS/A11/G12D), (b) G12V minigene (encoding 23-mer SEQ ID NO: 120) (COS/A11/G12V), or (c) WT KRAS minigene (encoding 23-mer SEQ ID NO: 118) (COS/A11/WT) (Table 10B). Untransfected Cos7/A11 cells that were not pulsed with peptide (Cos7/A11) and medium with no cells (medium) served as negative controls. PBL pulsed or transduced with GFP served as a positive control. IFN-γ secretion was measured.

The results are shown in Tables 10A-10B. In Tables 10A-10B, bold IFN-γ secretion values indicate those pairs of TCR α and β chains that demonstrated reactivity. As shown in Tables 10A-10B, PBL co-transduced to express (i) both murine TCR α chain TRAV19*01 (SEQ ID NO: 145) and murine TCR β chain TRBV13-1*02 (SEQ ID NO: 146) or (ii) both murine TCR α chain TRAV3-3*01 (SEQ ID NO: 133) and murine TCR β chain TRBV4*01 (SEQ ID NO: 134) demonstrated reactivity against HLA-A11-expressing COS7 cells pulsed with G12V 10-mer or G12V transfectant target cells, but not control peptides or control transfectants.

TABLE 10A

| | (IFN-γ (pg/ml)) | | | |
|---|---|---|---|---|
| | Cos7/ A11 | Cos7/A11 + WT 10-mer | Cos7/A11 + G12D 10-mer | Cos7/A11 + G12V 10-mer | Me- dium |
| GFP | 66 | 50 | 60 | 54 | 17 |
| TRAV19*01 + TRBV13-1*02 | 105 | 90 | 94 | 14138 | 29 |
| TRAV19*01 + TRBV4*01 | 30 | 30 | 30 | 27 | 16 |
| TRAV19*01 + TRBV1*01 | 69 | 37 | 38 | 37 | 16 |
| TRAV3-3*01 + TRBV13-1*02 | 68 | 47 | 49 | 44 | 23 |
| TRAV3-3*01 + TRBV4*01 | 42 | 36 | 39 | 8374 | 16 |
| TRAV3-3*01 + TRBV1*01 | 53 | 41 | 39 | 51 | 16 |

TABLE 10B

| | (IFN-γ (pg/ml)) | | | |
|---|---|---|---|---|
| | Cos7/ A11 | Cos7/A11/ WT | Cos7/A11/ G12D | Cos7/A11/ G12V | Me- dium |
| GFP | 66 | 72 | 60 | 55 | 17 |
| TRAV19*01 + TRBV13-1*02 | 105 | 92 | 81 | 18058 | 29 |
| TRAV19*01 + TRBV4*01 | 30 | 32 | 27 | 30 | 16 |
| TRAV19*01 + TRBV1*01 | 69 | 45 | 45 | 44 | 16 |
| TRAV3-3*01 + TRBV13-1*02 | 68 | 51 | 56 | 61 | 23 |
| TRAV3-3*01 + TRBV4*01 | 42 | 41 | 38 | 11113 | 16 |
| TRAV3-3*01 + TRBV1*01 | 53 | 44 | 47 | 45 | 16 | recognized pulsed target peptide with a higher avidity as compared to the TRAV19*01/TRBV13-1*02 (SEQ ID NOs: 145 and 146) TCR. The increased reactivity of the TRAV3-3*01/TRBV4*01 (SEQ ID NOs: 145 and 146) TCR against the G12V 9-mer peptide as compared to the 10-mer peptide also suggested that 9-mer peptide is the minimal determinant.

TABLE 11A

| Peptide | IFN-γ (pg/ml) | | | | |
|---|---|---|---|---|---|
| concentration ($10^x$ μM) | WT 10-mer | G12D 9-mer | G12D 10-mer | G12V 9-mer | G12V 10-mer |
| −6 | 50 | 47 | 43 | 19479 | 9778 |
| −7 | 42 | 48 | 40 | 19900 | 6696 |
| −8 | 50 | 49 | 46 | 19193 | 657 |
| −9 | 50 | 44 | 41 | 9578 | 104 |
| −10 | 48 | 52 | 53 | 1877 | 59 |
| −11 | 55 | 49 | 43 | 119 | 52 |
| −12 | 47 | 55 | 49 | 56 | 52 |
| −13 | 68 | 52 | 49 | 60 | 52 |

TABLE 11B

| Peptide | IFN-γ (pg/ml) | | | | |
|---|---|---|---|---|---|
| concentration ($10^x$ μM) | WT 10-mer | G12D 9-mer | G12D 10-mer | G12V 9-mer | G12V 10-mer |
| −6 | 57 | 63 | 61 | 112 | 15184 |
| −7 | 56 | 57 | 50 | 70 | 7725 |
| −8 | 57 | 48 | 49 | 52 | 2084 |
| −9 | 49 | 54 | 59 | 55 | 326 |
| −10 | 57 | 62 | 52 | 64 | 61 |
| −11 | 65 | 52 | 64 | 62 | 67 |
| −12 | 67 | 57 | 62 | 66 | 61 |
| −13 | 70 | 70 | 63 | 64 | 71 |

Example 8

This example demonstrates that the TRAV3-3*01/TRBV4*01 murine anti-KRAS G12V TCR (SEQ ID NOs: 133 and 134) has a higher affinity for pulsed target peptide as compared to TRAV19*01/TRBV13-1*02 murine anti-KRAS G12V TCR (SEQ ID NOs: 145 and 146).

PBL were transduced with either (i) TRAV3-3*01/TRBV4*01 murine anti-KRAS G12V TCR (SEQ ID NOs: 133 and 134) or (ii) TRAV19*01/TRBV13-1*02 murine anti-KRAS G12V TCR (SEQ ID NOs: 145 and 146). Transduced cells were co-cultured with Cos7/A11 cells pulsed with (a) G12D 10-mer peptide (SEQ ID NO: 2), (b) G12V 10-mer peptide (SEQ ID NO: 33), (c) WT KRAS 10-mer peptide (SEQ ID NO: 30), (d) G12D 9-mer peptide (SEQ ID NO: 34), or (e) G12V 9-mer peptide (SEQ ID NO: 35) at the concentrations shown in Tables 11A and 11B. IFN-γ secretion was measured.

The results are shown in Table 11A (TRAV3-3*01/TRBV4*01 (SEQ ID NOs: 133 and 134)) and Table 11B (TRAV19*01/TRBV13-1*02 (SEQ ID NOs: 145 and 146)). In Tables 11A-11B, bold IFN-γ secretion values indicate those target peptide concentrations at which the TCR demonstrated reactivity. As shown in Tables 11A-11B, T cells transduced with the TRAV3-3*01/TRBV4*01 TCR (SEQ ID NOs: 133 and 134) recognized Cos7/A11 pulsed with both 9-mer and 10-mer peptides and recognized 9-mer at pulsed at a concentration of 0.01 nM. Accordingly, the TRAV3-3*01/TRBV4*01 TCR (SEQ ID NOs: 133 and 134)

Example 9

This example demonstrates that the TRAV3-3*01/TRBV4*01 murine anti-KRAS G12V TCR (SEQ ID NOs: 133 and 134) recognizes HLA-A11+ KRAS G12V+ pancreatic tumor cell lines.

PBL were transduced with either (i) TRAV3-3*01/TRBV4*01 murine anti-KRAS G12V TCR (SEQ ID NOs: 133 and 134) or (ii) TRAV19*01/TRBV13-1*02 murine anti-KRAS G12V TCR (SEQ ID NOs: 145 and 146). Transduced cells were co-cultured with (i) COS7/A11 cells transduced with a (a) G12D minigene (encoding 23-mer SEQ ID NO: 119) (COS/A11/G12D), (b) G12V minigene (encoding 23-mer SEQ ID NO: 120) (COS/A11/G12V), or (c) WT KRAS minigene (encoding 23-mer SEQ ID NO: 118) (COS/A11/WT); (ii) KRAS G12V negative pancreatic tumor cell lines transduced with HLA-A11; (iii) KRAS G12V+ pancreatic tumor cell lines transduced with HLA-A11; or (iv) parental (untransduced) pancreatic tumor cell lines, as shown in Table 12. IFN-γ secretion was measured.

The results are shown in Table 12. In Table 12, bold IFN-γ secretion values indicate those target cells for which the TCR demonstrated reactivity. As shown in Table 12, the TRAV3-3*01/TRBV4*01 murine anti-KRAS G12V TCR (SEQ ID NOs: 133 and 134) recognized more HLA-A11+ KRAS G12V+ pancreatic tumor cell lines as compared to the TRAV19*01/TRBV13-1*02 murine anti-KRAS G12V TCR (SEQ ID NOs: 145 and 146).

TABLE 12

| | | IFN-γ (pg/ml) | |
|---|---|---|---|
| | | TRAV3-3*01/ TRBV4*01 | TRAV19*01/ TRBV13-1*02 |
| Transfectants | Cos/A11 | 51 | 55 |
| | Cos/A11/G12D | 53 | 44 |
| | Cos/All/WT | 52 | 51 |
| | Cos/A11/G12V | 24290 | 11794 |
| HLA-A11 transduced, KRAS G12V− | BxPC3/A11 (WT)* | 25 | 32 |
| | MiaPaca2/A11 (G12C)* | 16 | 16 |
| | T3m4/A11 (Q61H)* | 26 | 33 |
| | AsPC-1/A11 (G12D)** | 22 | 26 |
| | FA6-2/A11 (G12D)** | 18 | 18 |
| | MDA-Panc-48/A11 (G12D)** | 16 | 16 |
| | PK.45p/A11 (G12D)** | 31 | 29 |
| HLA-A11 transduced, KRAS G12V+ | Capan-1/A11 (G12V)** | 99 | 28 |
| | CFPAC-1/A11 (G12V) | 224** | 28 |
| | Paca44/A11 (G12V) | 577** | 21 |
| | SK.PC3/A11 (G12V) | 7947 | 2658** |
| | x135m1/A11 (G12V) | 1020** | 90 |
| Parental tumor lines | BxPC3 (WT)* | 16 | 16 |
| | MiaPaca2 (G12C)* | 18 | 16 |
| | T3m4 (Q61H)* | 19 | 18 |
| | AsPC-1 (G12D)** | 16 | 16 |
| | FA6-2 (G12D)** | 23 | 19 |
| | MDA-Panc-48 (G12D)** | 19 | 21 |
| | PK.45p (G12D)** | 16 | 16 |
| | Capan-1 (G12V)** | 22 | 20 |
| | CFPAC-1 (G12V)** | 16 | 16 |
| | Paca44 (G12V)** | 16 | 16 |
| | SK.PC3 (G12V)** | 28 | 19 |
| | x135m1 (G12V)** | 27 | 20 |
| HLA-A11+ G12V− | PANC-1 (HLA-A11+, G12D)** | 16 | 17 |
| | Barr (HLA-A11+, G12R)* | 17 | 22 |
| | Medium | 18 | 16 |

*Mutation (or lack thereof, i.e., "WT") determined by genotyping.
**Mutation determined by genotyping and mRNA expression (see Tables 13 and 20).

Example 10

This example demonstrates the correlation between IFN-γ production and mutated KRAS expression for the TRAV3-3*01/BV4*01 murine anti-KRAS G12V TCR (SEQ ID NOs: 133 and 134).

The number of copies of KRAS G12V mRNA expressed by each of the pancreatic tumor cell lines shown in Table 13 was measured and compared to the number of copies of β-actin mRNA expressed by the indicated cell line (Table 13). The amount of IFN-γ secreted by the PBL transduced with the TRAV3-3*01/BV4*01 murine anti-KRAS G12V TCR (SEQ ID NOs: 133 and 134) upon co-culture with each cell line measured in Example 9 is reproduced in Table 13. The reactivity of the TRAV3-3*01/BV4*01 murine anti-KRAS G12V TCR (SEQ ID NOs: 133 and 134) (in terms of IFN-γ secretion upon co-culture with target cells) correlated with the number of copies of KRAS G12V mRNA.

TABLE 13

| | β-actin (Copy number) | Ref Total KRAS (Copy per $10^6$ β-actin) | G12V (Copy per $10^6$ β-actin) | IFN-γ (pg/ml) |
|---|---|---|---|---|
| BxPC3/A11 | $3.13 \times 10^7$ | $6.84 \times 10^3$ | 2.51 | 25 |
| MiaPaca2/A11 | $2.01 \times 10^7$ | $5.87 \times 10^3$ | $1.06 \times 10^{-1}$ | 16 |
| Capan-1/A11 | $2.28 \times 10^7$ | $5.92 \times 10^3$ | $5.42 \times 10^3$ | 99 |
| CFPAC-1/A11 | $1.96 \times 10^7$ | $2.09 \times 10^4$ | $3.72 \times 10^3$ | 224 |
| Paca44/A11 | $1.80 \times 10^7$ | $4.94 \times 10^3$ | $3.62 \times 10^3$ | 577 |
| SK.PC3/A11 | $3.28 \times 10^7$ | $1.48 \times 10^4$ | $1.42 \times 10^4$ | 7947 |
| x135m1/A11 | $8.50 \times 10^6$ | $8.75 \times 10^3$ | $9.85 \times 10^3$ | 1020 |

Example 11

This example demonstrates that the TRAV3-3*01/BV4*01 murine anti-KRAS G12V TCR (SEQ ID NOs: 133 and 134) recognizes mutated KRAS either (i) in the presence of CD4 and the absence of CD8 or (ii) in the presence of CD8 and the absence of CD4.

PBL were transduced with a nucleotide sequence encoding the TRAV3-3*01/BV4*01 murine anti-KRAS G12V TCR (SEQ ID NOs: 133 and 134). Transduced cells were sorted into the populations shown in Table 14 by flow cytometry. The sorted populations of cells were co-cultured with (i) COS7/A11 cells transduced with a (a) G12D minigene (encoding 163-mer) (COS/A11/G12D), (b) G12V minigene (encoding 163-mer) (COS/A11/G12V), or (c) WT KRAS minigene (encoding 163-mer) (COS/A11/WT); or (ii) SK.PC3 pancreatic tumor cell line untransduced or transduced with HLA-A11. Medium without cells served as a negative control. IFN-γ secretion was measured.

The results are shown in Table 14. In Table 14, bold IFN-γ secretion values indicate those target cells for which the TCR demonstrated reactivity. As shown in Table 14, the TRAV3-3*01/BV4*01 murine anti-KRAS G12V TCR (SEQ ID NOs: 133 and 134) recognized target cells either (i) in the presence of CD4 and the absence of CD8 or (ii) in the presence of CD8 and the absence of CD4. Accordingly, the TRAV3-3*01/BV4*01 murine anti-KRAS G12V TCR (SEQ ID NOs: 133 and 134) provides highly avid recognition of the target.

TABLE 14

| PBL transduced with TRAV3-3*01/BV4*01 | IFN-g (pg/ml) | | | | | |
|---|---|---|---|---|---|---|
| | Cos7/A11/WT | Cos7/A11/G12D | Cos7/A11/G12V | SK.PC3 | SK.PC3/A11 | Medium |
| Bulk | 48 | 67 | 8294 | 41 | 8944 | 16 |
| CD8 enriched | 49 | 64 | 8150 | 75 | 8602 | 16 |
| CD4 enriched | 16 | 16 | 763 | 16 | 458 | 16 |
| GFP | 16 | 17 | 16 | 20 | 16 | 16 |

Example 12

This example demonstrates the isolation of murine anti-KRAS$_{7-16}$ G12D 10-mer TCRs.

HLA-A11 transgenic mice were immunized with the G12D 10-mer peptide (SEQ ID NO: 2) three times. After the third immunization, the spleen and lymph nodes were removed and cultured in vitro with the G12D 10-mer peptide at various concentrations (1 µM, 0.1 µM, and 0.01 µM) for seven days. T cells isolated from the LN and spleen cultures were tested for reactivity against (i) COS7 cells transduced to express HLA-A11 (COS7/A11) which had been pulsed with (a) no peptide (none), (b) WT KRAS$_{7-16}$ peptide (SEQ ID NO: 30) (COS/A11+WT peptide), (c) G12D 10-mer peptide (SEQ ID NO: 2) (COS/A11+G12D peptide), (d) G12V 10-mer peptide (SEQ ID NO: 33) (COS/A11+G12V peptide), (e) G12V 9-mer peptide (SEQ ID NO: 35), or (0 G12D 9-mer peptide (SEQ ID NO: 34); and (ii) COS7/A11 cells transfected with a vector encoding a (a) WT KRAS minigene (encoding 23-mer SEQ ID NO: 118) (COS/A11/WT), (b) G12D minigene (encoding 23-mer SEQ ID NO: 119) (COS/A11/G12D), or (c) (b) G12V minigene (encoding 23-mer SEQ ID NO: 120) (COS/A11/G12D). Interferon (IFN)-γ was measured.

The results are shown in Table 15A (peptide pulse) and Table 15B (transfectants). In Tables 15A and 15B, bold IFN-γ secretion values indicate those target peptides and target cells for which the TCR demonstrated reactivity. As shown in Tables 15A and 15B, HLA-A11 restricted murine T cells were reactive against KRAS G12D peptide SEQ ID NO: 2.

TABLE 15A

| Stimulated with G12D10-mer | | Cos7/A11 pulsed (IFN-γ (pg/ml)) | | | | |
|---|---|---|---|---|---|---|
| | | none | WT 10-mer | G12D 9-mer | G12D 10-mer | G12V 9-mer | G12V 10-mer |
| Spleen | 1 µM | 55 | 49 | 121 | >20000 | 54 | 64 |
| | 0.1 µM | 65 | 59 | 120 | 19521 | 65 | 64 |
| | 0.01 µM | 82 | 61 | 87 | 1060 | 66 | 66 |
| LN | 1 µM | 57 | 98 | 807 | >20000 | 68 | 95 |
| | 0.1 µM | 80 | 86 | 375 | >20000 | 108 | 89 |
| | 0.01 µM | 349 | 339 | 435 | >20000 | 296 | 325 |

TABLE 15B

| | | (IFN-γ (pg/ml)) | |
|---|---|---|---|
| | Cos7/A11/WT | Cos7/A11/G12D | Cos7/A11/G12V |
| Spleen | 50 | >20000 | 49 |
| | 53 | >20000 | 59 |
| | 80 | 847 | 81 |
| LN | 71 | >20000 | 75 |
| | 235 | >20000 | 102 |
| | 440 | >20000 | 328 |

T cells isolated from the LN and spleen cultures were also stimulated in vitro with various concentrations of G12D peptides for 6-7 days and were then co-cultured with the HLA-A11-expressing, KRAS G12D+ pancreatic cell lines shown in Table 16. IFN-γ was measured.

The results are shown in Table 16. In Table 16, bold IFN-γ secretion values indicate those target cells for which the TCR demonstrated reactivity. As shown in Table 16, T cells isolated from the LN and spleen cultures were reactive with HLA-A11-expressing, KRAS G12D+ pancreatic cell lines.

TABLE 16

| | stimulated with | IFN-γ (pg/ml) | | | | |
|---|---|---|---|---|---|---|
| | G12D10-mer | Medium | FA6-2/A11 | MDA-Panc48/A11 | Panc-1 | PK.45p/A11 |
| Spleen | 1 µM | 47 | 2134 | 1322 | 48 | 46 |
| | 0.1 µM | 46 | 1588 | 665 | 54 | 54 |
| | 0.01 µM | 59 | 116 | 443 | 54 | 59 |
| LN | 1 µM | 55 | 4614 | 202 | 61 | 57 |
| | 0.1 µM | 121 | 4512 | 211 | 68 | 74 |
| | 0.01 µM | 279 | 3019 | 559 | 96 | 249 |

The TCR was isolated from the reactive cells using 5' RACE. Two dominant alpha chains and one dominant beta chain were identified (Table 17).

TABLE 17

| | V Region | D/J Region | CDR3 | SEQ ID NO: | Frequency |
|---|---|---|---|---|---|
| Alpha chains | TRAV4-4/DV10*01(1) | 49*01 | CAADSSNTGYQNFYF | 151 | 30% |
| | TRAV4-4/DV10*01(2) | 49*01 | CAALNTGYQNFYF | 161 | 10% |
| Beta chains | TRBV12-2*01 | 1*01/1-2*01 | CASSLTDPLDSDYTF | 154 | 18% |

Example 13

This example demonstrates that PBL transduced to express a TCR α chain comprising SEQ ID NO: 157 and a TCR β chain comprising SEQ ID NO: 158 are reactive against HLA-A11+/G12D 10-mer+ targets.

The two dominant α chains and the β chains of Table 17 were individually cloned into MSGV1 retroviral vectors. PBL were individually co-transduced to express one of the two pairs of the α and β chain, as shown in Table 18. Transduced PBL were screened for reactivity against (i) COS7/A11 cells transduced with a (a) G12D minigene (encoding 23-mer SEQ ID NO: 119) (COS/A11/G12D), (b) G12V minigene (encoding 23-mer SEQ ID NO: 120) (COS/A11/G12V), (c) WT KRAS minigene (encoding 23-mer SEQ ID NO: 118) (COS/A11/WT), or (d) no cells (medium only) (Table 18). IFN-γ secretion was measured.

The results are shown in Table 18. As shown in Table 18, PBL co-transduced to express murine TCR α chain TRAV4-4*01(1) (SEQ ID NO: 157) and murine TCR β chain TRBV12-2*01 (SEQ ID NO: 158) demonstrated reactivity against HLA-A11-expressing G12D transfectant target cells.

TABLE 18

| | IFN-γ (pg/ml) | | | |
|---|---|---|---|---|
| | Cos/A11/ WT | Cos/A11/ G1213 | Cos/A11/ G12V | Medium |
| TRAV4-4*01(1)/ TRBV12-2*01 | 31 | 34440 | 32 | 32 |
| TRAV4-4*01(2)/ TRBV12-2*01 | 48 | 79 | 36 | 40 |

PBL were transduced to express the TCR TRAV4-4*01(1)/TRBV12-2*01 (SEQ ID NOs: 157 and 158) and screened for reactivity against COS7/A11 cells transduced with a (a) G12D minigene (encoding 23-mer SEQ ID NO: 119) (COS/A11/G12D), (b) G12V minigene (encoding 23-mer SEQ ID NO: 120) (COS/A11/G12V), (c) WT KRAS minigene (encoding 23-mer SEQ ID NO: 118) (COS/A11/WT), (d) the pancreatic tumor lines shown in Table 19 that were untransduced or transduced to express HLA-A11 and the indicated KRAS mutation. In Table 19, the KRAS mutation expressed by each pancreatic tumor cell line is indicated. IFN-γ secretion was measured.

The results are shown in Table 19. As shown in Table 19, PBL transduced with the TCR TRAV4-4*01(1)/TRBV12-2*01 (SEQ ID NOs: 157 and 158) recognized HLA-A11+ G12D+ pancreatic tumor lines.

TABLE 19

| | IFN-γ (pg/ml) TRAV4-4/DV*01/TRBV12-2*01 |
|---|---|
| Cos/A11/WT | 96 |
| Cos/A11/G12D | 45214 |
| Cos/A11/G12V | 99 |
| BxPC3/A11 (WT)* | 22 |
| MiaPaca2/A11 (G12C)* | 16 |
| SK.PC.3/A11 (G12V)** | 22 |
| T3m4/A11 (Q61H)* | 42 |
| Barr (A11+, G12R)* | 17 |
| AsPC-1/A11 (G12D)** | 7321 |

TABLE 19-continued

| | IFN-γ (pg/ml) TRAV4-4/DV*01/TRBV12-2*01 |
|---|---|
| FA6-2/A11 (G12D)** | 11287 |
| MDA-Panc-48/A11 (G12D)** | 238 |
| PANC-1 (A11+, G12D)** | 114 |
| PK.45p/A11 (G12D)** | 70 |
| BxPC3 | 16 |
| MiaPaca2 | 16 |
| SK.PC.3 | 17 |
| T3m4 | 38 |
| AsPC-1 | 16 |
| FA6-2 | 16 |
| MDA-Panc-48 | 16 |
| PK.45p | 16 |
| Medium | 16 |

*Mutation (or lack thereof, i.e., "WT") determined by genotyping.
**Mutation determined by genotyping and mRNA expression (see Tables 13 and 20).

Example 14

This example demonstrates the correlation between IFN-γ production and mutated KRAS expression for the TRAV4-4*01(1)/TRBV12-2*01 murine anti-KRAS G12D TCR (SEQ ID NOs: 157 and 158).

The number of copies of KRAS G12D mRNA expressed by each of the pancreatic tumor cell lines shown in Table 20 was measured and compared to the number of copies of β-actin mRNA expressed by each cell line (Table 20). The amount of IFN-γ secreted by the PBL transduced with the TRAV4-4*01(1)/TRBV12-2*01 murine anti-KRAS G12D TCR (SEQ ID NOs: 157 and 158) upon co-culture with each cell line is shown in Table 13. The reactivity of the TRAV4-4*01(1)/TRBV12-2*01 murine anti-KRAS G12D TCR (SEQ ID NOs: 157 and 158) (in terms of IFN-γ secretion upon co-culture with target cells) was correlated with the number of copies of KRAS G12D mRNA.

TABLE 20

| | β-actin (Copy number) | Ref Total KRAS (Copy per $10^6$ β-actin) | G12D (Copy per $10^6$ β-actin) | IFN-γ (pg/ml) |
|---|---|---|---|---|
| BxPC3/A11 | $3.13 \times 10^7$ | $6.22 \times 10^3$ | $2.91 \times 10^1$ | 26 |
| Barr | $1.88 \times 10^7$ | $7.98 \times 10^3$ | $2.41 \times 10^{-1}$ | 43 |
| T3m4/A11 | $3.40 \times 10^7$ | $1.56 \times 10^4$ | $5.26 \times 10^{-1}$ | 49 |
| ASPC-1/A11 | $2.69 \times 10^7$ | $1.40 \times 10^4$ | $5.99 \times 10^3$ | 7320 |
| FA6-2/A11 | $3.01 \times 10^7$ | $1.1 \times 10^5$ | $3.99 \times 10^4$ | 31688 |
| MDA-Panc-48/A11 | $4.56 \times 10^7$ | $4.01 \times 10^3$ | $1.90 \times 10^3$ | 433 |
| PANC-1 | $3.48 \times 10^7$ | $1.39 \times 10^4$ | $4.28 \times 10^3$ | 17 |
| PK.45p/A11 | $4.04 \times 10^7$ | $1.66 \times 10^4$ | $2.80 \times 10^2$ | 52 |

Example 15

This example demonstrates that the TRAV4-4/DV10*01/BV12-2*01 murine anti-KRAS G12D TCR (SEQ ID NOs: 157 and 158) has a higher affinity for pulsed target peptide as compared to the TRAV12N-3*01/BV4*01 murine anti-KRAS G12D TCR (SEQ ID NOs: 11 and 12).

PBL were transduced with either (i) T TRAV4-4/DV10*01/BV12-2*01 murine anti-KRAS G12D TCR (SEQ ID NOs: 157 and 158) or (ii) TRAV12N-3*01/BV4*01 murine anti-KRAS G12D TCR (SEQ ID NOs: 11 and 12). Transduced cells were co-cultured with Cos7/A11 cells pulsed with (a) G12D 10-mer peptide (SEQ ID NO: 2), (b)

WT KRAS 10-mer peptide (SEQ ID NO: 30), (c) G12D 9-mer peptide (SEQ ID NO: 34), or (d) WT KRAS 9-mer peptide (SEQ ID NO: 31) at the concentrations shown in Tables 21A and 21B. IFN-γ secretion was measured.

The results are shown in Table 21A (TRAV4-4/DV10*01/BV12-2*0 (SEQ ID NOs: 157 and 158)) and Table 21B (TRAV12N-3*01/BV4*01 (SEQ ID NOs: 11 and 12)). As shown in Tables 21A-21B, T cells transduced with the TRAV4-4/DV10*01/BV12-2*0 (SEQ ID NOs: 157 and 158) recognized 10-mer at pulsed at a concentration of $1\times10^{-9}$ M. Accordingly, the TRAV4-4/DV10*01/BV12-2*0 (SEQ ID NOs: 157 and 158) recognized pulsed target peptide with a higher avidity as compared to the TRAV12N-3*01/BV4*01 (SEQ ID NOs: 11 and 12) TCR.

TABLE 21A

| Peptide concentration ($10^{*}$M) | IFN-γ (pg/ml) | | | |
| --- | --- | --- | --- | --- |
| | WT 9-mer | WT 10-mer | G12D 9-mer | G12D 10-mer |
| −6 | 54 | 56 | 131 | 27407 |
| −7 | 53 | 57 | 60 | 29508 |
| −8 | 59 | 51 | 47 | 6131 |
| −9 | 54 | 51 | 53 | 2075 |
| −10 | 51 | 54 | 53 | 402 |
| −11 | 48 | 50 | 52 | 63 |
| −12 | 52 | 44 | 58 | 50 |
| −13 | 51 | 54 | 51 | 51 |

TABLE 21B

| Peptide concentration ($10^{*}$M) | IFN-g (pg/ml) | | | |
| --- | --- | --- | --- | --- |
| | WT 9-mer | WT 10-mer | G12D 9-mer | G12D 10-mer |
| −6 | 90 | 82 | 125 | 18948 |
| −7 | 96 | 77 | 86 | 11623 |
| −8 | 95 | 85 | 90 | 3852 |
| −9 | 88 | 102 | 92 | 108 |
| −10 | 95 | 88 | 95 | 212 |
| −11 | 84 | 81 | 88 | 103 |
| −12 | 105 | 76 | 91 | 93 |
| −13 | 103 | 92 | 84 | 93 |

Example 16

This example demonstrates that the TRAV4-4/DV10*01/BV12-2*01 murine anti-KRAS G12D TCR (SEQ ID NOs: 157 and 158) has a higher affinity for G12D+ pancreatic tumor cell lines as compared to TRAV12N-3*01/BV4*01 murine anti-KRAS G12D TCR (SEQ ID NOs: 11 and 12).

PBL were transduced with either (i) TRAV4-4/DV10*01/BV12-2*01 murine anti-KRAS G12D TCR (SEQ ID NOs: 157 and 158) or (ii) TRAV12N-3*01/BV4*01 murine anti-KRAS G12D TCR (SEQ ID NOs: 11 and 12). Transduced cells were co-cultured with pancreatic cell lines that were untransduced or transduced with HLA-A11 and mutated KRAS as shown in Table 22. IFN-γ secretion was measured.

The results are shown in Table 22. As shown in Table 22, T cells transduced with the TRAV4-4/DV10*01/BV12-2*0 (SEQ ID NOs: 157 and 158) recognized G12D+ pancreatic tumor cell lines with a higher avidity as compared to the TRAV12N-3*01/BV4*01 (SEQ ID NOs: 11 and 12) TCR.

TABLE 22

| | IFN-g (pg/ml) | |
| --- | --- | --- |
| | TRAV4-4/DV10*01/ BV12-2*01 | TRAV12N-3*01/ BV4*01 |
| BxPC3/A11 (WT)* | 28 | 37 |
| MiaPaca2/A11 (G12C)* | 27 | 57 |
| SK.PC.3/A11 (G12V)** | 41 | 44 |
| T3m4/A11 (Q61H)* | 42 | 135 |
| Barr (A11+, G12R)* | 31 | 21 |
| AsPC-1/A11 (G12D)** | 7478 | 980 |
| FA6-2/A11 (G12D)** | 8027 | 1494 |
| MDA-Panc-48/A11 (G12D)** | 362 | 66 |
| PANC-1 (A11+, G12D)** | 148 | 34 |
| PK.45p/A11 (G12D)** | 52 | 113 |
| AsPC-1 | 24 | 16 |
| FA6-2 | 41 | 26 |
| MDA-Panc-48 | 43 | 134 |
| PK.45p | 31 | 35 |
| Medium | 28 | 20 |

*Mutation (or lack thereof, i.e., "WT") determined by genotyping.
**Mutation determined by genotyping and mRNA expression (see Tables 13 and 20).

Example 17

This example demonstrates a Phase I/II study administering PBL transduced with a vector encoding the murine TCR recognizing mutated KRAS to patients with mutated KRAS-expressing cancer.

To be eligible for inclusion in the study, patients meet the normal criteria for adoptive cell therapy (ACT)/IL-2 and have the following:

an HLA-A11+, mutated KRAS-expressing tumor (as measured by immunohistochemistry);

radioiodine-refractory cancer; and a positron emission tomography (PET) avid tumor or demonstrate tumor progression within the last 6 months.

Autologous PBL are retovirally transduced with a vector encoding the alpha and beta chains of the murine anti-mutated KRAS TCR (SEQ ID NOs: 11 and 12). The patient is treated with preparative, non-myeloablative, high-dose cyclophosphamide (Cy) and fludarabine (Flu). The patient is treated with high-dose, IL-2 every eight hours until tolerance. In Phase I, the patient is treated with a starting dose of $1\times10^{8}$ retrovirally transduced cells. The dose is increased by half-logs, with one patient per cohort up to a dose of $1\times10^{10}$ cells, followed by three patients per cohort. Phase II has a two-stage design with a targeted response rate of 20%.

Example 18

This example demonstrates the frequency of KRAS mutations in human cancers.

The frequency (%) of KRAS mutations in various human cancers is set forth in Table 23. Table 23 also shows the frequency (%) of specific KRAS mutations among all KRAS mutations.

TABLE 23

| Tumor | Frequency of KRAS mutation | G12A | G12D | G12R | G12C | G12S | G12V | G13D |
|---|---|---|---|---|---|---|---|---|
| | | % of all KRAS mutations | | | | | | |
| Pancreatic carcinoma | 70% | 2 | 51 | 12 | 3 | 2 | 30 | 1 |
| Colorectal | 36% | 7 | 34 | 1 | 9 | 5 | 24 | 19 |
| Lung adenocarcinoma | 20% | 7 | 17 | 2 | 42 | 5 | 20 | 2 |
| Endometrial | 18% | 11 | 36 | 0 | 9 | 2 | 24 | 15 |
| Epithelial ovarian cancer | 14% | 4 | 41 | 2 | 5 | 0 | 37 | 5 |
| Prostate | 7% | 2 | 22 | 1 | 10 | 3 | 35 | 23 |

Example 19

This example demonstrates that a substitution of the glycine residue in the CDR3α region of the TRAV4-4/DV10*01/BV12-2*01 TCR provides enhanced anti-KRAS reactivity as compared to the wild-type TRAV4-4/DV10*01/BV12-2*01 TCR.

The glycine residue in the CDR3α region of the TRAV4-4/DV10*01/BV12-2*01 TCR was replaced with an alanine residue to provide a substituted TRAV4-4/DV10*01/BV12-2*01 TCR (CDR3alpha G112A). PBL were transduced with either (i) wild-type TRAV4-4/DV10*01/BV12-2*01 TCR (SEQ ID NOs: 157 and 158) or (ii) substituted TRAV4-4/DV10*01/BV12-2*01 TCR (SEQ ID NOs: 209 and 158). Transduced cells were co-cultured with Cos cells transduced with HLA-A11 and WT KRAS (Cos/A11/WT), Cos cells transduced with HLA-A11 and G12D KRAS (Cos/A11/G12D), pancreatic tumor cell line FA6-2 transduced with HLA-A11 (FA6-2/A11), or pancreatic tumor cell line Panc-1. Transduced cells cultured alone (medium) served as control. IFN-γ secretion (pg/ml) was measured. The results are shown in Table 24.

TABLE 24

| | WT TRAV4-4/DV10*01/BV12-2*01 (SEQ ID NOs: 157 and 158) | Substituted TRAV4-4/DV10*01/BV12-2*01 (CDR3alpha G112A) (SEQ ID NOs: 209 and 158) |
|---|---|---|
| Cos/A11/WT | 51 | 64 |
| COs/A11/G12D | 465 | 634 |
| FA6-2/A11 | 2628 | 3631 |
| Panc-1 | 37 | 33 |
| Medium | 48 | 37 |

As shown in Table 24, a substitution of the glycine residue in the CDR3α region of the TRAV4-4/DV10*01/BV12-2*01 TCR provided enhanced anti-KRAS reactivity as compared to the wild-type TRAV4-4/DV10*01/BV12-2*01 TCR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T cell receptor (TCR) having antigenic specificity for a mutated epitope, the amino acid sequence of the mutated epitope consisting of the amino acid sequence of VVVGADGVGK (SEQ ID NO: 2),
  wherein the TCR has antigenic specificity for the mutated epitope presented in the context of an HLA-A11 molecule, and wherein the TCR comprises:
  (a) an α chain complementarity determining region (CDR) 1 comprising the amino acid sequence of SEQ ID NO: 3, an α chain CDR2 comprising the amino acid sequence of SEQ ID NO: 4, an α chain CDR3 comprising the amino acid sequence of SEQ ID NO: 5, a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8; and
  (b) an α chain constant region comprising an amino acid sequence at least 90% identical to the amino acid sequence of SEQ ID NO: 13 and a β chain constant region comprising an amino acid sequence at least 90% identical to the amino acid sequence of SEQ ID NO: 14.

2. An isolated or purified nucleic acid comprising a nucleotide sequence encoding the TCR of claim 1.

3. A recombinant expression vector comprising the nucleic acid of claim 2.

4. An isolated host cell comprising the recombinant expression vector of claim 3.

5. The host cell of claim 4, wherein the cell is human.

6. The host cell of claim 5, wherein the cell is a T cell.

7. A population of cells comprising at least one host cell of claim 6.

8. A pharmaceutical composition comprising the TCR of claim 1 or a nucleic acid comprising a nucleotide sequence encoding the TCR of claim 1 and a pharmaceutically acceptable carrier.

9. A method of treating cancer in a mammal, the method comprising administering to the mammal the population of cells of claim 7 in an amount effective to treat or prevent a cancer expressing a mutated epitope comprising the amino acid sequence of VVVGADGVGK (SEQ ID NO: 2) in the mammal.

10. The method of claim 9, wherein the mammal is a human.

11. The method of claim 9, wherein the cancer is pancreatic, colorectal, lung, endometrial, ovarian, or prostate cancer.

12. A method of detecting the presence of a cancer expressing a mutated epitope comprising the amino acid sequence of VVVGADGVGK (SEQ ID NO: 2) in a mammal, the method comprising contacting a sample comprising one or more cells from the mammal with the TCR of claim 1, thereby forming a complex, and
  detecting the complex, wherein detection of the complex is indicative of the presence of the cancer in the mammal.

13. The method of claim 12, wherein the mammal is a human.

14. The method of claim 12, wherein the cancer is pancreatic, colorectal, lung, endometrial, ovarian, or prostate cancer.

15. The TCR of claim 1, wherein the TCR comprises an α chain comprising an amino acid sequence at least 90% identical to the amino acid sequence of SEQ ID NO: 11.

16. The TCR of claim 1, wherein the TCR comprises a β chain comprising an amino acid sequence at least 90% identical to the amino acid sequence of SEQ ID NO: 12.

17. An isolated or purified polypeptide comprising a functional portion of the TCR of claim 1, wherein the functional portion comprises the amino acid sequences of SEQ ID NOs: 3-8.

18. An isolated or purified protein comprising a first polypeptide chain comprising the amino acid sequences of SEQ ID NOs: 3-5 and a second polypeptide chain comprising the amino acid sequences of SEQ ID NOs: 6-8.

* * * * *

SEQUENCE LISTING

<160> NUMBER OF SEQ ID NOS: 209

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
                180                 185

<210> SEQ ID NO 2
<211> LENGTH: 10
<212> TYPE: PRT
<213> ORGANISM: Homo sapiens

<400> SEQUENCE: 2

Val Val Val Gly Ala Asp Gly Val Gly Lys
1               5                   10

<210> SEQ ID NO 3
<211> LENGTH: 7
<212> TYPE: PRT
<213> ORGANISM: Mus musculus

<400> SEQUENCE: 3

Thr Ile Tyr Ser Asn Pro Phe
1               5

<210> SEQ ID NO 4
<211> LENGTH: 7
<212> TYPE: PRT
<213> ORGANISM: Mus musculus

<400> SEQUENCE: 4

Ser Phe Thr Asp Asn Lys Arg
1               5

<210> SEQ ID NO 5
<211> LENGTH: 13
<212> TYPE: PRT
<213> ORGANISM: Mus musculus

<400> SEQUENCE: 5

Cys Ala Leu Arg Gly Asn Ala Gly Ala Lys Leu Thr Phe
1               5                   10

<210> SEQ ID NO 6
<211> LENGTH: 5
<212> TYPE: PRT
<213> ORGANISM: Mus musculus

<400> SEQUENCE: 6

Leu Gly His Asp Thr
1               5

<210> SEQ ID NO 7
<211> LENGTH: 6
<212> TYPE: PRT
<213> ORGANISM: Mus musculus

<400> SEQUENCE: 7

Tyr Asn Asn Lys Gln Leu
1               5

<210> SEQ ID NO 8
<211> LENGTH: 15
<212> TYPE: PRT
<213> ORGANISM: Mus musculus

<400> SEQUENCE: 8

Cys Ala Ser Ser Ser Arg Asp Trp Ser Ala Glu Thr Leu Tyr Phe
1               5                   10                  15

<210> SEQ ID NO 9
<211> LENGTH: 135
<212> TYPE: PRT
<213> ORGANISM: Mus musculus

<400> SEQUENCE: 9

Met Arg Pro Val Thr Cys Ser Val Leu Val Leu Leu Met Leu Arg
1               5                   10                  15

Arg Ser Asn Gly Asp Gly Asp Ser Val Thr Gln Thr Glu Gly Leu Val
                20                  25                  30

Thr Leu Thr Glu Gly Leu Pro Val Met Leu Asn Cys Thr Tyr Gln Thr
            35                  40                  45

Ile Tyr Ser Asn Pro Phe Leu Phe Trp Tyr Val Gln His Leu Asn Glu
        50                  55                  60

Ser Pro Arg Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Ala Gly Ala Lys Leu Thr Phe Gly Gly Gly Thr
        115                 120                 125

Arg Leu Thr Val Arg Pro Asp
    130                 135

<210> SEQ ID NO 10
<211> LENGTH: 134
<212> TYPE: PRT
<213> ORGANISM: Mus musculus

<400> SEQUENCE: 10

Met Gly Cys Arg Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Ala Glu Thr Leu Tyr Phe Gly Ser Gly Thr
        115                 120                 125

Arg Leu Thr Val Leu Glu
    130

<210> SEQ ID NO 11
<211> LENGTH: 271
<212> TYPE: PRT
<213> ORGANISM: Mus musculus

<400> SEQUENCE: 11

Met Arg Pro Val Thr Cys Ser Val Leu Val Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Ala Gly Ala Lys Leu Thr Phe Gly Gly Gly Thr
        115                 120                 125

Arg Leu Thr Val Arg Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

```
Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
            245                 250                 255

Val Ala Gly Phe Asn Leu Leu Met Thr Leu Arg Leu Trp Ser Ser
260                 265                 270

<210> SEQ ID NO 12
<211> LENGTH: 306
<212> TYPE: PRT
<213> ORGANISM: Mus musculus

<400> SEQUENCE: 12

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
            35                  40                  45

Asp Thr Met Tyr Trp Tyr Lys Gln Asp Ser Lys Lys Leu Leu Lys Ile
50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Ala Glu Thr Leu Tyr Phe Gly Ser Gly Thr
            115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Gly Leu Val Leu Met Ala Met Val Lys Lys Lys
290                 295                 300
```

Asn Ser
305

<210> SEQ ID NO 13
<211> LENGTH: 136
<212> TYPE: PRT
<213> ORGANISM: Mus musculus

<400> SEQUENCE: 13

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
                20                  25                  30

Val Pro Lys Thr Met Glu Ser Gly Thr Phe Ile Thr Asp Lys Thr Val
            35                  40                  45

Leu Asp Met Lys Ala Met Asp Ser Lys Ser Asn Gly Ala Ile Ala Trp
        50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
                100                 105                 110

Met Gly Leu Arg Ile Leu Leu Leu Lys Val Ala Gly Phe Asn Leu Leu
            115                 120                 125

Met Thr Leu Arg Leu Trp Ser Ser
        130                 135

<210> SEQ ID NO 14
<211> LENGTH: 172
<212> TYPE: PRT
<213> ORGANISM: Mus musculus

<400> SEQUENCE: 14

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
                20                  25                  30

Arg Gly Phe Phe Pro Asp His Val Glu Leu Ser Trp Trp Val Asn Gly
            35                  40                  45

Lys Glu Val His Ser Gly Val Ser Thr Asp Pro Gln Ala Tyr Lys Glu
        50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95

Gly Leu Ser Glu Glu Asp Lys Trp Pro Glu Gly Ser Pro Lys Pro Val
                100                 105                 110

Thr Gln Asn Ile Ser Ala Glu Ala Trp Gly Arg Ala Asp Cys Gly Ile
            115                 120                 125

Thr Ser Ala Ser Tyr His Gln Gly Val Leu Ser Ala Thr Ile Leu Tyr
        130                 135                 140

Glu Ile Leu Leu Gly Lys Ala Thr Leu Tyr Ala Val Leu Val Ser Gly
145                 150                 155                 160

Leu Val Leu Met Ala Met Val Lys Lys Lys Asn Ser
                165                 170

<210> SEQ ID NO 15
<211> LENGTH: 403
<212> TYPE: DNA
<213> ORGANISM: Artificial Sequence
<220> FEATURE:
<223> OTHER INFORMATION: Synthetic

<400> SEQUENCE: 15

| | |
|---|---|
| atgcgtcctg tcacctgctc agttcttgtg ctcctcctaa tgctcaggag gagcaatggc | 60 |
| gatggagact ccgtgaccca gacagaaggc ctggtcactc tcacagaagg gttgcctgtg | 120 |
| atgctgaact gcacctatca gactatttac tcaaatcctt ccttttctg gtatgtgcaa | 180 |
| catctcaatg aatcccctcg gctactcctg aagagcttca cagacaacaa gaggaccgag | 240 |
| caccaagggt tccacgccac tctccataag agcagcagct ccttccatct gcagaagtcc | 300 |
| tcagcgcagc tgtcagactc tgccctgtac tactgtgctc tgaggggaa tgcaggtgcc | 360 |
| aagctcacat cggaggggg aacaaggtta acggtcagac ccg | 403 |

<210> SEQ ID NO 16
<211> LENGTH: 400
<212> TYPE: DNA
<213> ORGANISM: Artificial Sequence
<220> FEATURE:
<223> OTHER INFORMATION: Synthetic

<400> SEQUENCE: 16

| | |
|---|---|
| atgggctgta ggctcctaag ctgtgtggcc ttctgcctct tgggaatagg ccctttggag | 60 |
| acggctgttt tccagactcc aaactatcat gtcacacagg tgggaaatga agtgtctttc | 120 |
| aattgtaagc aaactctggg ccacgatact atgtattggt acaagcaaga ctctaagaaa | 180 |
| ttgctgaaga ttatgtttag ctacaataat aagcaactca ttgtaaacga aacagttcca | 240 |
| aggcgcttct cacctcagtc ttcagataaa gctcatttga atcttcgaat caagtctgta | 300 |
| gagccggagg actctgctgt gtatctctgt gccagcagct cccgggactg gagtgcagaa | 360 |
| acgctgtatt ttggctcagg aaccagactg actgttctcg | 400 |

<210> SEQ ID NO 17
<211> LENGTH: 816
<212> TYPE: DNA
<213> ORGANISM: Artificial Sequence
<220> FEATURE:
<223> OTHER INFORMATION: Synthetic

<400> SEQUENCE: 17

| | |
|---|---|
| atgcgtcctg tcacctgctc agttcttgtg ctcctcctaa tgctcaggag gagcaatggc | 60 |
| gatggagact ccgtgaccca gacagaaggc ctggtcactc tcacagaagg gttgcctgtg | 120 |
| atgctgaact gcacctatca gactatttac tcaaatcctt ccttttctg gtatgtgcaa | 180 |
| catctcaatg aatcccctcg gctactcctg aagagcttca cagacaacaa gaggaccgag | 240 |
| caccaagggt tccacgccac tctccataag agcagcagct ccttccatct gcagaagtcc | 300 |
| tcagcgcagc tgtcagactc tgccctgtac tactgtgctc tgaggggaa tgcaggtgcc | 360 |
| aagctcacat cggaggggg aacaaggtta acggtcagac ccgacatcca gaacccagaa | 420 |
| cctgctgtgt accagttaaa agatcctcgg tctcaggaca gcaccctctg cctgttcacc | 480 |
| gactttgact cccaaatcaa tgtgccgaaa accatggaat ctggaacgtt catcactgac | 540 |
| aaaactgtgc tggacatgaa agctatggat tccaagagca tggggccat tgcctggagc | 600 |

```
aaccagacaa gcttcacctg ccaagatatc ttcaaagaga ccaacgccac ctaccccagt    660
tcagacgttc cctgtgatgc cacgttgact gagaaaagct tgaaacaga tatgaaccta    720 aactttcaaa acctgtcagt tatgggactc cgaatcctcc tgctgaaagt agccggattt    780
aacctgctca tgacgctgag gctgtggtcc agttga                              816

<210> SEQ ID NO 18
<211> LENGTH: 921
<212> TYPE: DNA
<213> ORGANISM: Artificial Sequence
<220> FEATURE:
<223> OTHER INFORMATION: Synthetic

<400> SEQUENCE: 18
atgggctgta ggctcctaag ctgtgtggcc ttctgcctct tgggaatagg ccctttggag     60
acggctgttt tccagactcc aaactatcat gtcacacagg tgggaaatga agtgtctttc    120
aattgtaagc aaactctggg ccacgatact atgtattggt acaagcaaga ctctaagaaa    180
ttgctgaaga ttatgtttag ctacaataat aagcaactca ttgtaaacga acagttcca     240 aggcgcttct cacctcagtc ttcagataaa gctcatttga atcttcgaat caagtctgta    300
gagccggagg actctgctgt gtatctctgt gccagcagcc cccgggactg gagtgcagaa    360
acgctgtatt ttggctcagg aaccagactg actgttctcg aggatctgag aaatgtgact    420
ccacccaagg tctccttgtt tgagccatca aaagcagaga ttgcaaacaa acaaaaggct    480
accctcgtgt gcttggccag ggcttcttc cctgaccacg tggagctgag ctggtgggtg      540
aatggcaagg aggtccacag tggggtcagc acggaccctc aggcctacaa ggagagcaat    600
tatagctact gcctgagcag ccgcctgagg gtctctgcta ccttctggca caatcctcga    660
aaccacttcc gctgccaagt gcagttccat gggctttcag aggaggacaa gtggccagag    720
ggctcaccca aacctgtcac acagaacatc agtgcagagg cctggggccg agcagactgt    780
ggaatcactt cagcatccta tcatcagggg gttctgtctg caaccatcct ctatgagatc    840
ctactgggga aggccaccct atatgctgtg ctggtcagtg gcctggtgct gatggccatg    900
gtcaagaaaa aaaattcctg a                                              921

<210> SEQ ID NO 19
<211> LENGTH: 413
<212> TYPE: DNA
<213> ORGANISM: Artificial Sequence
<220> FEATURE:
<223> OTHER INFORMATION: Synthetic

<400> SEQUENCE: 19
acatccagaa cccagaacct gctgtgtacc agttaaaaga tcctcggtct caggacagca     60
ccctctgcct gttcaccgac tttgactccc aaatcaatgt gccgaaaacc atggaatctg    120
gaacgttcat cactgacaaa actgtgctgg acatgaaagc tatggattcc aagagcaatg    180
gggccattgc ctggagcaac cagacaagct tcacctgcca agatatcttc aaagagacca    240
acgccaccta ccccagttca gacgttccct gtgatgccac gttgactgag aaaagctttg    300
aaacagatat gaacctaaac tttcaaaacc tgtcagttat gggactccga atcctcctgc    360
tgaaagtagc cggatttaac ctgctcatga cgctgaggct gtggtccagt tga           413

<210> SEQ ID NO 20
<211> LENGTH: 521
<212> TYPE: DNA
<213> ORGANISM: Artificial Sequence
```

```
<220> FEATURE:
<223> OTHER INFORMATION: Synthetic

<400> SEQUENCE: 20
aggatctgag aaatgtgact ccacccaagg tctccttgtt tgagccatca aaagcagaga      60
ttgcaaacaa acaaaaggct accctcgtgt gcttggccag gggcttcttc cctgaccacg     120
tggagctgag ctggtgggtg aatggcaagg aggtccacag tggggtcagc acggaccctc     180
aggcctacaa ggagagcaat tatagctact gcctgagcag ccgcctgagg gtctctgcta     240
ccttctggca caatcctcga aaccacttcc gctgccaagt gcagttccat gggctttcag     300
aggaggacaa gtggccagag ggctcaccca aacctgtcac acagaacatc agtgcagagg     360
cctggggccg agcagactgt ggaatcactt cagcatccta tcatcagggg gttctgtctg     420
caaccatcct ctatgagatc ctactgggga aggccaccct atatgctgtg ctggtcagtg     480
gcctagtgct gatggccatg gtcaagaaaa aaaattcctg a                        521

<210> SEQ ID NO 21
<211> LENGTH: 1815
<212> TYPE: DNA
<213> ORGANISM: Artificial Sequence
<220> FEATURE:
<223> OTHER INFORMATION: Synthetic

<400> SEQUENCE: 21
atgcgtcctg tcacctgctc agttcttgtg ctcctcctaa tgctcaggag gagcaatggc      60
gatggagact ccgtgaccca gacagaaggc ctggtcactc tcacagaagg gttgcctgtg     120
atgctgaact gcacctatca gactatttac tcaaatcctt tccttttctg gtatgtgcaa     180
catctcaatg aatcccctcg gctactcctg aagagcttca gacaacaa gaggaccgag       240 caccaagggt tccacgccac tctccataag agcagcagct ccttccatct gcagaagtcc     300
tcagcgcagc tgtcagactc tgccctgtac tactgtgctc tgaggggaa tgcaggtgcc      360 aagctcacat tcggagggggg aacaaggtta acggtcagac ccgacatcca gaacccagaa    420
cctgctgtgt accagttaaa agatcctcgg tctcaggaca gcacccctctg cctgttcacc    480 gactttgact cccaaatcaa tgtgccgaaa accatgaat ctggaacgtt catcactgac      540
aaaactgtgc tggacatgaa agctatggat tccaagagca tggggccat tgcctggagc     600 aaccagacaa gcttcacctg ccaagatatc ttcaaagaga ccaacgccac ctaccccagt     660
tcagacgttc cctgtgatgc cacgttgact gagaaaagct ttgaaacaga tatgaaccta    720
aactttcaaa acctgtcagt tatgggactc cgaatcctcc tgctgaaagt agccggattt    780
aacctgctca tgacgctgag gctgtggtcc agtcgggcca agcggtccgg atccggagcc    840
accaacttca gcctgctgaa gcaggccggc gacgtggagg agaaccccgg ccccatgggc    900
tgtaggctcc taagctgtgt ggccttctgc ctcttgggaa taggccctt ggagacggct    960 gttttccaga ctccaaacta tcatgtcaca caggtgggaa atgaagtgtc tttcaattgt   1020
aagcaaactc tgggccacga tactatgtat tggtacaagc aagactctaa gaaattgctg   1080
aagattatgt ttagctacaa taataagcaa ctcattgtaa acgaaacagt tccaaggcgc   1140
ttctcacctc agtcttcaga taagctcat ttgaatcttc gaatcaagtc tgtagagccg   1200
gaggactctg ctgtgtatct ctgtgccagc agctcccggg actggagtgc agaaacgctg   1260
tattttggct caggaaccag actgactgtt ctcgaggatc tgagaaatgt gactccaccc   1320
aaggtctcct tgtttgagcc atcaaaagca gagattgcaa acaaacaaaa ggctaccctc   1380
```

```
gtgtgcttgg ccaggggctt cttccctgac cacgtggagc tgagctggtg ggtgaatggc    1440
aaggaggtcc acagtggggt cagcacggac cctcaggcct acaaggagag caattatagc    1500
tactgcctga gcagccgcct gagggtctct gctaccttct ggcacaatcc tcgaaaccac    1560
ttccgctgcc aagtgcagtt ccatgggctt tcagaggagg acaagtggcc agagggctca    1620
cccaaacctg tcacacagaa catcagtgca gaggcctggg gccgagcaga ctgtggaatc    1680
acttcagcat cctatcatca ggggttctg tctgcaacca tcctctatga gatcctactg     1740
gggaaggcca ccctatatgc tgtgctggtc agtggcctgg tgctgatggc catggtcaag    1800
aaaaaaaatt cctga                                                     1815

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
actatttact caaatccttt c                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
agcttcacag acaacaagag g                                              21

<210> SEQ ID NO 24
<211> LENGTH: 33
<212> TYPE: DNA
<213> ORGANISM: Artificial Sequence
<220> FEATURE:
<223> OTHER INFORMATION: Synthetic

<400> SEQUENCE: 24
gctctgaggg ggaatgcagg tgccaagctc aca                                 33

<210> SEQ ID NO 25
<211> LENGTH: 15
<212> TYPE: DNA
<213> ORGANISM: Artificial Sequence
<220> FEATURE:
<223> OTHER INFORMATION: Synthetic

<400> SEQUENCE: 25
ctgggccacg atact                                                     15

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
tacaataata agcaactc                                                  18

<210> SEQ ID NO 27
<211> LENGTH: 39
```

```
<212> TYPE: DNA
<213> ORGANISM: Artificial Sequence
<220> FEATURE:
<223> OTHER INFORMATION: Synthetic

<400> SEQUENCE: 27
gccagcagct cccgggactg gagtgcagaa acgctgtat                               39

<210> SEQ ID NO 28
<211> LENGTH: 27
<212> TYPE: PRT
<213> ORGANISM: Artificial Sequence
<220> FEATURE:
<223> OTHER INFORMATION: Synthetic

<400> SEQUENCE: 28

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 29
<211> LENGTH: 189
<212> TYPE: PRT
<213> ORGANISM: Homo sapiens

<400> SEQUENCE: 29

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 30
<211> LENGTH: 10
<212> TYPE: PRT
<213> ORGANISM: Homo sapiens

<400> SEQUENCE: 30

Val Val Val Gly Ala Gly Gly Val Gly Lys
1               5                   10
```

<210> SEQ ID NO 31
<211> LENGTH: 9
<212> TYPE: PRT
<213> ORGANISM: Homo sapiens

<400> SEQUENCE: 31

Val Val Gly Ala Gly Gly Val Gly Lys
1               5

<210> SEQ ID NO 32
<211> LENGTH: 189
<212> TYPE: PRT
<213> ORGANISM: Homo sapiens

<400> SEQUENCE: 32

Met Thr Glu Tyr Lys Leu Val Val Gly Ala Val Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 33
<211> LENGTH: 10
<212> TYPE: PRT
<213> ORGANISM: Homo sapiens

<400> SEQUENCE: 33

Val Val Val Gly Ala Val Gly Val Gly Lys
1               5                   10

<210> SEQ ID NO 34
<211> LENGTH: 9
<212> TYPE: PRT
<213> ORGANISM: Homo sapiens

<400> SEQUENCE: 34

Val Val Gly Ala Asp Gly Val Gly Lys
1               5

```
<210> SEQ ID NO 35
<211> LENGTH: 9
<212> TYPE: PRT
<213> ORGANISM: Homo sapiens

<400> SEQUENCE: 35

Val Val Gly Ala Val Gly Val Gly Lys
1               5

<210> SEQ ID NO 36
<211> LENGTH: 9
<212> TYPE: PRT
<213> ORGANISM: Homo sapiens

<400> SEQUENCE: 36

Val Val Gly Ala Cys Gly Val Gly Lys
1               5

<210> SEQ ID NO 37
<211> LENGTH: 10
<212> TYPE: PRT
<213> ORGANISM: Homo sapiens

<400> SEQUENCE: 37

Val Val Val Gly Ala Cys Gly Val Gly Lys
1               5                   10

<210> SEQ ID NO 38
<211> LENGTH: 9
<212> TYPE: PRT
<213> ORGANISM: Homo sapiens

<400> SEQUENCE: 38

Val Val Gly Ala Arg Gly Val Gly Lys
1               5

<210> SEQ ID NO 39
<211> LENGTH: 10
<212> TYPE: PRT
<213> ORGANISM: Homo sapiens

<400> SEQUENCE: 39

Val Val Val Gly Ala Arg Gly Val Gly Lys
1               5                   10

<210> SEQ ID NO 40
<211> LENGTH: 16
<212> TYPE: PRT
<213> ORGANISM: Mus musculus

<400> SEQUENCE: 40

Cys Ala Met Arg Glu Asp Thr Gly Ala Asn Thr Gly Lys Leu Thr Phe
1               5                   10                  15

<210> SEQ ID NO 41
<211> LENGTH: 15
<212> TYPE: PRT
<213> ORGANISM: Mus musculus

<400> SEQUENCE: 41

Cys Ala Ser Ser Gln Asp Ser Leu Gly Arg Ala Glu Gln Phe Phe
1               5                   10                  15

<210> SEQ ID NO 42
<211> LENGTH: 15
```

```
<212> TYPE: PRT
<213> ORGANISM: Mus musculus

<400> SEQUENCE: 42

Cys Ala Ser Ser Ser Asp Trp Gly Gly Ala Glu Thr Leu Tyr Phe
1               5                   10                  15

<210> SEQ ID NO 43
<211> LENGTH: 16
<212> TYPE: PRT
<213> ORGANISM: Mus musculus

<400> SEQUENCE: 43

Cys Ala Ser Ser Ser Gly Leu Gly Ser Ser Ala Glu Thr Leu Tyr Phe
1               5                   10                  15

<210> SEQ ID NO 44
<211> LENGTH: 81
<212> TYPE: DNA
<213> ORGANISM: Artificial Sequence
<220> FEATURE:
<223> OTHER INFORMATION: Synthetic

<400> SEQUENCE: 44
cgggccaagc ggtccggatc cggagccacc aacttcagcc tgctgaagca ggccggcgac    60
gtggaggaga accccggccc c                                              81

<210> SEQ ID NO 45
<211> LENGTH: 604
<212> TYPE: PRT
<213> ORGANISM: Artificial Sequence
<220> FEATURE:
<223> OTHER INFORMATION: Synthetic

<400> SEQUENCE: 45

Met Arg Pro Val Thr Cys Ser Val Leu Val Leu Leu Met Leu Arg
1               5                   10                  15

Arg Ser Asn Gly Asp Gly Asp Ser Val Thr Gln Thr Glu Gly Leu Val
                20                  25                  30

Thr Leu Thr Glu Gly Leu Pro Val Met Leu Asn Cys Thr Tyr Gln Thr
            35                  40                  45

Ile Tyr Ser Asn Pro Phe Leu Phe Trp Tyr Val Gln His Leu Asn Glu
        50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
                100                 105                 110

Ala Leu Arg Gly Asn Ala Gly Ala Lys Leu Thr Phe Gly Gly Gly Thr
            115                 120                 125

Arg Leu Thr Val Arg Pro Asp Ile Gln Asn Pro Glu Pro Ala Val Tyr
        130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190
```

```
Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
        210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser Arg
                260                 265                 270

Ala Lys Arg Ser Gly Ser Gly Ala Thr Asn Phe Ser Leu Leu Lys Gln
        275                 280                 285

Ala Gly Asp Val Glu Glu Asn Pro Gly Pro Met Gly Cys Arg Leu Leu
        290                 295                 300

Ser Cys Val Ala Phe Cys Leu Leu Gly Ile Gly Pro Leu Glu Thr Ala
305                 310                 315                 320

Val Phe Gln Thr Pro Asn Tyr His Val Thr Gln Val Gly Asn Glu Val
                325                 330                 335

Ser Phe Asn Cys Lys Gln Thr Leu Gly His Asp Thr Met Tyr Trp Tyr
                340                 345                 350

Lys Gln Asp Ser Lys Lys Leu Leu Lys Ile Met Phe Ser Tyr Asn Asn
        355                 360                 365

Lys Gln Leu Ile Val Asn Glu Thr Val Pro Arg Arg Phe Ser Pro Gln
        370                 375                 380

Ser Ser Asp Lys Ala His Leu Asn Leu Arg Ile Lys Ser Val Glu Pro
385                 390                 395                 400

Glu Asp Ser Ala Val Tyr Leu Cys Ala Ser Ser Arg Asp Trp Ser
                405                 410                 415

Ala Glu Thr Leu Tyr Phe Gly Ser Gly Thr Arg Leu Thr Val Leu Glu
                420                 425                 430

Asp Leu Arg Asn Val Thr Pro Pro Lys Val Ser Leu Phe Glu Pro Ser
        435                 440                 445

Lys Ala Glu Ile Ala Asn Lys Gln Lys Ala Thr Leu Val Cys Leu Ala
450                 455                 460

Arg Gly Phe Phe Pro Asp His Val Glu Leu Ser Trp Trp Val Asn Gly
465                 470                 475                 480

Lys Glu Val His Ser Gly Val Ser Thr Asp Pro Gln Ala Tyr Lys Glu
                485                 490                 495

Ser Asn Tyr Ser Tyr Cys Leu Ser Ser Arg Leu Arg Val Ser Ala Thr
                500                 505                 510

Phe Trp His Asn Pro Arg Asn His Phe Arg Cys Gln Val Gln Phe His
        515                 520                 525

Gly Leu Ser Glu Glu Asp Lys Trp Pro Glu Gly Ser Pro Lys Pro Val
        530                 535                 540

Thr Gln Asn Ile Ser Ala Glu Ala Trp Gly Arg Ala Asp Cys Gly Ile
545                 550                 555                 560

Thr Ser Ala Ser Tyr His Gln Gly Val Leu Ser Ala Thr Ile Leu Tyr
                565                 570                 575

Glu Ile Leu Leu Gly Lys Ala Thr Leu Tyr Ala Val Leu Val Ser Gly
        580                 585                 590

Leu Val Leu Met Ala Met Val Lys Lys Asn Ser
        595                 600
```

-continued

```
<210> SEQ ID NO 46
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 46

Cys Xaa Leu Arg Gly Asn Ala Gly Ala Lys Leu Thr Phe
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 47

Cys Ala Xaa Arg Gly Asn Ala Gly Ala Lys Leu Thr Phe
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Ala, Asn, Asp, Cys, Glu, Gln, Gly, His,
      Ile, Leu, Lys, Met, Phe, Pro, Ser, Thr, Trp, Tyr, or Val.

<400> SEQUENCE: 48

Cys Ala Leu Xaa Gly Asn Ala Gly Ala Lys Leu Thr Phe
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 49

Cys Ala Leu Arg Xaa Asn Ala Gly Ala Lys Leu Thr Phe
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic
<220> FEATURE:
```

<221> NAME/KEY: MISC_FEATURE
<222> LOCATION: (6)..(6)
<223> OTHER INFORMATION: Xaa is Ala, Arg, Asp, Cys, Glu, Gln, Gly, His,
      Ile, Leu, Lys, Met, Phe, Pro, Ser, Thr, Trp, Tyr, or Val.

<400> SEQUENCE: 50

Cys Ala Leu Arg Gly Xaa Ala Gly Ala Lys Leu Thr Phe
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 51

Cys Ala Leu Arg Gly Asn Xaa Gly Ala Lys Leu Thr Phe
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 52

Cys Ala Leu Arg Gly Asn Ala Xaa Ala Lys Leu Thr Phe
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 53

Cys Ala Leu Arg Gly Asn Ala Gly Xaa Lys Leu Thr Phe
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is Ala, Arg, Asn, Asp, Cys, Glu, Gln, Gly,
      His, Ile, Leu, Met, Phe, Pro, Ser, Thr, Trp, Tyr, or Val.

<400> SEQUENCE: 54

```
Cys Ala Leu Arg Gly Asn Ala Gly Ala Xaa Leu Thr Phe
1               5                   10
```

<210> SEQ ID NO 55
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 55

```
Cys Ala Leu Arg Gly Asn Ala Gly Ala Lys Xaa Thr Phe
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa is Ala, Arg, Asn, Asp, Cys, Glu, Gln, Gly,
      His, Ile, Leu, Lys, Met, Phe, Pro, Ser, Trp, Tyr, or Val.

<400> SEQUENCE: 56

```
Cys Ala Leu Arg Gly Asn Ala Gly Ala Lys Leu Xaa Phe
1               5                   10
```

<210> SEQ ID NO 57
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 57

```
Cys Xaa Ser Ser Ser Arg Asp Trp Ser Ala Glu Thr Leu Tyr Phe
1               5                   10                  15
```

<210> SEQ ID NO 58
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 58

```
Cys Ala Xaa Ser Ser Arg Asp Trp Ser Ala Glu Thr Leu Tyr Phe
1               5                   10                  15
```

<210> SEQ ID NO 59
<211> LENGTH: 15
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 59

Cys Ala Ser Xaa Ser Arg Asp Trp Ser Ala Glu Thr Leu Tyr Phe
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 60

Cys Ala Ser Ser Xaa Arg Asp Trp Ser Ala Glu Thr Leu Tyr Phe
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Ala, Asn, Asp, Cys, Glu, Gln, Gly, His,
      Ile, Leu, Lys, Met, Phe, Pro, Ser, Thr, Trp, Tyr, or Val,

<400> SEQUENCE: 61

Cys Ala Ser Ser Ser Xaa Asp Trp Ser Ala Glu Thr Leu Tyr Phe
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is Ala, Arg, Asn, Cys, Glu, Gln, Gly, His,
      Ile, Leu, Lys, Met, Phe, Pro, Ser, Thr, Trp, Tyr, or Val.

<400> SEQUENCE: 62

Cys Ala Ser Ser Ser Arg Xaa Trp Ser Ala Glu Thr Leu Tyr Phe
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is Ala, Arg, Asn, Asp, Cys, Glu, Gln, Gly,
```

His, Ile, Leu, Lys, Met, Phe, Pro, Ser, Thr, Tyr, or Val.

<400> SEQUENCE: 63

Cys Ala Ser Ser Ser Arg Asp Xaa Ser Ala Glu Thr Leu Tyr Phe
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 64

Cys Ala Ser Ser Ser Arg Asp Trp Xaa Ala Glu Thr Leu Tyr Phe
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 65

Cys Ala Ser Ser Ser Arg Asp Trp Ser Xaa Glu Thr Leu Tyr Phe
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Xaa is Ala, Arg, Asn, Asp, Cys, Gln, Gly, His,
      Ile, Leu, Lys, Met, Phe, Pro, Ser, Thr, Trp, Tyr, or Val.

<400> SEQUENCE: 66

Cys Ala Ser Ser Ser Arg Asp Trp Ser Ala Xaa Thr Leu Tyr Phe
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa is Ala, Arg, Asn, Asp, Cys, Glu, Gln, Gly,
      His, Ile, Leu, Lys, Met, Phe, Pro, Ser, Trp, Tyr, or Val.

<400> SEQUENCE: 67

Cys Ala Ser Ser Ser Arg Asp Trp Ser Ala Glu Xaa Leu Tyr Phe
1               5                   10                  15

```
<210> SEQ ID NO 68
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 68

Cys Ala Ser Ser Ser Arg Asp Trp Ser Ala Glu Thr Xaa Tyr Phe
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, or Val.

<400> SEQUENCE: 69

Cys Ala Ser Ser Ser Arg Asp Trp Ser Ala Glu Thr Leu Xaa Phe
1               5                   10                  15

<210> SEQ ID NO 70
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (113)..(113)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 70

Met Arg Pro Val Thr Cys Ser Val Leu Val Leu Leu Met Leu Arg
1               5                   10                  15

Arg Ser Asn Gly Asp Gly Asp Ser Val Thr Gln Thr Glu Gly Leu Val
                20                  25                  30

Thr Leu Thr Glu Gly Leu Pro Val Met Leu Asn Cys Thr Tyr Gln Thr
            35                  40                  45

Ile Tyr Ser Asn Pro Phe Leu Phe Trp Tyr Val Gln His Leu Asn Glu
        50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
                100                 105                 110

Xaa Leu Arg Gly Asn Ala Gly Ala Lys Leu Thr Phe Gly Gly Gly Thr
            115                 120                 125

Arg Leu Thr Val Arg Pro Asp
        130                 135
```

```
<210> SEQ ID NO 71
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (114)..(114)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or val.

<400> SEQUENCE: 71

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Xaa Arg Gly Asn Ala Gly Ala Lys Leu Thr Phe Gly Gly Gly Thr
        115                 120                 125

Arg Leu Thr Val Arg Pro Asp
        130                 135

<210> SEQ ID NO 72
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (115)..(115)
<223> OTHER INFORMATION: Xaa is Ala, Asn, Asp, Cys, Glu, Gln, Gly, His,
      Ile, Leu, Lys, Met, Phe, Pro, Ser, Thr, Trp, Tyr, or Val.

<400> SEQUENCE: 72

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Xaa Gly Asn Ala Gly Ala Lys Leu Thr Phe Gly Gly Gly Thr
        115                 120                 125
```

Arg Leu Thr Val Arg Pro Asp
    130             135

<210> SEQ ID NO 73
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(116)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 73

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Xaa Asn Ala Gly Ala Lys Leu Thr Phe Gly Gly Gly Thr
        115                 120                 125

Arg Leu Thr Val Arg Pro Asp
    130             135

<210> SEQ ID NO 74
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (117)..(117)
<223> OTHER INFORMATION: Xaa is Ala, Arg, Asp, Cys, Glu, Gln, Gly, His,
      Ile, Leu, Lys, Met, Phe, Pro, Ser, Thr, Trp, Tyr, or Val.

<400> SEQUENCE: 74

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

```
Leu Gln Lys Ser Ser Ala Gln Leu Ser Asp Ser Ala Leu Tyr Tyr Cys
                100                 105                 110

Ala Leu Arg Gly Xaa Ala Gly Ala Lys Leu Thr Phe Gly Gly Gly Thr
            115                 120                 125

Arg Leu Thr Val Arg Pro Asp
        130                 135

<210> SEQ ID NO 75
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (118)..(118)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 75

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
                100                 105                 110

Ala Leu Arg Gly Asn Xaa Gly Ala Lys Leu Thr Phe Gly Gly Gly Thr
            115                 120                 125

Arg Leu Thr Val Arg Pro Asp
        130                 135

<210> SEQ ID NO 76
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 76

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
```

```
                 65                  70                  75                  80
His Gln Gly Phe His Ala Thr Leu His Lys Ser Ser Ser Phe His
                 85                  90                  95

Leu Gln Lys Ser Ser Ala Gln Leu Ser Asp Ser Ala Leu Tyr Tyr Cys
                100                 105                 110

Ala Leu Arg Gly Asn Ala Xaa Ala Lys Leu Thr Phe Gly Gly Gly Thr
                115                 120                 125

Arg Leu Thr Val Arg Pro Asp
                130                 135

<210> SEQ ID NO 77
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (120)..(120)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 77

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
                20                  25                  30

Thr Leu Thr Glu Gly Leu Pro Val Met Leu Asn Cys Thr Tyr Gln Thr
                35                  40                  45

Ile Tyr Ser Asn Pro Phe Leu Phe Trp Tyr Val Gln His Leu Asn Glu
            50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
                100                 105                 110

Ala Leu Arg Gly Asn Ala Gly Xaa Lys Leu Thr Phe Gly Gly Gly Thr
                115                 120                 125

Arg Leu Thr Val Arg Pro Asp
                130                 135

<210> SEQ ID NO 78
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (121)..(121)
<223> OTHER INFORMATION: Xaa is Ala, Arg, Asn, Asp, Cys, Glu, Gln, Gly,
      His, Ile, Leu, Met, Phe, Pro, Ser, Thr, Trp, Tyr, or val.

<400> SEQUENCE: 78

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
                20                  25                  30

Thr Leu Thr Glu Gly Leu Pro Val Met Leu Asn Cys Thr Tyr Gln Thr
                35                  40                  45
```

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
             85                  90                  95

Leu Gln Lys Ser Ser Ala Gln Leu Ser Asp Ser Ala Leu Tyr Tyr Cys
             100                 105                 110

Ala Leu Arg Gly Asn Ala Gly Ala Xaa Leu Thr Phe Gly Gly Gly Thr
         115                 120                 125

Arg Leu Thr Val Arg Pro Asp
        130                 135

<210> SEQ ID NO 79
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (122)..(122)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 79

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
             85                  90                  95

Leu Gln Lys Ser Ser Ala Gln Leu Ser Asp Ser Ala Leu Tyr Tyr Cys
             100                 105                 110

Ala Leu Arg Gly Asn Ala Gly Ala Lys Xaa Thr Phe Gly Gly Gly Thr
         115                 120                 125

Arg Leu Thr Val Arg Pro Asp
        130                 135

<210> SEQ ID NO 80
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (123)..(123)
<223> OTHER INFORMATION: Xaa is Ala, Arg, Asn, Asp, Cys, Glu, Gln, Gly,
      His, Ile, Leu, Lys, Met, Phe, Pro, Ser, Trp, Tyr, or Val.

<400> SEQUENCE: 80

Met Arg Pro Val Thr Cys Ser Val Leu Val Leu Leu Leu Met Leu Arg
1               5                   10                  15

-continued

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Ala Gly Ala Lys Leu Xaa Phe Gly Gly Gly Thr
            115                 120                 125

Arg Leu Thr Val Arg Pro Asp
            130             135

<210> SEQ ID NO 81
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(111)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 81

Met Gly Cys Arg Leu Leu Ser Cys Val Ala Phe Cys Leu Leu Gly Ile
 1               5                  10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
 50                  55                  60

Met Phe Ser Tyr Asn Asn Lys Gln Leu Ile Val Asn Glu Thr Val Pro
 65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Xaa Ser
            100                 105                 110

Ser Ser Arg Asp Trp Ser Ala Glu Thr Leu Tyr Phe Gly Ser Gly Thr
            115                 120                 125

Arg Leu Thr Val Leu Glu
            130

<210> SEQ ID NO 82
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (112)..(112)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 82

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Xaa
            100                 105                 110

Ser Ser Arg Asp Trp Ser Ala Glu Thr Leu Tyr Phe Gly Ser Gly Thr
            115                 120                 125

Arg Leu Thr Val Leu Glu
    130

<210> SEQ ID NO 83
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (113)..(113)
<223> OTHER INFORMATION: X is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 83

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Xaa Ser Arg Asp Trp Ser Ala Glu Thr Leu Tyr Phe Gly Ser Gly Thr
            115                 120                 125

Arg Leu Thr Val Leu Glu
    130

<210> SEQ ID NO 84
<211> LENGTH: 134
<212> TYPE: PRT
<213> ORGANISM: Artificial Sequence
<220> FEATURE:
<223> OTHER INFORMATION: Synthetic
<220> FEATURE:

<220> FEATURE:
<221> NAME/KEY: MISC_FEATURE
<222> LOCATION: (114)..(114)
<223> OTHER INFORMATION: Xaa is Ala, Arg, Asn, Asp, Cys, Glu, Gln, Gly, His, Ile, Leu, Lys, Met, Phe, Pro, Thr, Trp, Tyr, or Val.

<400> SEQUENCE: 84

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Xaa Arg Asp Trp Ser Ala Glu Thr Leu Tyr Phe Gly Ser Gly Thr
        115                 120                 125

Arg Leu Thr Val Leu Glu
            130

<210> SEQ ID NO 85
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (115)..(115)
<223> OTHER INFORMATION: Xaa is Ala, Asn, Asp, Cys, Glu, Gln, Gly, His, Ile, Leu, Lys, Met, Phe, Pro, Ser, Thr, Trp, Tyr, or Val.

<400> SEQUENCE: 85

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Xaa Asp Trp Ser Ala Glu Thr Leu Tyr Phe Gly Ser Gly Thr
        115                 120                 125

Arg Leu Thr Val Leu Glu
            130

<210> SEQ ID NO 86
<211> LENGTH: 134

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(116)
<223> OTHER INFORMATION: Xaa is Ala, Arg, Asn, Cys, Glu, Gln, Gly, His,
      Ile, Leu, Lys, Met, Phe, Pro, Ser, Thr, Trp, Tyr, or Val.

<400> SEQUENCE: 86

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Xaa Trp Ser Ala Glu Thr Leu Tyr Phe Gly Ser Gly Thr
        115                 120                 125

Arg Leu Thr Val Leu Glu
    130

<210> SEQ ID NO 87
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (117)..(117)
<223> OTHER INFORMATION: Xaa is Ala, Arg, Asn, Asp, Cys, Glu, Gln, Gly,
      His, Ile, Leu, Lys, Met, Phe, Pro, Ser, Thr, Tyr, or Val.

<400> SEQUENCE: 87

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Xaa Ser Ala Glu Thr Leu Tyr Phe Gly Ser Gly Thr
        115                 120                 125

Arg Leu Thr Val Leu Glu
```

-continued

```
        130

<210> SEQ ID NO 88
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (118)..(118)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 88

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Xaa Ala Glu Thr Leu Tyr Phe Gly Ser Gly Thr
        115                 120                 125

Arg Leu Thr Val Leu Glu
    130

<210> SEQ ID NO 89
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 89

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110
```

```
Ser Ser Arg Asp Trp Ser Xaa Glu Thr Leu Tyr Phe Gly Ser Gly Thr
        115                 120                 125

Arg Leu Thr Val Leu Glu
    130

<210> SEQ ID NO 90
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (120)..(120)
<223> OTHER INFORMATION: Xaa is Ala, Arg, Asn, Asp, Cys, Gln, Gly, His,
      Ile, Leu, Lys, Met, Phe, Pro, Ser, Thr, Trp, Tyr, or Val.

<400> SEQUENCE: 90

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Ala Xaa Thr Leu Tyr Phe Gly Ser Gly Thr
        115                 120                 125

Arg Leu Thr Val Leu Glu
    130

<210> SEQ ID NO 91
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (121)..(121)
<223> OTHER INFORMATION: Xaa is Ala, Arg, Asn, Asp, Cys, Glu, Gln, Gly,
      His, Ile, Leu, Lys, Met, Phe, Pro, Ser, Trp, Tyr, or Val.

<400> SEQUENCE: 91

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80
```

Arg Arg Phe Ser Pro Gln Ser Ser Asp Lys Ala His Leu Asn Leu Arg
            85                  90                  95

Ile Lys Ser Val Glu Pro Glu Asp Ser Ala Val Tyr Leu Cys Ala Ser
            100                 105                 110

Ser Ser Arg Asp Trp Ser Ala Glu Xaa Leu Tyr Phe Gly Ser Gly Thr
            115                 120                 125

Arg Leu Thr Val Leu Glu
            130

<210> SEQ ID NO 92
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (122)..(122)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 92

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
            35                  40                  45

Asp Thr Met Tyr Trp Tyr Lys Gln Asp Ser Lys Lys Leu Leu Lys Ile
50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
            85                  90                  95

Ile Lys Ser Val Glu Pro Glu Asp Ser Ala Val Tyr Leu Cys Ala Ser
            100                 105                 110

Ser Ser Arg Asp Trp Ser Ala Glu Thr Xaa Tyr Phe Gly Ser Gly Thr
            115                 120                 125

Arg Leu Thr Val Leu Glu
            130

<210> SEQ ID NO 93
<211> LENGTH: 134
<212> TYPE: PRT
<213> ORGANISM: Artificial Sequence
<220> FEATURE:
<223> OTHER INFORMATION: 'Synthetic
<220> FEATURE:
<221> NAME/KEY: MISC_FEATURE
<222> LOCATION: (123)..(123)
<223> OTHER INFORMATION: Xaa is Ala, Arg, Asn, Asp, Cys, Glu, Gln, Gly,
      His, Ile, Leu, Lys, Met, Phe, Pro, Ser, Thr, Trp, or Val.

<400> SEQUENCE: 93

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
            35                  40                  45

Asp Thr Met Tyr Trp Tyr Lys Gln Asp Ser Lys Lys Leu Leu Lys Ile

```
            50                  55                  60
Met Phe Ser Tyr Asn Asn Lys Gln Leu Ile Val Asn Glu Thr Val Pro
 65                  70                  75                  80

Arg Arg Phe Ser Pro Gln Ser Ser Asp Lys Ala His Leu Asn Leu Arg
                 85                  90                  95

Ile Lys Ser Val Glu Pro Glu Asp Ser Ala Val Tyr Leu Cys Ala Ser
               100                 105                 110

Ser Ser Arg Asp Trp Ser Ala Glu Thr Leu Xaa Phe Gly Ser Gly Thr
           115                 120                 125

Arg Leu Thr Val Leu Glu
       130

<210> SEQ ID NO 94
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (113)..(113)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 94

Met Arg Pro Val Thr Cys Ser Val Leu Val Leu Leu Leu Met Leu Arg
  1               5                  10                  15

Arg Ser Asn Gly Asp Gly Asp Ser Val Thr Gln Thr Glu Gly Leu Val
                 20                  25                  30

Thr Leu Thr Glu Gly Leu Pro Val Met Leu Asn Cys Thr Tyr Gln Thr
             35                  40                  45

Ile Tyr Ser Asn Pro Phe Leu Phe Trp Tyr Val Gln His Leu Asn Glu
         50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Ser Phe His
                 85                  90                  95

Leu Gln Lys Ser Ser Ala Gln Leu Ser Asp Ser Ala Leu Tyr Tyr Cys
               100                 105                 110

Xaa Leu Arg Gly Asn Ala Gly Ala Lys Leu Thr Phe Gly Gly Gly Thr
           115                 120                 125

Arg Leu Thr Val Arg Pro Asp Ile Gln Asn Pro Glu Pro Ala Val Tyr
       130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255
```

```
Val Ala Gly Phe Asn Leu Leu Met Thr Leu Arg Leu Trp Ser Ser
            260                 265                 270

<210> SEQ ID NO 95
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (114)..(114)
<223> OTHER INFORMATION: Xaa is Ala, Arg, Asn, Asp, Cys, Glu, Gln, Gly,
      His, Ile, Lys, Met, Phe, Pro, Ser, Thr, Trp, Tyr, or Val.

<400> SEQUENCE: 95

Met Arg Pro Val Thr Cys Ser Val Leu Val Leu Leu Met Leu Arg
1               5                  10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
            35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
            85                  90                  95

Leu Gln Lys Ser Ser Ala Gln Leu Ser Asp Ser Ala Leu Tyr Tyr Cys
            100                 105                 110

Ala Xaa Arg Gly Asn Ala Gly Ala Lys Leu Thr Phe Gly Gly Gly Thr
            115                 120                 125

Arg Leu Thr Val Arg Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 96
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (115)..(115)
<223> OTHER INFORMATION: Xaa is Ala, Asn, Asp, Cys, Glu, Gln, Gly, His,
      Ile, Leu, Lys, Met, Phe, Pro, Ser, Thr, Trp, Tyr, or Val.

<400> SEQUENCE: 96

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Xaa Gly Asn Ala Gly Ala Lys Leu Thr Phe Gly Gly Gly Thr
        115                 120                 125

Arg Leu Thr Val Arg Pro Asp Ile Gln Asn Pro Glu Pro Ala Val Tyr
130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 97
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(116)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 97

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
```

```
            35                  40                  45
Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Ser Phe His
                 85                  90                  95

Leu Gln Lys Ser Ser Ala Gln Leu Ser Asp Ser Ala Leu Tyr Tyr Cys
                100                 105                 110

Ala Leu Arg Xaa Asn Ala Gly Ala Lys Leu Thr Phe Gly Gly Gly Thr
                115                 120                 125

Arg Leu Thr Val Arg Pro Asp Ile Gln Asn Pro Glu Pro Ala Val Tyr
            130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
                180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 98
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (117)..(117)
<223> OTHER INFORMATION: Xaa is Ala, Arg, Asp, Cys, Glu, Gln, Gly, His,
      Ile, Leu, Lys, Met, Phe, Pro, Ser, Thr, Trp, Tyr, or Val.

<400> SEQUENCE: 98

Met Arg Pro Val Thr Cys Ser Val Leu Val Leu Leu Met Leu Arg
 1               5                  10                  15

Arg Ser Asn Gly Asp Gly Asp Ser Val Thr Gln Thr Glu Gly Leu Val
                 20                  25                  30

Thr Leu Thr Glu Gly Leu Pro Val Met Leu Asn Cys Thr Tyr Gln Thr
             35                  40                  45

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Ser Phe His
                 85                  90                  95

Leu Gln Lys Ser Ser Ala Gln Leu Ser Asp Ser Ala Leu Tyr Tyr Cys
                100                 105                 110
```

```
Ala Leu Arg Gly Xaa Ala Gly Ala Lys Leu Thr Phe Gly Gly Gly Thr
            115                 120                 125

Arg Leu Thr Val Arg Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270
```

<210> SEQ ID NO 99
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (118)..(118)
<223> OTHER INFORMATION: Xaa is Arg, Asn, Asp, Cys, Glu, Gln, Gly, His, Ile, Leu, Lys, Met, Phe, Pro, Ser, Thr, Trp, Tyr, or Val.

<400> SEQUENCE: 99

```
Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Xaa Gly Ala Lys Leu Thr Phe Gly Gly Gly Thr
        115                 120                 125

Arg Leu Thr Val Arg Pro Asp Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175
```

```
Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
        210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
            245                 250                 255

Val Ala Gly Phe Asn Leu Leu Met Thr Leu Arg Leu Trp Ser Ser
            260                 265                 270

<210> SEQ ID NO 100
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: Xaa is Ala, Arg, Asn, Asp, Cys, Glu, Gln, His,
      Ile, Leu, Lys, Met, Phe, Pro, Ser, Thr, Trp, Tyr, or Val.

<400> SEQUENCE: 100

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Ala Xaa Ala Lys Leu Thr Phe Gly Gly Gly Thr
        115                 120                 125

Arg Leu Thr Val Arg Pro Asp Ile Gln Asn Pro Glu Pro Ala Val Tyr
130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
        210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
```

```
                        245                 250                 255
Val Ala Gly Phe Asn Leu Leu Met Thr Leu Arg Leu Trp Ser Ser
            260                 265                 270

<210> SEQ ID NO 101
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (120)..(120)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 101

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
                85                  90                  95

Leu Gln Lys Ser Ser Ala Gln Leu Ser Asp Ser Ala Leu Tyr Tyr Cys
                100                 105                 110

Ala Leu Arg Gly Asn Ala Gly Xaa Lys Leu Thr Phe Gly Gly Gly Thr
            115                 120                 125

Arg Leu Thr Val Arg Pro Asp Ile Gln Asn Pro Glu Pro Ala Val Tyr
        130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 102
<211> LENGTH: 271
<212> TYPE: PRT
<213> ORGANISM: Artificial Sequence
<220> FEATURE:
<223> OTHER INFORMATION: Synthetic
<220> FEATURE:
```

<220> FEATURE:
<221> NAME/KEY: MISC_FEATURE
<222> LOCATION: (121)..(121)
<223> OTHER INFORMATION: Xaa is Ala, Arg, Asn, Asp, Cys, Glu, Gln, Gly, His, Ile, Leu, Met, Phe, Pro, Ser, Thr, Trp, Tyr, or Val.

<400> SEQUENCE: 102

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Ser Phe His
                85                  90                  95

Leu Gln Lys Ser Ser Ala Gln Leu Ser Asp Ser Ala Leu Tyr Tyr Cys
            100                 105                 110

Ala Leu Arg Gly Asn Ala Gly Ala Xaa Leu Thr Phe Gly Gly Gly Thr
        115                 120                 125

Arg Leu Thr Val Arg Pro Asp Ile Gln Asn Pro Glu Pro Ala Val Tyr
130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 103
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (122)..(122)
<223> OTHER INFORMATION: Xaa is Ala, Arg, Asn, Asp, Cys, Glu, Gln, Gly, His, Ile, Lys, Met, Phe, Pro, Ser, Thr, Trp, Tyr, or Val.

<400> SEQUENCE: 103

Met Arg Pro Val Thr Cys Ser Val Leu Val Leu Leu Leu Met Leu Arg
1               5                   10                  15

Arg Ser Asn Gly Asp Gly Asp Ser Val Thr Gln Thr Glu Gly Leu Val
            20                  25                  30

```
Thr Leu Thr Glu Gly Leu Pro Val Met Leu Asn Cys Thr Tyr Gln Thr
         35                  40                  45

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Phe His
             85                  90                  95

Leu Gln Lys Ser Ser Ala Gln Leu Ser Asp Ser Ala Leu Tyr Tyr Cys
             100                 105                 110

Ala Leu Arg Gly Asn Ala Gly Ala Lys Xaa Thr Phe Gly Gly Gly Thr
             115                 120                 125

Arg Leu Thr Val Arg Pro Asp Ile Gln Asn Pro Glu Pro Ala Val Tyr
 130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
             165                 170                 175

Phe Ile Thr Asp Lys Thr Val Leu Asp Met Lys Ala Met Asp Ser Lys
             180                 185                 190

Ser Asn Gly Ala Ile Ala Trp Ser Asn Gln Thr Ser Phe Thr Cys Gln
             195                 200                 205

Asp Ile Phe Lys Glu Thr Asn Ala Thr Tyr Pro Ser Ser Asp Val Pro
             210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
             245                 250                 255

Val Ala Gly Phe Asn Leu Leu Met Thr Leu Arg Leu Trp Ser Ser
             260                 265                 270

<210> SEQ ID NO 104
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (123)..(123)
<223> OTHER INFORMATION: Xaa is Ala, Arg, Asn, Asp, Cys, Glu, Gln, Gly,
      His, Ile, Leu, Lys, Met, Phe, Pro, Ser, Trp, Tyr, or Val.

<400> SEQUENCE: 104

Met Arg Pro Val Thr Cys Ser Val Leu Val Leu Leu Met Leu Arg
 1                   5                  10                  15

Arg Ser Asn Gly Asp Gly Asp Ser Val Thr Gln Thr Glu Gly Leu Val
             20                  25                  30

Thr Leu Thr Glu Gly Leu Pro Val Met Leu Asn Cys Thr Tyr Gln Thr
         35                  40                  45

Ile Tyr Ser Asn Pro Phe Leu Phe Trp Tyr Val Gln His Leu Asn Glu
 50                  55                  60

Ser Pro Arg Leu Leu Leu Lys Ser Phe Thr Asp Asn Lys Arg Thr Glu
 65                  70                  75                  80

His Gln Gly Phe His Ala Thr Leu His Lys Ser Ser Ser Phe His
             85                  90                  95

Leu Gln Lys Ser Ser Ala Gln Leu Ser Asp Ser Ala Leu Tyr Tyr Cys
```

```
                    100                 105                 110
Ala Leu Arg Gly Asn Ala Gly Ala Lys Leu Xaa Phe Gly Gly Gly Thr
            115                 120                 125

Arg Leu Thr Val Arg Pro Asp Ile Gln Asn Pro Glu Pro Ala Val Tyr
        130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 105
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(111)
<223> OTHER INFORMATION: Xaa is Arg, Asn, Asp, Cys, Glu, Gln, Gly, His,
      Ile, Leu, Lys, Met, Phe, Pro, Ser, Thr, Trp, Tyr, or Val.

<400> SEQUENCE: 105

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Xaa Ser
            100                 105                 110

Ser Ser Arg Asp Trp Ser Ala Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175
```

```
Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Gly Leu Val Leu Met Ala Met Val Lys Lys Lys
            290                 295                 300

Asn Ser
305

<210> SEQ ID NO 106
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (112)..(112)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 106

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
            35                  40                  45

Asp Thr Met Tyr Trp Tyr Lys Gln Asp Ser Lys Lys Leu Leu Lys Ile
        50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Xaa
            100                 105                 110

Ser Ser Arg Asp Trp Ser Ala Glu Thr Leu Tyr Phe Gly Ser Gly Thr
            115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190
```

```
Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305
```

<210> SEQ ID NO 107
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (113)..(113)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 107

```
Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Xaa Ser Arg Asp Trp Ser Ala Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220
```

```
            210                 215                 220
Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Gly Leu Val Leu Met Ala Met Val Lys Lys Lys
                290                 295                 300

Asn Ser
305

<210> SEQ ID NO 108
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (114)..(114)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 108

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
                20                  25                  30

Gln Val Gly Asn Glu Val Ser Phe Asn Cys Lys Gln Thr Leu Gly His
                35                  40                  45

Asp Thr Met Tyr Trp Tyr Lys Gln Asp Ser Lys Lys Leu Leu Lys Ile
            50                  55                  60

Met Phe Ser Tyr Asn Asn Lys Gln Leu Ile Val Asn Glu Thr Val Pro
65              70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
                100                 105                 110

Ser Xaa Arg Asp Trp Ser Ala Glu Thr Leu Tyr Phe Gly Ser Gly Thr
            115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
            210                 215                 220

Cys Gln Val Gln Phe His Gly Leu Ser Glu Glu Asp Lys Trp Pro Glu
225                 230                 235                 240
```

```
Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 109
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (115)..(115)
<223> OTHER INFORMATION: Xaa is Ala, Asn, Asp, Cys, Glu, Gln, Gly, His,
      Ile, Leu, Lys, Met, Phe, Pro, Ser, Thr, Trp, Tyr, or Val.

<400> SEQUENCE: 109

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Xaa Asp Trp Ser Ala Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255
```

```
Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
290                 295                 300

Asn Ser
305

<210> SEQ ID NO 110
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(116)
<223> OTHER INFORMATION: Xaa is Ala, Arg, Asn, Cys, Glu, Gln, Gly, His,
      Ile, Leu, Lys, Met, Phe, Pro, Ser, Thr, Trp, Tyr, or Val.

<400> SEQUENCE: 110

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Xaa Trp Ser Ala Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285
```

```
                    275                 280                 285
Ala Val Leu Val Ser Gly Leu Val Leu Met Ala Met Val Lys Lys Lys
            290                 295                 300

Asn Ser
305

<210> SEQ ID NO 111
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (117)..(117)
<223> OTHER INFORMATION: Xaa is Ala, Arg, Asn, Asp, Cys, Glu, Gln, Gly,
      His, Ile, Leu, Lys, Met, Phe, Pro, Ser, Thr, Tyr, or Val.

<400> SEQUENCE: 111

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Xaa Ser Ala Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300
```

Asn Ser
305

<210> SEQ ID NO 112
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (118)..(118)
<223> OTHER INFORMATION: Xaa is Ala, Arg, Asn, Asp, Cys, Glu, Gln, Gly,
      His, Ile, Leu, Lys, Met, Phe, Pro, Thr, Trp, Tyr, or Val.

<400> SEQUENCE: 112

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Xaa Ala Glu Thr Leu Tyr Phe Gly Ser Gly Thr
        115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 113
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: Xaa is Arg, Asn, Asp, Cys, Glu, Gln, Gly, His, Ile, Leu, Lys, Met, Phe, Pro, Ser, Thr, Trp, Tyr, or Val.

<400> SEQUENCE: 113

```
Met Gly Cys Arg Leu Leu Ser Cys Val Ala Phe Cys Leu Leu Gly Ile
 1               5                  10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Xaa Glu Thr Leu Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305
```

<210> SEQ ID NO 114
<211> LENGTH: 306
<212> TYPE: PRT

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (120)..(120)
<223> OTHER INFORMATION: Xaa is Ala, Arg, Asn, Asp, Cys, Gln, Gly, His, Ile, Leu, Lys, Met, Phe, Pro, Ser, Thr, Trp, Tyr, or Val.

<400> SEQUENCE: 114

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Ala Xaa Thr Leu Tyr Phe Gly Ser Gly Thr
        115                 120                 125

Arg Leu Thr Val Leu Glu Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
290                 295                 300

Asn Ser
305

<210> SEQ ID NO 115
<211> LENGTH: 306
<212> TYPE: PRT
<213> ORGANISM: Artificial Sequence
<220> FEATURE:
<223> OTHER INFORMATION: Synthetic
<220> FEATURE:

<220> NAME/KEY: MISC_FEATURE
<222> LOCATION: (121)..(121)
<223> OTHER INFORMATION: Xaa is Ala, Arg, Asn, Asp, Cys, Glu, Gln, Gly, His, Ile, Leu, Lys, Met, Phe, Pro, Ser, Trp, Tyr, or Val.

<400> SEQUENCE: 115

```
Met Gly Cys Arg Leu Leu Ser Cys Val Ala Phe Cys Leu Leu Gly Ile
1               5                   10                  15
Gly Pro Leu Glu Thr Ala Val Phe Gln Thr Pro Asn Tyr His Val Thr
            20                  25                  30
Gln Val Gly Asn Glu Val Ser Phe Asn Cys Lys Gln Thr Leu Gly His
        35                  40                  45
Asp Thr Met Tyr Trp Tyr Lys Gln Asp Ser Lys Lys Leu Leu Lys Ile
50                  55                  60
Met Phe Ser Tyr Asn Asn Lys Gln Leu Ile Val Asn Glu Thr Val Pro
65                  70                  75                  80
Arg Arg Phe Ser Pro Gln Ser Ser Asp Lys Ala His Leu Asn Leu Arg
                85                  90                  95
Ile Lys Ser Val Glu Pro Glu Asp Ser Ala Val Tyr Leu Cys Ala Ser
            100                 105                 110
Ser Ser Arg Asp Trp Ser Ala Glu Xaa Leu Tyr Phe Gly Ser Gly Thr
        115                 120                 125
Arg Leu Thr Val Leu Glu Asp Leu Arg Asn Val Thr Pro Pro Lys Val
130                 135                 140
Ser Leu Phe Glu Pro Ser Lys Ala Glu Ile Ala Asn Lys Gln Lys Ala
145                 150                 155                 160
Thr Leu Val Cys Leu Ala Arg Gly Phe Phe Pro Asp His Val Glu Leu
                165                 170                 175
Ser Trp Trp Val Asn Gly Lys Glu Val His Ser Gly Val Ser Thr Asp
            180                 185                 190
Pro Gln Ala Tyr Lys Glu Ser Asn Tyr Ser Tyr Cys Leu Ser Ser Arg
        195                 200                 205
Leu Arg Val Ser Ala Thr Phe Trp His Asn Pro Arg Asn His Phe Arg
210                 215                 220
Cys Gln Val Gln Phe His Gly Leu Ser Glu Glu Asp Lys Trp Pro Glu
225                 230                 235                 240
Gly Ser Pro Lys Pro Val Thr Gln Asn Ile Ser Ala Glu Ala Trp Gly
                245                 250                 255
Arg Ala Asp Cys Gly Ile Thr Ser Ala Ser Tyr His Gln Gly Val Leu
            260                 265                 270
Ser Ala Thr Ile Leu Tyr Glu Ile Leu Leu Gly Lys Ala Thr Leu Tyr
        275                 280                 285
Ala Val Leu Val Ser Gly Leu Val Leu Met Ala Met Val Lys Lys Lys
290                 295                 300
Asn Ser
305
```

<210> SEQ ID NO 116
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (122)..(122)
<223> OTHER INFORMATION: Xaa is Ala, Arg, Asn, Asp, Cys, Glu, Gln, Gly, His, Ile, Lys, Met, Phe, Pro, Ser, Thr, Trp, Tyr, or Val.

<400> SEQUENCE: 116

```
Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Ser Arg Asp Trp Ser Ala Glu Thr Xaa Tyr Phe Gly Ser Gly Thr
        115                 120                 125

Arg Leu Thr Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305
```

<210> SEQ ID NO 117
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (123)..(123)
<223> OTHER INFORMATION: Xaa is Ala, Arg, Asn, Asp, Cys, Glu, Gln, Gly, His, Ile, Leu, Lys, Met, Phe, Pro, Ser, Thr, Trp, or Val.

<400> SEQUENCE: 117

Met Gly Cys Arg Leu Leu Ser Cys Val Ala Phe Cys Leu Leu Gly Ile

```
            1               5                  10                 15
        Gly Pro Leu Glu Thr Ala Val Phe Gln Thr Pro Asn Tyr His Val Thr
                        20                 25                 30

Gln Val Gly Asn Glu Val Ser Phe Asn Cys Lys Gln Thr Leu Gly His
                        35                 40                 45

Asp Thr Met Tyr Trp Tyr Lys Gln Asp Ser Lys Leu Leu Lys Ile
                 50                 55                 60

Met Phe Ser Tyr Asn Asn Lys Gln Leu Ile Val Asn Glu Thr Val Pro
         65                 70                 75                 80

Arg Arg Phe Ser Pro Gln Ser Ser Asp Lys Ala His Leu Asn Leu Arg
                        85                 90                 95

Ile Lys Ser Val Glu Pro Glu Asp Ser Ala Val Tyr Leu Cys Ala Ser
                       100                105                110

Ser Ser Arg Asp Trp Ser Ala Glu Thr Leu Xaa Phe Gly Ser Gly Thr
                       115                120                125

Arg Leu Thr Val Leu Glu Asp Leu Arg Asn Val Thr Pro Pro Lys Val
                 130                135                140

Ser Leu Phe Glu Pro Ser Lys Ala Glu Ile Ala Asn Lys Gln Lys Ala
        145                150                155                160

Thr Leu Val Cys Leu Ala Arg Gly Phe Phe Pro Asp His Val Glu Leu
                       165                170                175

Ser Trp Trp Val Asn Gly Lys Glu Val His Ser Gly Val Ser Thr Asp
                       180                185                190

Pro Gln Ala Tyr Lys Glu Ser Asn Tyr Ser Tyr Cys Leu Ser Ser Arg
                       195                200                205

Leu Arg Val Ser Ala Thr Phe Trp His Asn Pro Arg Asn His Phe Arg
                 210                215                220

Cys Gln Val Gln Phe His Gly Leu Ser Glu Glu Asp Lys Trp Pro Glu
        225                230                235                240

Gly Ser Pro Lys Pro Val Thr Gln Asn Ile Ser Ala Glu Ala Trp Gly
                       245                250                255

Arg Ala Asp Cys Gly Ile Thr Ser Ala Ser Tyr His Gln Gly Val Leu
                       260                265                270

Ser Ala Thr Ile Leu Tyr Glu Ile Leu Leu Gly Lys Ala Thr Leu Tyr
                       275                280                285

Ala Val Leu Val Ser Gly Leu Val Leu Met Ala Met Val Lys Lys Lys
                 290                295                300

Asn Ser
        305

<210> SEQ ID NO 118
        <211> LENGTH: 23
        <212> TYPE: PRT
        <213> ORGANISM: Homo sapiens

<400> SEQUENCE: 118

Met Thr Glu Tyr Lys Leu Val Val Val Gly Ala Gly Gly Val Gly Lys
        1               5                  10                 15

Ser Ala Leu Thr Ile Gln Leu
                        20

<210> SEQ ID NO 119
        <211> LENGTH: 23
        <212> TYPE: PRT
        <213> ORGANISM: Homo sapiens
```

-continued

<400> SEQUENCE: 119

Met Thr Glu Tyr Lys Leu Val Val Val Gly Ala Asp Gly Val Gly Lys
1               5                   10                  15

Ser Ala Leu Thr Ile Gln Leu
            20

<210> SEQ ID NO 120
<211> LENGTH: 23
<212> TYPE: PRT
<213> ORGANISM: Homo sapiens

<400> SEQUENCE: 120

Met Thr Glu Tyr Lys Leu Val Val Val Gly Ala Val Gly Val Gly Lys
1               5                   10                  15

Ser Ala Leu Thr Ile Gln Leu
            20

<210> SEQ ID NO 121
<211> LENGTH: 188
<212> TYPE: PRT
<213> ORGANISM: Homo sapiens

<400> SEQUENCE: 121

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 122
<211> LENGTH: 188
<212> TYPE: PRT
<213> ORGANISM: Homo sapiens

<400> SEQUENCE: 122

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

```
Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 123
<211> LENGTH: 188
<212> TYPE: PRT
<213> ORGANISM: Homo sapiens

<400> SEQUENCE: 123

Met Thr Glu Tyr Lys Leu Val Val Val Gly Ala Val Gly Val Gly Lys
 1               5                  10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 124
<211> LENGTH: 9
<212> TYPE: PRT
```

<213> ORGANISM: Homo sapiens

<400> SEQUENCE: 124

Val Val Val Gly Ala Asp Gly Val Gly
1               5

<210> SEQ ID NO 125
<211> LENGTH: 6
<212> TYPE: PRT
<213> ORGANISM: Murine

<400> SEQUENCE: 125

Asp Pro Asn Ser Tyr Tyr
1               5

<210> SEQ ID NO 126
<211> LENGTH: 7
<212> TYPE: PRT
<213> ORGANISM: Murine

<400> SEQUENCE: 126

Val Phe Ser Ser Thr Glu Ile
1               5

<210> SEQ ID NO 127
<211> LENGTH: 16
<212> TYPE: PRT
<213> ORGANISM: Murine

<400> SEQUENCE: 127

Cys Ala Val Ser Gly Gly Thr Asn Ser Ala Gly Asn Lys Leu Thr Phe
1               5                   10                  15

<210> SEQ ID NO 128
<211> LENGTH: 5
<212> TYPE: PRT
<213> ORGANISM: Murine

<400> SEQUENCE: 128

Leu Gly His Asp Thr
1               5

<210> SEQ ID NO 129
<211> LENGTH: 6
<212> TYPE: PRT
<213> ORGANISM: Murine

<400> SEQUENCE: 129

Tyr Asn Asn Lys Gln Leu
1               5

<210> SEQ ID NO 130
<211> LENGTH: 14
<212> TYPE: PRT
<213> ORGANISM: Murine

<400> SEQUENCE: 130

Cys Ala Ser Ser Arg Asp Trp Gly Pro Ala Glu Gln Phe Phe
1               5                   10

<210> SEQ ID NO 131
<211> LENGTH: 137
<212> TYPE: PRT
<213> ORGANISM: Murine

-continued

<400> SEQUENCE: 131

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Thr Cys Thr Tyr Thr Asp
        35                  40                  45

Pro Asn Ser Tyr Tyr Phe Phe Trp Tyr Lys Gln Glu Pro Gly Ala Ser
    50                  55                  60

Leu Gln Leu Leu Met Lys Val Phe Ser Thr Glu Ile Asn Glu Gly
65                  70                  75                  80

Gln Gly Phe Thr Val Leu Leu Asn Lys Lys Asp Lys Arg Leu Ser Leu
                85                  90                  95

Asn Leu Thr Ala Ala His Pro Gly Asp Ser Ala Ala Tyr Phe Cys Ala
            100                 105                 110

Val Ser Gly Gly Thr Asn Ser Ala Gly Asn Lys Leu Thr Phe Gly Ile
        115                 120                 125

Gly Thr Arg Val Leu Val Arg Pro Asp
    130                 135

<210> SEQ ID NO 132
<211> LENGTH: 133
<212> TYPE: PRT
<213> ORGANISM: Murine

<400> SEQUENCE: 132

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Arg Asp Trp Gly Pro Ala Glu Gln Phe Phe Gly Pro Gly Thr Arg
        115                 120                 125

Leu Thr Val Leu Glu
    130

<210> SEQ ID NO 133
<211> LENGTH: 273
<212> TYPE: PRT
<213> ORGANISM: Murine

<400> SEQUENCE: 133

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Thr Cys Thr Tyr Thr Asp

```
                35                  40                  45
Pro Asn Ser Tyr Tyr Phe Phe Trp Tyr Lys Gln Glu Pro Gly Ala Ser
 50                  55                  60

Leu Gln Leu Leu Met Lys Val Phe Ser Ser Thr Glu Ile Asn Glu Gly
 65                  70                  75                  80

Gln Gly Phe Thr Val Leu Leu Asn Lys Lys Asp Lys Arg Leu Ser Leu
                 85                  90                  95

Asn Leu Thr Ala Ala His Pro Gly Asp Ser Ala Ala Tyr Phe Cys Ala
             100                 105                 110

Val Ser Gly Gly Thr Asn Ser Ala Gly Asn Lys Leu Thr Phe Gly Ile
         115                 120                 125

Gly Thr Arg Val Leu Val Arg Pro Asp Ile Gln Asn Pro Glu Pro Ala
     130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 134
<211> LENGTH: 305
<212> TYPE: PRT
<213> ORGANISM: Murine

<400> SEQUENCE: 134

Met Gly Cys Arg Leu Leu Ser Cys Val Ala Phe Cys Leu Leu Gly Ile
 1               5                  10                  15

Gly Pro Leu Glu Thr Ala Val Phe Gln Thr Pro Asn Tyr His Val Thr
                 20                  25                  30

Gln Val Gly Asn Glu Val Ser Phe Asn Cys Lys Gln Thr Leu Gly His
             35                  40                  45

Asp Thr Met Tyr Trp Tyr Lys Gln Asp Ser Lys Lys Leu Leu Lys Ile
 50                  55                  60

Met Phe Ser Tyr Asn Asn Lys Gln Leu Ile Val Asn Glu Thr Val Pro
 65                  70                  75                  80

Arg Arg Phe Ser Pro Gln Ser Ser Asp Lys Ala His Leu Asn Leu Arg
                 85                  90                  95

Ile Lys Ser Val Glu Pro Glu Asp Ser Ala Val Tyr Leu Cys Ala Ser
             100                 105                 110

Ser Arg Asp Trp Gly Pro Ala Glu Gln Phe Phe Gly Pro Gly Thr Arg
         115                 120                 125

Leu Thr Val Leu Glu Asp Leu Arg Asn Val Thr Pro Pro Lys Val Ser
```

```
                130                 135                 140
Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
                195                 200                 205

Arg Val Ser Ala Thr Phe Trp His Asn Pro Arg Asn His Phe Arg Cys
        210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
                260                 265                 270

Ala Thr Ile Leu Tyr Glu Ile Leu Leu Gly Lys Ala Thr Leu Tyr Ala
            275                 280                 285

Val Leu Val Ser Gly Leu Val Leu Met Ala Met Val Lys Lys Lys Asn
290                 295                 300

Ser
305

<210> SEQ ID NO 135
<211> LENGTH: 136
<212> TYPE: PRT
<213> ORGANISM: Murine

<400> SEQUENCE: 135

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
                20                  25                  30

Val Pro Lys Thr Met Glu Ser Gly Thr Phe Ile Thr Asp Lys Thr Val
            35                  40                  45

Leu Asp Met Lys Ala Met Asp Ser Lys Ser Asn Gly Ala Ile Ala Trp
50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
                100                 105                 110

Met Gly Leu Arg Ile Leu Leu Leu Lys Val Ala Gly Phe Asn Leu Leu
            115                 120                 125

Met Thr Leu Arg Leu Trp Ser Ser
        130                 135

<210> SEQ ID NO 136
<211> LENGTH: 172
<212> TYPE: PRT
<213> ORGANISM: Murine

<400> SEQUENCE: 136

Asp Leu Arg Asn Val Thr Pro Pro Lys Val Ser Leu Phe Glu Pro Ser
```

```
                1               5                   10                  15
            Lys Ala Glu Ile Ala Asn Lys Gln Lys Ala Thr Leu Val Cys Leu Ala
                            20                  25                  30

Arg Gly Phe Phe Pro Asp His Val Glu Leu Ser Trp Trp Val Asn Gly
                        35                  40                  45

Lys Glu Val His Ser Gly Val Ser Thr Asp Pro Gln Ala Tyr Lys Glu
                    50                  55                  60

Ser Asn Tyr Ser Tyr Cys Leu Ser Ser Arg Leu Arg Val Ser Ala Thr
            65                  70                  75                  80

Phe Trp His Asn Pro Arg Asn His Phe Arg Cys Gln Val Gln Phe His
                            85                  90                  95

Gly Leu Ser Glu Glu Asp Lys Trp Pro Glu Gly Ser Pro Lys Pro Val
                        100                 105                 110

Thr Gln Asn Ile Ser Ala Glu Ala Trp Gly Arg Ala Asp Cys Gly Ile
                    115                 120                 125

Thr Ser Ala Ser Tyr His Gln Gly Val Leu Ser Ala Thr Ile Leu Tyr
                130                 135                 140

Glu Ile Leu Leu Gly Lys Ala Thr Leu Tyr Ala Val Leu Val Ser Gly
            145                 150                 155                 160

Leu Val Leu Met Ala Met Val Lys Lys Lys Asn Ser
                            165                 170

<210> SEQ ID NO 137
<211> LENGTH: 6
<212> TYPE: PRT
<213> ORGANISM: Murine

<400> SEQUENCE: 137

Asn Asp Met Phe Asp Tyr
1               5

<210> SEQ ID NO 138
<211> LENGTH: 7
<212> TYPE: PRT
<213> ORGANISM: Murine

<400> SEQUENCE: 138

Val Arg Ser Asn Val Asp Lys
1               5

<210> SEQ ID NO 139
<211> LENGTH: 15
<212> TYPE: PRT
<213> ORGANISM: Murine

<400> SEQUENCE: 139

Cys Ala Ala Gly Asp Ser Gly Gly Ser Asn Tyr Lys Leu Thr Phe
1               5                   10                  15

<210> SEQ ID NO 140
<211> LENGTH: 5
<212> TYPE: PRT
<213> ORGANISM: Murine

<400> SEQUENCE: 140

Asn Ser His Asn Tyr
1               5

<210> SEQ ID NO 141
<211> LENGTH: 6
```

```
<212> TYPE: PRT
<213> ORGANISM: Murine

<400> SEQUENCE: 141

Ser Tyr Gly Ala Gly Asn
1               5

<210> SEQ ID NO 142
<211> LENGTH: 14
<212> TYPE: PRT
<213> ORGANISM: Murine

<400> SEQUENCE: 142

Cys Ala Ser Ala Ser Trp Gly Gly Tyr Ala Glu Gln Phe Phe
1               5                   10

<210> SEQ ID NO 143
<211> LENGTH: 141
<212> TYPE: PRT
<213> ORGANISM: Murine

<400> SEQUENCE: 143

Met Thr Gly Phe Leu Lys Ala Leu Leu Val Leu Cys Leu Arg Pro
1               5                   10                  15

Glu Trp Ile Lys Ser Gln Gln Lys Thr Gly Gly Gln Gln Val Lys Gln
                20                  25                  30

Ser Ser Pro Ser Leu Thr Val Gln Glu Gly Gly Ile Leu Ile Leu Asn
            35                  40                  45

Cys Asp Tyr Glu Asn Asp Met Phe Asp Tyr Phe Ala Trp Tyr Lys Lys
        50                  55                  60

Tyr Pro Asp Asn Ser Pro Thr Leu Leu Ile Ser Val Arg Ser Asn Val
65                  70                  75                  80

Asp Lys Arg Glu Asp Gly Arg Phe Thr Val Phe Leu Asn Lys Ser Gly
                    85                  90                  95

Lys His Phe Ser Leu His Ile Thr Ala Ser Gln Pro Glu Asp Thr Ala
                100                 105                 110

Val Tyr Leu Cys Ala Ala Gly Asp Ser Gly Gly Ser Asn Tyr Lys Leu
            115                 120                 125

Thr Phe Gly Lys Gly Thr Leu Leu Thr Val Thr Pro Asn
        130                 135                 140

<210> SEQ ID NO 144
<211> LENGTH: 131
<212> TYPE: PRT
<213> ORGANISM: Murine

<400> SEQUENCE: 144

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
                20                  25                  30

Gly Gly Asn Val Thr Leu Ser Cys Arg Gln Thr Asn Ser His Asn Tyr
            35                  40                  45

Met Tyr Trp Tyr Arg Gln Asp Thr Gly His Gly Leu Arg Leu Ile His
        50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                    85                  90                  95
```

-continued

```
Leu Ala Ser Pro Ser Gln Thr Ser Leu Tyr Phe Cys Ala Ser Ala Ser
            100                 105                 110

Trp Gly Gly Tyr Ala Glu Gln Phe Phe Gly Pro Gly Thr Arg Leu Thr
        115                 120                 125

Val Leu Glu
        130

<210> SEQ ID NO 145
<211> LENGTH: 277
<212> TYPE: PRT
<213> ORGANISM: Murine

<400> SEQUENCE: 145

Met Thr Gly Phe Leu Lys Ala Leu Leu Leu Val Leu Cys Leu Arg Pro
1               5                   10                  15

Glu Trp Ile Lys Ser Gln Gln Lys Thr Gly Gly Gln Val Lys Gln
            20                  25                  30

Ser Ser Pro Ser Leu Thr Val Gln Glu Gly Gly Ile Leu Ile Leu Asn
        35                  40                  45

Cys Asp Tyr Glu Asn Asp Met Phe Asp Tyr Phe Ala Trp Tyr Lys Lys
    50                  55                  60

Tyr Pro Asp Asn Ser Pro Thr Leu Leu Ile Ser Val Arg Ser Asn Val
65                  70                  75                  80

Asp Lys Arg Glu Asp Gly Arg Phe Thr Val Phe Leu Asn Lys Ser Gly
                85                  90                  95

Lys His Phe Ser Leu His Ile Thr Ala Ser Gln Pro Glu Asp Thr Ala
            100                 105                 110

Val Tyr Leu Cys Ala Ala Gly Asp Ser Gly Gly Ser Asn Tyr Lys Leu
        115                 120                 125

Thr Phe Gly Lys Gly Thr Leu Leu Thr Val Thr Pro Asn Ile Gln Asn
    130                 135                 140

Pro Glu Pro Ala Val Tyr Gln Leu Lys Asp Pro Arg Ser Gln Asp Ser
145                 150                 155                 160

Thr Leu Cys Leu Phe Thr Asp Phe Asp Ser Gln Ile Asn Val Pro Lys
                165                 170                 175

Thr Met Glu Ser Gly Thr Phe Ile Thr Asp Lys Thr Val Leu Asp Met
            180                 185                 190

Lys Ala Met Asp Ser Lys Ser Asn Gly Ala Ile Ala Trp Ser Asn Gln
        195                 200                 205

Thr Ser Phe Thr Cys Gln Asp Ile Phe Lys Glu Thr Asn Ala Thr Tyr
    210                 215                 220

Pro Ser Ser Asp Val Pro Cys Asp Ala Thr Leu Thr Glu Lys Ser Phe
225                 230                 235                 240

Glu Thr Asp Met Asn Leu Asn Phe Gln Asn Leu Ser Val Met Gly Leu
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 146
<211> LENGTH: 303
<212> TYPE: PRT
<213> ORGANISM: Murine

<400> SEQUENCE: 146
```

```
Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
            35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ala Ser
                100                 105                 110

Trp Gly Gly Tyr Ala Glu Gln Phe Phe Gly Pro Gly Thr Arg Leu Thr
            115                 120                 125

Val Leu Glu Asp Leu Arg Asn Val Thr Pro Pro Lys Val Ser Leu Phe
            130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
            195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
            275                 280                 285

Val Ser Gly Leu Val Leu Met Ala Met Val Lys Lys Asn Ser
            290                 295                 300

<210> SEQ ID NO 147
<211> LENGTH: 136
<212> TYPE: PRT
<213> ORGANISM: Murine

<400> SEQUENCE: 147

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
            35                  40                  45

Leu Asp Met Lys Ala Met Asp Ser Lys Ser Asn Gly Ala Ile Ala Trp
    50                  55                  60

Ser Asn Gln Thr Ser Phe Thr Cys Gln Asp Ile Phe Lys Glu Thr Asn
```

```
                65                  70                  75                  80
Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
            100                 105                 110

Met Gly Leu Arg Ile Leu Leu Lys Val Ala Gly Phe Asn Leu Leu
        115                 120                 125

Met Thr Leu Arg Leu Trp Ser Ser
        130                 135
```

<210> SEQ ID NO 148
<211> LENGTH: 172
<212> TYPE: PRT
<213> ORGANISM: Murine

<400> SEQUENCE: 148

```
Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95

Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Asp Cys Gly Ile
        115                 120                 125

Thr Ser Ala Ser Tyr His Gln Gly Val Leu Ser Ala Thr Ile Leu Tyr
    130                 135                 140

Glu Ile Leu Leu Gly Lys Ala Thr Leu Tyr Ala Val Leu Val Ser Gly
145                 150                 155                 160

Leu Val Leu Met Ala Met Val Lys Lys Lys Asn Ser
                165                 170
```

<210> SEQ ID NO 149
<211> LENGTH: 5
<212> TYPE: PRT
<213> ORGANISM: Murine

<400> SEQUENCE: 149

```
Thr Thr Met Arg Ser
1               5
```

<210> SEQ ID NO 150
<211> LENGTH: 5
<212> TYPE: PRT
<213> ORGANISM: Murine

<400> SEQUENCE: 150

```
Leu Ala Ser Gly Thr
1               5
```

<210> SEQ ID NO 151

```
<211> LENGTH: 15
<212> TYPE: PRT
<213> ORGANISM: Murine

<400> SEQUENCE: 151

Cys Ala Ala Asp Ser Ser Asn Thr Gly Tyr Gln Asn Phe Tyr Phe
1               5                   10                  15

<210> SEQ ID NO 152
<211> LENGTH: 5
<212> TYPE: PRT
<213> ORGANISM: Murine

<400> SEQUENCE: 152

Ser Gly His Leu Ser
1               5

<210> SEQ ID NO 153
<211> LENGTH: 6
<212> TYPE: PRT
<213> ORGANISM: Murine

<400> SEQUENCE: 153

His Tyr Asp Lys Met Glu
1               5

<210> SEQ ID NO 154
<211> LENGTH: 15
<212> TYPE: PRT
<213> ORGANISM: Murine

<400> SEQUENCE: 154

Cys Ala Ser Ser Leu Thr Asp Pro Leu Asp Ser Asp Tyr Thr Phe
1               5                   10                  15

<210> SEQ ID NO 155
<211> LENGTH: 133
<212> TYPE: PRT
<213> ORGANISM: Murine

<400> SEQUENCE: 155

Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Gly Tyr Gln Asn Phe Tyr Phe Gly Lys Gly Thr Ser Leu
        115                 120                 125

Thr Val Ile Pro Asn
    130

<210> SEQ ID NO 156
```

<211> LENGTH: 143
<212> TYPE: PRT
<213> ORGANISM: Murine

<400> SEQUENCE: 156

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
            20                  25                  30

Val Val Gln Ser Pro Arg Tyr Ile Ile Lys Gly Lys Gly Glu Arg Ser
        35                  40                  45

Ile Leu Lys Cys Ile Pro Ile Ser Gly His Leu Ser Val Ala Trp Tyr
50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Thr Asp Pro Leu
        115                 120                 125

Asp Ser Asp Tyr Thr Phe Gly Ser Gly Thr Arg Leu Leu Val Ile
130                 135                 140

<210> SEQ ID NO 157
<211> LENGTH: 269
<212> TYPE: PRT
<213> ORGANISM: Murine

<400> SEQUENCE: 157

Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Gly Tyr Gln Asn Phe Tyr Phe Gly Lys Gly Thr Ser Leu
        115                 120                 125

Thr Val Ile Pro Asn Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

```
Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
                260                 265
```

<210> SEQ ID NO 158
<211> LENGTH: 316
<212> TYPE: PRT
<213> ORGANISM: Murine

<400> SEQUENCE: 158

```
Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
                20                  25                  30

Val Val Gln Ser Pro Arg Tyr Ile Ile Lys Gly Lys Gly Glu Arg Ser
            35                  40                  45

Ile Leu Lys Cys Ile Pro Ile Ser Gly His Leu Ser Val Ala Trp Tyr
        50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
                100                 105                 110

Glu Asp Ser Ala Val Tyr Phe Cys Ala Ser Ser Leu Thr Asp Pro Leu
            115                 120                 125

Asp Ser Asp Tyr Thr Phe Gly Ser Gly Thr Arg Leu Leu Val Ile Glu
        130                 135                 140

Asp Leu Arg Asn Val Thr Pro Pro Lys Val Ser Leu Phe Glu Pro Ser
145                 150                 155                 160

Lys Ala Glu Ile Ala Asn Lys Gln Lys Ala Thr Leu Val Cys Leu Ala
                165                 170                 175

Arg Gly Phe Phe Pro Asp His Val Glu Leu Ser Trp Trp Val Asn Gly
                180                 185                 190

Lys Glu Val His Ser Gly Val Ser Thr Asp Pro Gln Ala Tyr Lys Glu
            195                 200                 205

Ser Asn Tyr Ser Tyr Cys Leu Ser Ser Arg Leu Arg Val Ser Ala Thr
        210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Asn Ile Ser Ala Glu Ala Trp Gly Arg Ala Asp Cys Gly Ile
                260                 265                 270

Thr Ser Ala Ser Tyr Gln Gln Gly Val Leu Ser Ala Thr Ile Leu Tyr
            275                 280                 285

Glu Ile Leu Leu Gly Lys Ala Thr Leu Tyr Ala Val Leu Val Ser Thr
        290                 295                 300

Leu Val Val Met Ala Met Val Lys Arg Lys Asn Ser
```

305        310        315

<210> SEQ ID NO 159
<211> LENGTH: 136
<212> TYPE: PRT
<213> ORGANISM: Murine

<400> SEQUENCE: 159

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
        35                  40                  45

Leu Asp Met Lys Ala Met Asp Ser Lys Ser Asn Gly Ala Ile Ala Trp
    50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
            100                 105                 110

Met Gly Leu Arg Ile Leu Leu Leu Lys Val Ala Gly Phe Asn Leu Leu
        115                 120                 125

Met Thr Leu Arg Leu Trp Ser Ser
    130                 135

<210> SEQ ID NO 160
<211> LENGTH: 173
<212> TYPE: PRT
<213> ORGANISM: Murine

<400> SEQUENCE: 160

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

```
<210> SEQ ID NO 161
<211> LENGTH: 13
<212> TYPE: PRT
<213> ORGANISM: Murine

<400> SEQUENCE: 161

Cys Ala Ala Leu Asn Thr Gly Tyr Gln Asn Phe Tyr Phe
1               5                   10

<210> SEQ ID NO 162
<211> LENGTH: 612
<212> TYPE: PRT
<213> ORGANISM: Artificial Sequence
<220> FEATURE:
<223> OTHER INFORMATION: Synthetic

<400> SEQUENCE: 162

Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
                20                  25                  30

Leu His Glu Gly Thr Asp Ser Ala Leu Arg Cys Asn Phe Thr Thr Thr
            35                  40                  45

Met Arg Ser Val Gln Trp Phe Arg Gln Asn Ser Arg Gly Ser Leu Ile
        50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Gly Tyr Gln Asn Phe Tyr Phe Gly Lys Gly Thr Ser Leu
        115                 120                 125

Thr Val Ile Pro Asn Ile Gln Asn Pro Glu Pro Ala Val Tyr Gln Leu
130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser Arg Ala Lys
            260                 265                 270

Arg Ser Gly Ser Gly Ala Thr Asn Phe Ser Leu Leu Lys Gln Ala Gly
        275                 280                 285

Asp Val Glu Glu Asn Pro Gly Pro Met Ser Asn Thr Ala Phe Pro Asp
    290                 295                 300

Pro Ala Trp Asn Thr Thr Leu Leu Ser Trp Val Ala Leu Phe Leu Leu
305                 310                 315                 320
```

Gly Thr Ser Ser Ala Asn Ser Gly Val Val Gln Ser Pro Arg Tyr Ile
                325                 330                 335

Ile Lys Gly Lys Gly Glu Arg Ser Ile Leu Lys Cys Ile Pro Ile Ser
            340                 345                 350

Gly His Leu Ser Val Ala Trp Tyr Gln Gln Thr Gln Gly Gln Glu Leu
        355                 360                 365

Lys Phe Phe Ile Gln His Tyr Asp Lys Met Glu Arg Asp Lys Gly Asn
    370                 375                 380

Leu Pro Ser Arg Phe Ser Val Gln Gln Phe Asp Asp Tyr His Ser Glu
385                 390                 395                 400

Met Asn Met Ser Ala Leu Glu Leu Glu Asp Ser Ala Val Tyr Phe Cys
                405                 410                 415

Ala Ser Ser Leu Thr Asp Pro Leu Asp Ser Asp Tyr Thr Phe Gly Ser
            420                 425                 430

Gly Thr Arg Leu Leu Val Ile Glu Asp Leu Arg Asn Val Thr Pro Pro
        435                 440                 445

Lys Val Ser Leu Phe Glu Pro Ser Lys Ala Glu Ile Ala Asn Lys Gln
    450                 455                 460

Lys Ala Thr Leu Val Cys Leu Ala Arg Gly Phe Phe Pro Asp His Val
465                 470                 475                 480

Glu Leu Ser Trp Trp Val Asn Gly Lys Glu Val His Ser Gly Val Ser
                485                 490                 495

Thr Asp Pro Gln Ala Tyr Lys Glu Ser Asn Tyr Ser Tyr Cys Leu Ser
            500                 505                 510

Ser Arg Leu Arg Val Ser Ala Thr Phe Trp His Asn Pro Arg Asn His
        515                 520                 525

Phe Arg Cys Gln Val Gln Phe His Gly Leu Ser Glu Glu Asp Lys Trp
    530                 535                 540

Pro Glu Gly Ser Pro Lys Pro Val Thr Gln Asn Ile Ser Ala Glu Ala
545                 550                 555                 560

Trp Gly Arg Ala Asp Cys Gly Ile Thr Ser Ala Ser Tyr Gln Gln Gly
                565                 570                 575

Val Leu Ser Ala Thr Ile Leu Tyr Glu Ile Leu Leu Gly Lys Ala Thr
            580                 585                 590

Leu Tyr Ala Val Leu Val Ser Thr Leu Val Val Met Ala Met Val Lys
        595                 600                 605

Arg Lys Asn Ser
    610

<210> SEQ ID NO 163
<211> LENGTH: 1839
<212> TYPE: DNA
<213> ORGANISM: Artificial Sequence
<220> FEATURE:
<223> OTHER INFORMATION: Synthetic

<400> SEQUENCE: 163
atgcagagga acctgggagc tgtgctgggg attctgtggg tgcagatttg ctgggtgaga      60
ggggatcagg tggagcagag tccttcagcc ctgagcctcc acgagggaac cgattctgct     120
ctgagatgca attttacgac caccatgagg agtgtgcagt ggttccgaca gaattccagg     180
ggcagcctca tcagtttgtt ctacttggct tcaggaacaa aggagaatgg gaggctaaag     240
tcagcatttg attctaagga gcggcgctac agcaccctgc acatcaggga tgcccagctg     300
gaggactcag gcacttactt ctgtgctgct gactcttcga acacgggtta ccagaacttc     360

```
tattttggga aaggaacaag tttgactgtc attccaaaca tccagaaccc agaacctgct    420
gtgtaccagt taaaagatcc tcggtctcag gacagcaccc tctgcctgtt caccgacttt    480
gactcccaaa tcaatgtgcc gaaaaccatg aatctggaa cgttcatcac tgacaaaact    540
gtgctggaca tgaaagctat ggattccaag agcaatgggg ccattgcctg gagcaaccag    600
acaagcttca cctgccaaga tatcttcaaa gagaccaacg ccacctaccc cagttcagac    660
gttccctgtg atgccacgtt gaccgagaaa agctttgaaa cagatatgaa cctgaacttt    720
caaaacctgt cagttatggg actccgaatc ctcctgctga agtagcggg atttaacctg    780 ctcatgacgc tgaggctgtg gtccagtcgg gccaagcggt ccggatccgg agccaccaac    840
ttcagcctgc tgaagcaggc cggcgacgtg gaggagaacc ccggccccat gtctaacact    900
gccttccctg accccgcctg gaacaccacc ctgctatctt gggttgctct ctttctcctg    960
ggaacaagtt cagcaaattc tggggttgtc cagtctccaa gatacataat caaaggaaag   1020
ggagaaaggt ccattctaaa atgtattccc atctctggac atctctctgt ggcctggtat   1080
caacagactc aggggcagga actaaagttc ttcattcagc attatgataa aatggagaga   1140
gataaaggaa acctgcccag cagattctca gtccaacagt ttgatgacta tcactctgag   1200
atgaacatga gtgccttgga gctagaggac tctgccgtgt acttctgtgc cagctctctc   1260
acagatccgc tagactccga ctacaccttc ggctcaggga ccaggctttt ggtaatagag   1320
gatctgagaa atgtgactcc acccaaggtc tccttgtttg agccatcaaa agcagagatt   1380
gcaaacaaac aaaaggctac cctcgtgtgc ttggccaggg gcttcttccc tgaccacgtg   1440
gagctgagct ggtgggtgaa tggcaaggag gtccacagtg gggtcagcac ggaccctcag   1500
gcctacaagg agagcaatta tagctactgc ctgagcagcc gcctgagggt ctctgctacc   1560
ttctggcaca atcctcgcaa ccacttccgc tgccaagtgc agttccatgg gctttcagag   1620
gaggacaagt ggccagaggg ctcacccaaa cctgtcacac agaacatcag tgcagaggcc   1680
tggggccgag cagactgtgg gattacctca gcatcctatc aacaagggt cttgtctgcc   1740 accatcctct atgagatcct gctagggaaa gccaccctgt atgctgtgct tgtcagtaca   1800
ctggtggtga tggctatggt caaaagaaag aattcatga                          1839

<210> SEQ ID NO 164
<211> LENGTH: 15
<212> TYPE: DNA
<213> ORGANISM: Artificial Sequence
<220> FEATURE:
<223> OTHER INFORMATION: Synthetic

<400> SEQUENCE: 164
accaccatga ggagt                                                      15

<210> SEQ ID NO 165
<211> LENGTH: 15
<212> TYPE: DNA
<213> ORGANISM: Artificial Sequence
<220> FEATURE:
<223> OTHER INFORMATION: Synthetic

<400> SEQUENCE: 165
ttggcttcag gaaca                                                      15

<210> SEQ ID NO 166
<211> LENGTH: 39
<212> TYPE: DNA
```

```
<213> ORGANISM: Artificial Sequence
<220> FEATURE:
<223> OTHER INFORMATION: Synthetic

<400> SEQUENCE: 166
gctgctgact cttcgaacac gggttaccag aacttctat                     39

<210> SEQ ID NO 167
<211> LENGTH: 15
<212> TYPE: DNA
<213> ORGANISM: Artificial Sequence
<220> FEATURE:
<223> OTHER INFORMATION: Synthetic

<400> SEQUENCE: 167
tctggacatc tctct                                               15

<210> SEQ ID NO 168
<211> LENGTH: 18
<212> TYPE: DNA
<213> ORGANISM: Artificial Sequence
<220> FEATURE:
<223> OTHER INFORMATION: Synthetic

<400> SEQUENCE: 168
cattatgata aaatggag                                            18

<210> SEQ ID NO 169
<211> LENGTH: 39
<212> TYPE: DNA
<213> ORGANISM: Artificial Sequence
<220> FEATURE:
<223> OTHER INFORMATION: Synthetic

<400> SEQUENCE: 169
gccagctctc tcacagatcc gctagactcc gactacacc                     39

<210> SEQ ID NO 170
<211> LENGTH: 399
<212> TYPE: DNA
<213> ORGANISM: Artificial Sequence
<220> FEATURE:
<223> OTHER INFORMATION: Synthetic

<400> SEQUENCE: 170
atgcagagga acctgggagc tgtgctgggg attctgtggg tgcagatttg ctgggtgaga    60
ggggatcagg tggagcagag tccttcagcc ctgagcctcc acgagggaac cgattctgct   120
ctgagatgca attttacgac caccatgagg agtgtgcagt ggttccgaca gaattccagg   180
ggcagcctca tcagtttgtt ctacttggct tcaggaacaa aggagaatgg gaggctaaag   240
tcagcatttg attctaagga gcggcgctac agcaccctgc acatcaggga tgcccagctg   300
gaggactcag gcacttactt ctgtgctgct gactcttcga acacgggtta ccagaacttc   360
tattttggga aaggaacaag tttgactgtc attccaaac                         399

<210> SEQ ID NO 171
<211> LENGTH: 429
<212> TYPE: DNA
<213> ORGANISM: Artificial Sequence
<220> FEATURE:
<223> OTHER INFORMATION: Synthetic

<400> SEQUENCE: 171
atgtctaaca ctgccttccc tgaccccgcc tggaacacca ccctgctatc ttgggttgct    60
```

```
ctctttctcc tgggaacaag ttcagcaaat tctggggttg tccagtctcc aagatacata    120
atcaaaggaa agggagaaag gtccattcta aaatgtattc ccatctctgg acatctctct    180
gtggcctggt atcaacagac tcaggggcag gaactaaagt tcttcattca gcattatgat    240
aaaatggaga gagataaagg aaacctgccc agcagattct cagtccaaca gtttgatgac    300
tatcactctg agatgaacat gagtgccttg gagctagagg actctgccgt gtacttctgt    360
gccagctctc tcacagatcc gctagactcc gactacacct tcggctcagg gaccaggctt    420
ttggtaata                                                            429
```

<210> SEQ ID NO 172  
<211> LENGTH: 807  
<212> TYPE: DNA  
<213> ORGANISM: Artificial Sequence  
<220> FEATURE:  
<223> OTHER INFORMATION: Synthetic
<400> SEQUENCE: 172

```
atgcagagga acctgggagc tgtgctgggg attctgtggg tgcagatttg ctgggtgaga     60
ggggatcagg tggagcagag tccttcagcc ctgagcctcc acgagggaac cgattctgct    120
ctgagatgca attttacgac caccatgagg agtgtgcagt ggttccgaca gaattccagg    180
ggcagcctca tcagtttgtt ctacttggct tcaggaacaa aggagaatgg gaggctaaag    240
tcagcatttg attctaagga gcggcgctac agcaccctgc atcaggga tgcccagctg      300 gaggactcag gcacttactt ctgtgctgct gactcttcga acacgggtta ccagaacttc    360
tattttggga aaggaacaag tttgactgtc attccaaaca tccagaaccc agaacctgct    420
gtgtaccagt taaagatcc tcggtctcag gacagcaccc tctgcctgtt caccgacttt    480
gactcccaaa tcaatgtgcc gaaaaccatg gaatctggaa cgttcatcac tgacaaaact    540
gtgctggaca tgaaagctat ggattccaag agcaatgggg ccattgcctg gagcaaccag    600
acaagcttca cctgccaaga tatcttcaaa gagaccaacg ccacctaccc cagttcagac    660
gttccctgtg atgccacgtt gaccgagaaa agctttgaaa cagatatgaa cctgaacttt    720
caaaacctgt cagttatggg actccgaatc ctcctgctga aagtagcggg atttaacctg    780
ctcatgacgc tgaggctgtg gtccagt                                        807
```

<210> SEQ ID NO 173  
<211> LENGTH: 951  
<212> TYPE: DNA  
<213> ORGANISM: Artificial Sequence  
<220> FEATURE:  
<223> OTHER INFORMATION: Synthetic
<400> SEQUENCE: 173

```
atgtctaaca ctgccttccc tgaccccgcc tggaacacca ccctgctatc ttgggttgct     60
ctctttctcc tgggaacaag ttcagcaaat tctggggttg tccagtctcc aagatacata    120
atcaaaggaa agggagaaag gtccattcta aaatgtattc ccatctctgg acatctctct    180
gtggcctggt atcaacagac tcaggggcag gaactaaagt tcttcattca gcattatgat    240
aaaatggaga gagataaagg aaacctgccc agcagattct cagtccaaca gtttgatgac    300
tatcactctg agatgaacat gagtgccttg gagctagagg actctgccgt gtacttctgt    360
gccagctctc tcacagatcc gctagactcc gactacacct tcggctcagg gaccaggctt    420
ttggtaatag aggatctgag aaatgtgact ccacccaagg tctccttgtt tgagccatca    480
```

```
aaagcagaga ttgcaaacaa acaaaaggct accctcgtgt gcttggccag ggcttcttc      540 cctgaccacg tggagctgag ctggtgggtg aatggcaagg aggtccacag tggggtcagc      600
acggaccctc aggcctacaa ggagagcaat tatagctact gcctgagcag ccgcctgagg      660
gtctctgcta ccttctggca caatcctcgc aaccacttcc gctgccaagt gcagttccat      720
gggctttcag aggaggacaa gtggccagag ggctcaccca aacctgtcac acagaacatc      780
agtgcagagg cctggggccg agcagactgt gggattacct cagcatccta tcaacaaggg      840
gtcttgtctg ccaccatcct ctatgagatc ctgctaggga aagccaccct gtatgctgtg      900
cttgtcagta cactggtggt gatggctatg gtcaaaagaa agaattcatg a               951

<210> SEQ ID NO 174
<211> LENGTH: 408
<212> TYPE: DNA
<213> ORGANISM: Artificial Sequence
<220> FEATURE:
<223> OTHER INFORMATION: Synthetic

<400> SEQUENCE: 174
atccagaacc cagaacctgc tgtgtaccag ttaaaagatc ctcggtctca ggacagcacc       60
ctctgcctgt tcaccgactt tgactcccaa atcaatgtgc cgaaaaccat ggaatctgga      120
acgttcatca ctgacaaaac tgtgctggac atgaaagcta tggattccaa gagcaatggg      180
gccattgcct ggagcaacca gacaagcttc acctgccaag atatcttcaa agagaccaac      240
gccacctacc ccagttcaga cgttccctgt gatgccacgt tgaccgagaa agctttgaa       300 acagatatga acctaaactt tcaaaaactg tcagttatgg gactccgaat cctcctgctg      360
aaagtagcgg gatttaacct gctcatgacg ctgaggctgt ggtccagt                   408

<210> SEQ ID NO 175
<211> LENGTH: 522
<212> TYPE: DNA
<213> ORGANISM: Artificial Sequence
<220> FEATURE:
<223> OTHER INFORMATION: Synthetic

<400> SEQUENCE: 175
gaggatctga gaaatgtgac tccacccaag gtctccttgt ttgagccatc aaaagcagag       60
attgcaaaca acaaaaggc taccctcgtg tgcttggcca ggggcttctt ccctgaccac      120
gtggagctga gctggtgggt gaatggcaag gaggtccaca gtggggtcag cacggaccct      180
caggcctaca aggagagcaa ttatagctac tgcctgagca gccgcctgag ggtctctgct      240
accttctggc acaatcctcg caaccacttc cgctgccaag tgcagttcca tgggctttca      300
gaggaggaca agtggccaga gggctcaccc aaacctgtca cacagaacat cagtgcagag      360
gcctggggcc gagcagactg tgggattacc tcagcatcct atcaacaagg ggtcttgtct      420
gccaccatcc tctatgagat cctgctaggg aagccaccc tgtatgctgt gcttgtcagt      480
acactggtgg tgatggctat ggtcaaaaga agaattcat ga                          522

<210> SEQ ID NO 176
<211> LENGTH: 1818
<212> TYPE: DNA
<213> ORGANISM: Artificial Sequence
<220> FEATURE:
<223> OTHER INFORMATION: Synthetic

<400> SEQUENCE: 176
atgaagacgg tgactggacc tttgttcctg tgcttctggc tgcagctgaa ctgtgtgagc       60
```

```
agaggcgagc aggtggagca gcgccctcct cacctgagtg tccgggaggg agacagtgcc      120
gttatcacct gcacctacac agaccctaac agttattact tcttctggta caagcaagag      180 ccggggggcaa gtcttcagtt gcttatgaag gttttctcaa gtacggaaat aaacgaagga     240
caaggattca ctgtcctact gaacaagaaa gacaaacgac tctctctgaa cctcacagct     300
gcccatcctg gggactcagc cgcgtacttc tgcgcagtca gtggagggac taacagtgca     360
gggaacaagc taacttttgg aattggaacc agggtgctgg tcaggccaga catccagaac     420
ccagaacctg ctgtgtacca gttaaaagat cctcggtctc aggacagcac cctctgcctg     480
ttcaccgact tgactcccca aatcaatgtg ccgaaaacca tggaatctgg aacgttcatc     540
actgacaaaa ctgtgctgga catgaaagct atggattcca gagcaatgg ggccattgcc      600 tggagcaacc agacaagctt cacctgccaa gatatcttca agagaccaa cgccacctac       660 cccagttcag acgttccctg tgatgccacg ttgaccgaga aaagctttga acagatatg       720 aacctaaact tcaaaaacct gtcagttatg ggactccgaa tcctcctgct gaaagtagcg     780
ggatttaacc tgctcatgac gctgaggctg tggtccagtc gggccaagcg gtccggatcc     840
ggagccacca acttcagcct gctgaagcag gccggcgacg tggaggagaa ccccggcccc     900
atgggctgta ggctcctaag ctgtgtggcc ttctgcctct tgggaatagg ccctttggag     960
acggctgttt tccagactcc aaactatcat gtcacacagg tgggaaatga agtgtctttc     1020
aattgtaagc aaactctggg ccacgatact atgtattggt acaagcaaga ctctaagaaa     1080
ttgctgaaga ttatgtttag ctacaataat aagcaactca ttgtaaacga acagttcca      1140 aggcgcttct cacctcagtc ttcagataaa gctcatttga atcttcgaat caagtctgta    1200
gagccggagg actctgctgt gtatctctgt gccagcagtc gggactgggg gcctgctgag     1260
cagttcttcg gaccagggac acgactcacc gtcctagagg atctgagaaa tgtgactcca     1320
cccaaggtct ccttgtttga gccatcaaaa gcagagattg caaacaaaca aaaggctacc     1380
ctcgtgtgct tggccagggg cttcttccct gaccacgtgg agctgagctg gtgggtgaat     1440
ggcaaggagg tccacagtgg ggtcagcacg gaccctcagg cctacaagga gagcaattat     1500
agctactgcc tgagcagccg cctgagggtc tctgctacct tctggcacaa tcctcgaaac     1560
cacttccgct gccaagtgca gttccatggg cttttcagagg aggacaagtg gccagagggc     1620
tcacccaaac ctgtcacaca gaacatcagt gcagaggcct ggggccgagc agactgtgga     1680
atcacttcag catcctatca tcaggggggtt ctgtctgcaa ccatcctcta tgagatccta     1740
ctggggaagg ccaccctata tgctgtgctg gtcagtggcc tggtgctgat ggccatggtc     1800
aagaaaaaaa attcctga                                                    1818
```

<210> SEQ ID NO 177
<211> LENGTH: 18
<212> TYPE: DNA
<213> ORGANISM: Artificial Sequence
<220> FEATURE:
<223> OTHER INFORMATION: Synthetic

<400> SEQUENCE: 177
gaccctaaca gttattac                                                    18

<210> SEQ ID NO 178
<211> LENGTH: 21
<212> TYPE: DNA
<213> ORGANISM: Artificial Sequence
<220> FEATURE:

<223> OTHER INFORMATION: Synthetic

<400> SEQUENCE: 178
gttttctcaa gtacggaaat a                                            21

<210> SEQ ID NO 179
<211> LENGTH: 48
<212> TYPE: DNA
<213> ORGANISM: Artificial Sequence
<220> FEATURE:
<223> OTHER INFORMATION: Synthetic

<400> SEQUENCE: 179
tgcgcagtca gtggagggac taacagtgca gggaacaagc taactttt               48

<210> SEQ ID NO 180
<211> LENGTH: 15
<212> TYPE: DNA
<213> ORGANISM: Artificial Sequence
<220> FEATURE:
<223> OTHER INFORMATION: Synthetic

<400> SEQUENCE: 180
ctgggccacg atact                                                   15

<210> SEQ ID NO 181
<211> LENGTH: 18
<212> TYPE: DNA
<213> ORGANISM: Artificial Sequence
<220> FEATURE:
<223> OTHER INFORMATION: Synthetic

<400> SEQUENCE: 181
tacaataata agcaactc                                                18

<210> SEQ ID NO 182
<211> LENGTH: 42
<212> TYPE: DNA
<213> ORGANISM: Artificial Sequence
<220> FEATURE:
<223> OTHER INFORMATION: Synthetic

<400> SEQUENCE: 182
tgtgccagca gtcgggactg ggggcctgct gagcagttct tc                     42

<210> SEQ ID NO 183
<211> LENGTH: 411
<212> TYPE: DNA
<213> ORGANISM: Artificial Sequence
<220> FEATURE:
<223> OTHER INFORMATION: Synthetic

<400> SEQUENCE: 183
atgaagacgg tgactggacc tttgttcctg tgcttctggc tgcagctgaa ctgtgtgagc    60
agaggcgagc aggtggagca gcgccctcct cacctgagtg tccgggaggg agacagtgcc   120
gttatcacct gcacctacac agaccctaac agttattact tcttctggta caagcaagag   180
ccgggggcaa gtcttcagtt gcttatgaag gttttctcaa gtacggaaat aaacgaagga   240
caaggattca ctgtcctact gaacaagaaa gacaaacgac tctctctgaa cctcacagct   300
gcccatcctg gggactcagc cgcgtacttc tgcgcagtca gtggagggac taacagtgca   360
gggaacaagc taactttgg aattggaacc agggtgctgg tcaggccaga c            411

```
<210> SEQ ID NO 184
<211> LENGTH: 399
<212> TYPE: DNA
<213> ORGANISM: Artificial Sequence
<220> FEATURE:
<223> OTHER INFORMATION: Synthetic

<400> SEQUENCE: 184
atgggctgta ggctcctaag ctgtgtggcc ttctgcctct tgggaatagg ccctttggag      60
acggctgttt tccagactcc aaactatcat gtcacacagg tgggaaatga agtgtctttc     120
aattgtaagc aaactctggg ccacgatact atgtattggt acaagcaaga ctctaagaaa     180
ttgctgaaga ttatgtttag ctacaataat aagcaactca ttgtaaacga aacagttcca     240
aggcgcttct cacctcagtc ttcagataaa gctcatttga atcttcgaat caagtctgta     300
gagccggagg actctgctgt gtatctctgt gccagcagtc gggactgggg gcctgctgag     360
cagttcttcg gaccagggac acgactcacc gtcctagag                            399

<210> SEQ ID NO 185
<211> LENGTH: 819
<212> TYPE: DNA
<213> ORGANISM: Artificial Sequence
<220> FEATURE:
<223> OTHER INFORMATION: Synthetic

<400> SEQUENCE: 185
atgaagacgg tgactggacc tttgttcctg tgcttctggc tgcagctgaa ctgtgtgagc      60
agaggcgagc aggtggagca gcgcccctcc cacctgagtg tccgggaggg agacagtgcc     120
gttatcacct gcacctacac agaccctaac agttattact tcttctggta caagcaagag     180 ccggggggcaa gtcttcagtt gcttatgaag gttttctcaa gtacgaaaat aaacgaagga     240
caaggattca ctgtcctact gaacaagaaa gacaaacgac tctctctgaa cctcacagct     300
gcccatcctg gggactcagc cgcgtacttc tgcgcagtca gtggagggac taacagtgca     360
gggaacaagc taacttttgg aattggaacc agggtgctgg tcaggccaga catccagaac     420
ccagaacctg ctgtgtacca gttaaaagat cctcggtctc aggacagcac cctctgcctg     480
ttcaccgact ttgactccca aatcaatgtg ccgaaaacca tggaatctgg aacgttcatc     540
actgacaaaa ctgtgctgga catgaaagct atggattcca agagcaatgg ggccattgcc     600
tggagcaacc agacaagctt cacctgccaa gatatcttca agagaccaa cgccacctac     660 cccagttcag acgttccctg tgatgccacg ttgaccgaga aagctttga acagatatg      720 aacctaaact ttcaaaacct gtcagttatg ggactccgaa tcctcctgct gaaagtagcg     780
ggatttaacc tgctcatgac gctgaggctg tggtccagt                            819

<210> SEQ ID NO 186
<211> LENGTH: 918
<212> TYPE: DNA
<213> ORGANISM: Artificial Sequence
<220> FEATURE:
<223> OTHER INFORMATION: Synthetic

<400> SEQUENCE: 186
atgggctgta ggctcctaag ctgtgtggcc ttctgcctct tgggaatagg ccctttggag      60
acggctgttt tccagactcc aaactatcat gtcacacagg tgggaaatga agtgtctttc     120
aattgtaagc aaactctggg ccacgatact atgtattggt acaagcaaga ctctaagaaa     180
ttgctgaaga ttatgtttag ctacaataat aagcaactca ttgtaaacga aacagttcca     240
```

```
aggcgcttct cacctcagtc ttcagataaa gctcatttga atcttcgaat caagtctgta      300
gagccggagg actctgctgt gtatctctgt gccagcagtc gggactgggg gcctgctgag      360
cagttcttcg gaccagggac acgactcacc gtcctagagg atctgagaaa tgtgactcca      420
cccaaggtct ccttgtttga gccatcaaaa gcagagattg caaacaaaca aaaggctacc      480
ctcgtgtgct tggccagggg cttcttccct gaccacgtgg agctgagctg gtgggtgaat      540
ggcaaggagt ccacagtggg gtcagcacg  gaccctcagg cctacaagga gagcaattat      600
agctactgcc tgagcagccg cctgagggtc tctgctacct tctggcacaa tcctcgaaac      660
cacttccgct gccaagtgca gttccatggg ctttcagagg aggacaagtg gccagagggc      720
tcacccaaac ctgtcacaca gaacatcagt gcagaggcct ggggccgagc agactgtgga      780
atcacttcag catcctatca tcaggggtt  ctgtctgcaa ccatcctcta tgagatccta      840
ctggggaagg ccaccctata tgctgtgctg gtcagtggcc tggtgctgat ggccatggtc      900
aagaaaaaaa attcctga                                                   918

<210> SEQ ID NO 187
<211> LENGTH: 408
<212> TYPE: DNA
<213> ORGANISM: Artificial Sequence
<220> FEATURE:
<223> OTHER INFORMATION: Synthetic

<400> SEQUENCE: 187
atccagaacc cagaacctgc tgtgtaccag ttaaaagatc ctcggtctca ggacagcacc       60
ctctgcctgt tcaccgactt tgactcccaa atcaatgtgc cgaaaaccat ggaatctgga      120
acgttcatca ctgacaaaac tgtgctggac atgaaagcta tggattccaa gagcaatggg      180
gccattgcct ggagcaacca gacaagcttc acctgccaag atatcttcaa agagaccaac      240
gccacctacc ccagttcaga cgttccctgt gatgccacgt tgaccgagaa agcttttgaa      300
acagatatga acctaaactt tcaaaacctg tcagttatgg gactccgaat cctcctgctg      360
aaagtagcgg gatttaacct gctcatgacg ctgaggctgt ggtccagt               408

<210> SEQ ID NO 188
<211> LENGTH: 519
<212> TYPE: DNA
<213> ORGANISM: Artificial Sequence
<220> FEATURE:
<223> OTHER INFORMATION: Synthetic

<400> SEQUENCE: 188
gatctgagaa atgtgactcc acccaaggtc tccttgtttg agccatcaaa agcagagatt       60
gcaaacaaac aaaaggctac cctcgtgtgc ttggccaggg gcttcttccc tgaccacgtg      120
gagctgagct ggtgggtgaa tggcaaggag tccacagtgg ggtcagcacg gaccctcag       180 gcctacaagg agagcaatta tagctactgc ctgagcagcc gctgagggt  ctctgctacc      240 ttctggcaca atcctcgaaa ccacttccgc tgccaagtgc agttccatgg gctttcagag      300
gaggacaagt ggccagaggg ctcacccaaa cctgtcacac agaacatcag tgcagaggcc      360
tggggccgag cagactgtgg aatcacttca gcatcctatc atcaggggt  tctgtctgca      420 accatcctct atgagatcct actggggaag gccaccctat atgctgtgct ggtcagtggc      480
ctggtgctga tggccatggt caagaaaaaa aattcctga                            519

<210> SEQ ID NO 189
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 189
aatgatatgt ttgactat                                                 18

<210> SEQ ID NO 190
<211> LENGTH: 21
<212> TYPE: DNA
<213> ORGANISM: Artificial Sequence
<220> FEATURE:
<223> OTHER INFORMATION: Synthetic

<400> SEQUENCE: 190
gtacgctcaa atgtggataa g                                             21

<210> SEQ ID NO 191
<211> LENGTH: 45
<212> TYPE: DNA
<213> ORGANISM: Artificial Sequence
<220> FEATURE:
<223> OTHER INFORMATION: Synthetic

<400> SEQUENCE: 191
tgcgcagcag gtgacagtgg aggcagcaat tacaaactga cattt                   45

<210> SEQ ID NO 192
<211> LENGTH: 15
<212> TYPE: DNA
<213> ORGANISM: Artificial Sequence
<220> FEATURE:
<223> OTHER INFORMATION: Synthetic

<400> SEQUENCE: 192
aatagccaca actac                                                    15

<210> SEQ ID NO 193
<211> LENGTH: 18
<212> TYPE: DNA
<213> ORGANISM: Artificial Sequence
<220> FEATURE:
<223> OTHER INFORMATION: Synthetic

<400> SEQUENCE: 193
tcatatggtg ctggcaac                                                 18

<210> SEQ ID NO 194
<211> LENGTH: 42
<212> TYPE: DNA
<213> ORGANISM: Artificial Sequence
<220> FEATURE:
<223> OTHER INFORMATION: Synthetic

<400> SEQUENCE: 194
tgtgccagcg cgagctgggg gggctatgct gagcagttct tc                      42

<210> SEQ ID NO 195
<211> LENGTH: 423
<212> TYPE: DNA
<213> ORGANISM: Artificial Sequence
<220> FEATURE:
<223> OTHER INFORMATION: Synthetic

<400> SEQUENCE: 195
```

```
atgactggct tcctgaaggc cttgctgttg gttctgtgcc tgcggccaga atggataaag    60
agtcaacaga agactggtgg ccagcaagtt aaacaaagct ctccatcgct gactgttcaa   120
gagggaggga tattgatcct gaattgtgat tacgagaatg atatgtttga ctattttgcc   180
tggtacaaaa aataccctga caacagcccc acactcctga tatccgtacg ctcaaatgtg   240
gataagaggg aagacggaag attcacagtt ttcttgaaca aaagcggcaa acacttctca   300
ctgcacatca cagcctccca gcctgaagac acagcagtgt acctctgcgc agcaggtgac   360
agtggaggca gcaattacaa actgacattt gggaaaggaa ctctcttaac tgtgactcca   420
aac                                                                 423

<210> SEQ ID NO 196
<211> LENGTH: 393
<212> TYPE: DNA
<213> ORGANISM: Artificial Sequence
<220> FEATURE:
<223> OTHER INFORMATION: Synthetic

<400> SEQUENCE: 196
atgggctcca ggctctttct ggtcttgagc ctcctgtgta caaaacacat ggaggctgca    60
gtcacccaaa gccctagaaa caaggtgaca gtaacaggag gaaacgtgac attgagctgt   120
cgccagacta atagccacaa ctacatgtac tggtatcggc aggacactgg catgggctg    180 aggctgatcc attactcata tggtgctggc aaccttcaaa taggagatgt ccctgatggg   240
tacaaggcca ccagaacaac gcaagaagac ttcttcctcc tgctggaatt ggcttctccc   300
tctcagacat ctttgtactt ctgtgccagc gcgagctggg ggggctatgc tgagcagttc   360
ttcggaccag ggacacgact caccgtccta gag                                393

<210> SEQ ID NO 197
<211> LENGTH: 831
<212> TYPE: DNA
<213> ORGANISM: Artificial Sequence
<220> FEATURE:
<223> OTHER INFORMATION: Synthetic

<400> SEQUENCE: 197
atgactggct tcctgaaggc cttgctgttg gttctgtgcc tgcggccaga atggataaag    60
agtcaacaga agactggtgg ccagcaagtt aaacaaagct ctccatcgct gactgttcaa   120
gagggaggga tattgatcct gaattgtgat tacgagaatg atatgtttga ctattttgcc   180
tggtacaaaa aataccctga caacagcccc acactcctga tatccgtacg ctcaaatgtg   240
gataagaggg aagacggaag attcacagtt ttcttgaaca aaagcggcaa acacttctca   300
ctgcacatca cagcctccca gcctgaagac acagcagtgt acctctgcgc agcaggtgac   360
agtggaggca gcaattacaa actgacattt gggaaaggaa ctctcttaac tgtgactcca   420
aacatccaga cccagaacc tgctgtgtac cagttaaaag atcctcggtc tcaggacagc   480
accctctgcc tgttcaccga ctttgactcc caaatcaatg tgccgaaaac catggaatct   540
ggaacgttca tcactgacaa aactgtgctg gacatgaaag ctatggattc caagagcaat   600
ggggccattg cctggagcaa ccagacaagc ttcacctgcc aagatatctt caaagagacc   660
aacgccacct accccagttc agacgttccc tgtgatgcca cgttgaccga aaaagcttt   720 gaaacagata tgaacctaaa ctttcaaaac ctgtcagtta tgggactccg aatcctcctg   780
ctgaaagtag cgggatttaa cctgctcatg acgctgaggc tgtggtccag t            831
```

<210> SEQ ID NO 198
<211> LENGTH: 912
<212> TYPE: DNA
<213> ORGANISM: Artificial Sequence
<220> FEATURE:
<223> OTHER INFORMATION: Synthetic

<400> SEQUENCE: 198

```
atgggctcca ggctctttct ggtcttgagc ctcctgtgta caaaacacat ggaggctgca    60
gtcacccaaa gccctagaaa caaggtgaca gtaacaggag gaaacgtgac attgagctgt   120
cgccagacta atagccacaa ctacatgtac tggtatcggc aggacactgg gcatgggctg   180
aggctgatcc attactcata tggtgctggc aaccttcaaa taggagatgt ccctgatggg   240
tacaaggcca ccagaacaac gcaagaagac ttcttcctcc tgctggaatt ggcttctccc   300
tctcagacat ctttgtactt ctgtgccagc gcgagctggg ggggctatgc tgagcagttc   360
ttcggaccag ggacacgact caccgtccta gaggatctga aaatgtgac tccacccaag    420
gtctccttgt ttgagccatc aaaagcagag attgcaaaca acaaaaaggc taccctcgtg   480
tgcttggcca ggggcttctt ccctgaccac gtggagctga ctggtgggt gaatggcaag    540
gaggtccaca gtggggtcag cacgaccct caggcctaca aggagagcaa ttatagctac    600
tgcctgagca gccgcctgag ggtctctgct accttctggc acaatcctcg aaaccacttc   660
cgctgccaag tgcagttcca tgggctttca gaggaggaca gtggccaga gggctcaccc    720
aaacctgtca cacagaacat cagtgcagag gcctgggcc gagcagactg tggaatcact   780
tcagcatcct atcatcaggg ggttctgtct gcaaccatcc tctatgagat cctactgggg   840
aaggccaccc tatatgctgt gctggtcagt ggcctggtgc tgatggccat ggtcaagaaa   900
aaaaattcct ga                                                       912
```

<210> SEQ ID NO 199
<211> LENGTH: 408
<212> TYPE: DNA
<213> ORGANISM: Artificial Sequence
<220> FEATURE:
<223> OTHER INFORMATION: Synthetic

<400> SEQUENCE: 199

```
atccagaacc cagaacctgc tgtgtaccag ttaaaagatc ctcggtctca ggacagcacc    60
ctctgcctgt tcaccgactt tgactcccaa atcaatgtgc cgaaaccat ggaatctgga    120
acgttcatca ctgacaaaac tgtgctggac atgaaagcta tggattccaa gagcaatggg   180
gccattgcct ggagcaacca gacaagcttc acctgccaag atatcttcaa agagaccaac   240
gccacctacc ccagttcaga cgttccctgt gatgccacgt tgaccgagaa agctttgaa    300
acagatatga acctaaactt tcaaaacctg tcagttatgg gactccgaat cctcctgctg   360
aaagtagcgg gatttaacct gctcatgacg ctgaggctgt ggtccagt                408
```

<210> SEQ ID NO 200
<211> LENGTH: 519
<212> TYPE: DNA
<213> ORGANISM: Artificial Sequence
<220> FEATURE:
<223> OTHER INFORMATION: Synthetic

<400> SEQUENCE: 200

```
gatctgagaa atgtgactcc acccaaggtc tccttgtttg agccatcaaa agcagagatt    60
gcaaacaaac aaaaggctac cctcgtgtgc ttggccaggg gcttcttccc tgaccacgtg   120
```

```
gagctgagct ggtgggtgaa tggcaaggag gtccacagtg gggtcagcac ggaccctcag    180
gcctacaagg agagcaatta tagctactgc ctgagcagcc gcctgagggt ctctgctacc    240
ttctggcaca atcctcgaaa ccacttccgc tgccaagtgc agttccatgg gctttcagag    300
gaggacaagt ggccagaggg ctcacccaaa cctgtcacac agaacatcag tgcagaggcc    360
tggggccgag cagactgtgg aatcacttca gcatcctatc atcaggggt tctgtctgca    420 accatcctct atgagatcct actggggaag gccaccctat atgctgtgct ggtcagtggc    480
ctggtgctga tggccatggt caagaaaaaa aattcctga                           519
```

<210> SEQ ID NO 201
<211> LENGTH: 605
<212> TYPE: PRT
<213> ORGANISM: Artificial Sequence
<220> FEATURE:
<223> OTHER INFORMATION: Synthetic
<400> SEQUENCE: 201

```
Met Lys Thr Val Thr Gly Pro Leu Phe Leu Cys Phe Trp Leu Gln Leu
 1               5                  10                  15

Asn Cys Val Ser Arg Gly Glu Gln Val Glu Gln Arg Pro Pro His Leu
            20                  25                  30

Ser Val Arg Glu Gly Asp Ser Ala Val Ile Thr Cys Thr Tyr Thr Asp
        35                  40                  45

Pro Asn Ser Tyr Tyr Phe Phe Trp Tyr Lys Gln Glu Pro Gly Ala Ser
    50                  55                  60

Leu Gln Leu Leu Met Lys Val Phe Ser Ser Thr Glu Ile Asn Glu Gly
65                  70                  75                  80

Gln Gly Phe Thr Val Leu Leu Asn Lys Lys Asp Lys Arg Leu Ser Leu
                85                  90                  95

Asn Leu Thr Ala Ala His Pro Gly Asp Ser Ala Ala Tyr Phe Cys Ala
            100                 105                 110

Val Ser Gly Gly Thr Asn Ser Ala Gly Asn Lys Leu Thr Phe Gly Ile
        115                 120                 125

Gly Thr Arg Val Leu Val Arg Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser Arg Ala Lys Arg Ser Gly Ser Gly Ala Thr Asn Phe Ser Leu Leu
        275                 280                 285

Lys Gln Ala Gly Asp Val Glu Glu Asn Pro Gly Pro Met Gly Cys Arg
```

```
                    290                 295                 300
Leu Leu Ser Cys Val Ala Phe Cys Leu Leu Gly Ile Gly Pro Leu Glu
305                 310                 315                 320

Thr Ala Val Phe Gln Thr Pro Asn Tyr His Val Thr Gln Val Gly Asn
                325                 330                 335

Glu Val Ser Phe Asn Cys Lys Gln Thr Leu Gly His Asp Thr Met Tyr
                340                 345                 350

Trp Tyr Lys Gln Asp Ser Lys Lys Leu Leu Lys Ile Met Phe Ser Tyr
                355                 360                 365

Asn Asn Lys Gln Leu Ile Val Asn Glu Thr Val Pro Arg Arg Phe Ser
            370                 375                 380

Pro Gln Ser Ser Asp Lys Ala His Leu Asn Leu Arg Ile Lys Ser Val
385                 390                 395                 400

Glu Pro Glu Asp Ser Ala Val Tyr Leu Cys Ala Ser Ser Arg Asp Trp
                405                 410                 415

Gly Pro Ala Glu Gln Phe Phe Gly Pro Gly Thr Arg Leu Thr Val Leu
                420                 425                 430

Glu Asp Leu Arg Asn Val Thr Pro Pro Lys Val Ser Leu Phe Glu Pro
            435                 440                 445

Ser Lys Ala Glu Ile Ala Asn Lys Gln Lys Ala Thr Leu Val Cys Leu
450                 455                 460

Ala Arg Gly Phe Phe Pro Asp His Val Glu Leu Ser Trp Trp Val Asn
465                 470                 475                 480

Gly Lys Glu Val His Ser Gly Val Ser Thr Asp Pro Gln Ala Tyr Lys
                485                 490                 495

Glu Ser Asn Tyr Ser Tyr Cys Leu Ser Ser Arg Leu Arg Val Ser Ala
                500                 505                 510

Thr Phe Trp His Asn Pro Arg Asn His Phe Arg Cys Gln Val Gln Phe
            515                 520                 525

His Gly Leu Ser Glu Glu Asp Lys Trp Pro Glu Gly Ser Pro Lys Pro
            530                 535                 540

Val Thr Gln Asn Ile Ser Ala Glu Ala Trp Gly Arg Ala Asp Cys Gly
545                 550                 555                 560

Ile Thr Ser Ala Ser Tyr His Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Gly Leu Val Leu Met Ala Met Val Lys Lys Lys Asn Ser
        595                 600                 605
```

<210> SEQ ID NO 202
<211> LENGTH: 1824
<212> TYPE: DNA
<213> ORGANISM: Artificial Sequence
<220> FEATURE:
<223> OTHER INFORMATION: Synthetic

<400> SEQUENCE: 202
atgactggct tcctgaaggc cttgctgttg gttctgtgcc tgcggccaga atggataaag     60
agtcaacaga agactggtgg ccagcaagtt aaacaaagct ctccatcgct gactgttcaa    120
gagggaggga tattgatcct gaattgtgat tacgagaatg atatgtttga ctattttgcc    180
tggtacaaaa ataccctga caacagcccc acactcctga tatccgtacg ctcaaatgtg    240
gataagaggg aagacggaag attcacagtt ttcttgaaca aaagcggcaa acacttctca    300

```
ctgcacatca cagcctccca gcctgaagac acagcagtgt acctctgcgc agcaggtgac    360
agtggaggca gcaattacaa actgacattt gggaaggaa ctctcttaac tgtgactcca    420
aacatccaga acccagaacc tgctgtgtac cagttaaaag atcctcggtc tcaggacagc    480
accctctgcc tgttcaccga ctttgactcc caaatcaatg tgccgaaaac catggaatct    540
ggaacgttca tcactgacaa aactgtgctg gacatgaaag ctatggattc caagagcaat    600
ggggccattg cctggagcaa ccagacaagc ttcacctgcc aagatatctt caaagagacc    660
aacgccacct accccagttc agacgttccc tgtgatgcca cgttgaccga aaaagctttt    720
gaaacagata tgaacctaaa ctttcaaaac ctgtcagtta tgggactccg aatcctcctg    780
ctgaaagtag cgggatttaa cctgctcatg acgctgaggc tgtggtccag tcgggccaag    840
cggtccggat ccggagccac caacttcagc ctgctgaagc aggccggcga cgtggaggag    900
aaccccggcc ccatgggctc caggctctt ctggtcttga gcctcctgtg tacaaaacac    960
atggaggctg cagtcaccca aagccctaga acaaggtga cagtaacagg aggaaacgtg    1020
acattgagct gtcgccagac taatagccac aactacatgt actggtatcg gcaggacact    1080
gggcatgggc tgaggctgat ccattactca tatggtgctg caaccttca ataggagat    1140 gtccctgatg ggtacaaggc caccagaaca acgcaagaag acttcttcct cctgctggaa    1200
ttggcttctc cctctcagac atctttgtac ttctgtgcca gcgcgagctg gggggctat    1260 gctgagcagt tcttcggacc agggacacga ctcaccgtcc tagaggatct gagaaatgtg    1320
actccaccca aggtctcctt gtttgagcca tcaaaagcag agattgcaaa caaacaaaag    1380
gctaccctcg tgtgcttggc caggggcttc ttccctgacc acgtggagct gagctggtgg    1440
gtgaatggca aggaggtcca cagtggggtc agcacggacc ctcaggccta caggagagc    1500 aattatagct actgcctgag cagccgcctg agggtctctg ctaccttctg cacaatcct    1560 cgaaaccact tccgctgcca agtgcagttc catgggcttt cagaggagga caagtggcca    1620
gagggctcac ccaaacctgt cacacagaac atcagtgcag aggcctgggg ccgagcagac    1680
tgtggaatca cttcagcatc ctatcatcag ggggtctgt ctgcaaccat cctctatgag    1740
atcctactgg ggaaggccac cctatatgct gtgctggtca gtggcctggt gctgatggcc    1800
atggtcaaga aaaaaaattc ctga                                           1824
```

<210> SEQ ID NO 203
<211> LENGTH: 607
<212> TYPE: PRT
<213> ORGANISM: Artificial Sequence
<220> FEATURE:
<223> OTHER INFORMATION: Synthetic

<400> SEQUENCE: 203

Met Thr Gly Phe Leu Lys Ala Leu Leu Leu Val Leu Cys Leu Arg Pro
1               5                   10                  15

Glu Trp Ile Lys Ser Gln Gln Lys Thr Gly Gly Gln Gln Val Lys Gln
            20                  25                  30

Ser Ser Pro Ser Leu Thr Val Gln Glu Gly Gly Ile Leu Ile Leu Asn
        35                  40                  45

Cys Asp Tyr Glu Asn Asp Met Phe Asp Tyr Phe Ala Trp Tyr Lys Lys
    50                  55                  60

Tyr Pro Asp Asn Ser Pro Thr Leu Leu Ile Ser Val Arg Ser Asn Val
65                  70                  75                  80

Asp Lys Arg Glu Asp Gly Arg Phe Thr Val Phe Leu Asn Lys Ser Gly
                85                  90                  95

```
Lys His Phe Ser Leu His Ile Thr Ala Ser Gln Pro Glu Asp Thr Ala
                100                 105                 110
Val Tyr Leu Cys Ala Ala Gly Asp Ser Gly Gly Ser Asn Tyr Lys Leu
                115                 120                 125
Thr Phe Gly Lys Gly Thr Leu Leu Thr Val Thr Pro Asn Ile Gln Asn
                130                 135                 140
Pro Glu Pro Ala Val Tyr Gln Leu Lys Asp Pro Arg Ser Gln Asp Ser
145                 150                 155                 160
Thr Leu Cys Leu Phe Thr Asp Phe Asp Ser Gln Ile Asn Val Pro Lys
                165                 170                 175
Thr Met Glu Ser Gly Thr Phe Ile Thr Asp Lys Thr Val Leu Asp Met
                180                 185                 190
Lys Ala Met Asp Ser Lys Ser Asn Gly Ala Ile Ala Trp Ser Asn Gln
                195                 200                 205
Thr Ser Phe Thr Cys Gln Asp Ile Phe Lys Glu Thr Asn Ala Thr Tyr
                210                 215                 220
Pro Ser Ser Asp Val Pro Cys Asp Ala Thr Leu Thr Glu Lys Ser Phe
225                 230                 235                 240
Glu Thr Asp Met Asn Leu Asn Phe Gln Asn Leu Ser Val Met Gly Leu
                245                 250                 255
Arg Ile Leu Leu Leu Lys Val Ala Gly Phe Asn Leu Leu Met Thr Leu
                260                 265                 270
Arg Leu Trp Ser Ser Arg Ala Lys Arg Ser Gly Ser Gly Ala Thr Asn
                275                 280                 285
Phe Ser Leu Leu Lys Gln Ala Gly Asp Val Glu Glu Asn Pro Gly Pro
                290                 295                 300
Met Gly Ser Arg Leu Phe Leu Val Leu Ser Leu Leu Cys Thr Lys His
305                 310                 315                 320
Met Glu Ala Ala Val Thr Gln Ser Pro Arg Asn Lys Val Thr Val Thr
                325                 330                 335
Gly Gly Asn Val Thr Leu Ser Cys Arg Gln Thr Asn Ser His Asn Tyr
                340                 345                 350
Met Tyr Trp Tyr Arg Gln Asp Thr Gly His Gly Leu Arg Leu Ile His
                355                 360                 365
Tyr Ser Tyr Gly Ala Gly Asn Leu Gln Ile Gly Asp Val Pro Asp Gly
                370                 375                 380
Tyr Lys Ala Thr Arg Thr Thr Gln Glu Asp Phe Phe Leu Leu Leu Glu
385                 390                 395                 400
Leu Ala Ser Pro Ser Gln Thr Ser Leu Tyr Phe Cys Ala Ser Ala Ser
                405                 410                 415
Trp Gly Gly Tyr Ala Glu Gln Phe Phe Gly Pro Gly Thr Arg Leu Thr
                420                 425                 430
Val Leu Glu Asp Leu Arg Asn Val Thr Pro Pro Lys Val Ser Leu Phe
                435                 440                 445
Glu Pro Ser Lys Ala Glu Ile Ala Asn Lys Gln Lys Ala Thr Leu Val
                450                 455                 460
Cys Leu Ala Arg Gly Phe Phe Pro Asp His Val Glu Leu Ser Trp Trp
465                 470                 475                 480
Val Asn Gly Lys Glu Val His Ser Gly Val Ser Thr Asp Pro Gln Ala
                485                 490                 495
Tyr Lys Glu Ser Asn Tyr Ser Tyr Cys Leu Ser Ser Arg Leu Arg Val
                500                 505                 510
```

-continued

```
Ser Ala Thr Phe Trp His Asn Pro Arg Asn His Phe Arg Cys Gln Val
            515                 520                 525
Gln Phe His Gly Leu Ser Glu Glu Asp Lys Trp Pro Glu Gly Ser Pro
        530                 535                 540
Lys Pro Val Thr Gln Asn Ile Ser Ala Glu Ala Trp Gly Arg Ala Asp
545                 550                 555                 560
Cys Gly Ile Thr Ser Ala Ser Tyr His Gln Gly Val Leu Ser Ala Thr
                565                 570                 575
Ile Leu Tyr Glu Ile Leu Leu Gly Lys Ala Thr Leu Tyr Ala Val Leu
            580                 585                 590
Val Ser Gly Leu Val Leu Met Ala Met Val Lys Lys Lys Asn Ser
            595                 600                 605

<210> SEQ ID NO 204
<211> LENGTH: 16
<212> TYPE: PRT
<213> ORGANISM: Murine

<400> SEQUENCE: 204

Cys Ala Val Ser Gly Gly Thr Asn Ser Ala Gly Asn Lys Leu Thr Phe
1               5                   10                  15

<210> SEQ ID NO 205
<211> LENGTH: 14
<212> TYPE: PRT
<213> ORGANISM: Murine

<400> SEQUENCE: 205

Cys Ala Ser Ala Ser Trp Gly Gly Tyr Ala Glu Gln Phe Phe
1               5                   10

<210> SEQ ID NO 206
<211> LENGTH: 14
<212> TYPE: PRT
<213> ORGANISM: Murine

<400> SEQUENCE: 206

Cys Thr Cys Ser Ala Asp Arg Gly Ala Glu Thr Leu Tyr Phe
1               5                   10

<210> SEQ ID NO 207
<211> LENGTH: 15
<212> TYPE: PRT
<213> ORGANISM: Murine
<220> FEATURE:
<221> NAME/KEY: MISC_FEATURE
<222> LOCATION: (9)..(9)
<223> OTHER INFORMATION: Wherein X is alanine, arginine, asparagine,
      aspartic acid, cysteine, glutamic acid, glutamine, histidine,
      isoleucine, leucine, lysine, methionine, phenylalanine, proline,
      serine, threonine, tryptophan, tyrosine, or valine

<400> SEQUENCE: 207

Cys Ala Ala Asp Ser Ser Asn Thr Xaa Tyr Gln Asn Phe Tyr Phe
1               5                   10                  15

<210> SEQ ID NO 208
<211> LENGTH: 133
<212> TYPE: PRT
<213> ORGANISM: Murine
<220> FEATURE:
<221> NAME/KEY: MISC_FEATURE
<222> LOCATION: (116)..(116)
<223> OTHER INFORMATION: Wherein X is alanine, arginine, asparagine,
      aspartic acid, cysteine, glutamic acid, glutamine, histidine,
``` isoleucine, leucine, lysine, methionine, phenylalanine, proline, serine, threonine, tryptophan, tyrosine, or valine

<400> SEQUENCE: 208

```
Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Xaa Tyr Gln Asn Phe Tyr Phe Gly Lys Gly Thr Ser Leu
        115                 120                 125

Thr Val Ile Pro Asn
    130
```

<210> SEQ ID NO 209
<211> LENGTH: 269
<212> TYPE: PRT
<213> ORGANISM: Murine
<220> FEATURE:
<221> NAME/KEY: MISC_FEATURE
<222> LOCATION: (116)..(116)
<223> OTHER INFORMATION: Wherein X is alanine, arginine, asparagine, asparatic acid, cysteine, glutamic acid, glutamine, histidine, isoleucine, leucine, lysine, methionine, phenylalanine, proline, serine, threonine, tryptophan, tyrosine, or valine

<400> SEQUENCE: 209

```
Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Xaa Tyr Gln Asn Phe Tyr Phe Gly Lys Gly Thr Ser Leu
        115                 120                 125

Thr Val Ile Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175
```

```
Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265
```